(12) United States Patent
Straub et al.

(10) Patent No.: US 8,445,440 B2
(45) Date of Patent: May 21, 2013

(54) DIMERIC IAP INHIBITORS

(75) Inventors: Christopher Straub, Cambridge, MA (US); Zhuoliang Chen, Cambridge, MA (US); Mark Palermo, Cambridge, MA (US)

(73) Assignee: Novartis AG, Basel (CH)

( * ) Notice: Subject to any disclaimer, the term of this patent is extended or adjusted under 35 U.S.C. 154(b) by 177 days.

(21) Appl. No.: 13/033,463

(22) Filed: Feb. 23, 2011

(65) Prior Publication Data

US 2011/0206690 A1      Aug. 25, 2011

Related U.S. Application Data

(60) Provisional application No. 61/308,114, filed on Feb. 25, 2010, provisional application No. 61/333,927, filed on May 12, 2010, provisional application No. 61/388,410, filed on Sep. 30, 2010.

(51) Int. Cl.
- *A61K 38/05* (2006.01)
- *A61K 38/06* (2006.01)
- *C07K 5/037* (2006.01)

(52) U.S. Cl.
USPC ...... 514/18.9; 514/21.9; 514/21.91; 530/323; 546/279.1

(58) Field of Classification Search
None
See application file for complete search history.

(56) References Cited

U.S. PATENT DOCUMENTS

| | | | |
|---|---|---|---|
| 7,309,792 B2 | 12/2007 | Harran et al. | |
| 7,517,906 B2 | 4/2009 | Condon et al. | |
| 7,638,544 B2 | 12/2009 | Harran et al. | |
| 2005/0197403 A1 | 9/2005 | Harran et al. | |
| 2007/0093428 A1 | 4/2007 | Laurent | |
| 2008/0020986 A1 | 1/2008 | Condon et al. | |
| 2008/0021066 A1 | 1/2008 | Condon et al. | |
| 2009/0005411 A1 | 1/2009 | Jensen et al. | |
| 2009/0104151 A1 | 4/2009 | Hanson et al. | |
| 2009/0123480 A1 | 5/2009 | Wang et al. | |
| 2009/0192140 A1 | 7/2009 | Laurent et al. | |
| 2010/0056495 A1 | 3/2010 | Condon et al. | |
| 2010/0316573 A1 | 12/2010 | Gaither et al. | |
| 2011/0003877 A1 | 1/2011 | Condon et al. | |

FOREIGN PATENT DOCUMENTS

| | | |
|---|---|---|
| WO | 2004/050895 A2 | 6/2004 |
| WO | 2005/074989 A2 | 8/2005 |
| WO | 2006/020060 A2 | 2/2006 |
| WO | 2006/091972 A2 | 2/2006 |
| WO | 2006/122408 A1 | 11/2006 |
| WO | 2007/021825 A2 | 2/2007 |
| WO | 2007/104162 A1 | 9/2007 |
| WO | 2007/131366 A1 | 11/2007 |
| WO | 2007/136921 A2 | 11/2007 |
| WO | 2008/014229 A2 | 1/2008 |
| WO | 2008/014236 A1 | 1/2008 |
| WO | 2008/014238 A2 | 1/2008 |
| WO | 2008/014240 A2 | 1/2008 |
| WO | 2008/014252 A2 | 1/2008 |
| WO | 2008/014263 A2 | 1/2008 |
| WO | 2008/016893 A1 | 2/2008 |
| WO | 2008/085610 A1 | 7/2008 |
| WO | 2008/114925 A1 | 9/2008 |
| WO | 2008/134679 A1 | 11/2008 |
| WO | 2008/137930 A1 | 11/2008 |
| WO | 2009/060292 A2 | 5/2009 |
| WO | 2009/089502 A1 | 7/2009 |
| WO | 2009/094287 A1 | 7/2009 |
| WO | 2009/136290 A1 | 11/2009 |
| WO | 2009/155709 A1 | 12/2009 |
| WO | 2010/015090 A1 | 2/2010 |
| WO | 2010/017035 A2 | 2/2010 |
| WO | 2010/033315 A1 | 3/2010 |
| WO | 2010/033531 A1 | 3/2010 |
| WO | 2011/002684 A1 | 1/2011 |

OTHER PUBLICATIONS

Gao, Zhonghua et al. "A Dimeric Smac/Diablo Peptide Directly Relieves Caspase-3 inhibition by XIAP", The Journal of Biological Chemistry, vol. 282 No. 42, pp. 30718-30727, 2007.
Li, Lin et al. "A Small Molecule Smac Mimic Potentiates TRAIL- and TNFalpha-Mediated Cell Death", Science, vol. 305, pp. 1471-1474, 2004.

*Primary Examiner* — Jeffrey E Russel
(74) *Attorney, Agent, or Firm* — Arlene K. Musser

(57) ABSTRACT

The present invention provides compounds of formula M-L-M' (where M and M' are each independently a monomeric moiety of Formula (I) and L is a linker). The dimeric compounds have been found to be effective in promoting apoptosis in rapidly dividing cells.

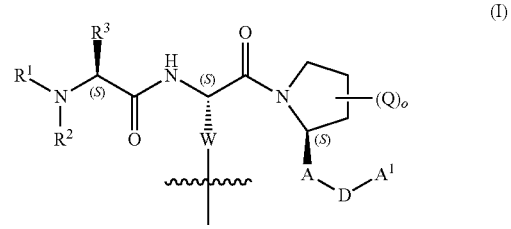

42 Claims, No Drawings

DIMERIC IAP INHIBITORS

This application claims priority to U.S. Provisional Application Ser. No. 61/308,114 filed 25 Feb. 2010, U.S. Provisional Application Ser. No. 61/333,927 filed 12 May 2010, and U.S. Provisional Application Ser. No. 61/388,410 filed 30 Sep. 2010, the contents of which are incorporated herein by reference in their entirety.

FIELD OF THE INVENTION

The present invention relates to dimeric compounds that act as inhibitors of the Inhibitor of Apoptosis Proteins (IAPs), as well as pharmaceutical compositions thereof, methods of their use, and methods for their manufacture.

BACKGROUND

Programmed cell death plays a critical role in regulating cell number and in eliminating stressed or damaged cells from normal tissues. Indeed, the network of apoptotic signaling mechanisms inherent in most cell types provides a major barrier to the development and progression of human cancer. Since most commonly used radiation and chemo-therapies rely on activation of apoptotic pathways to kill cancer cells, tumor cells which are capable of evading programmed cell death often become resistant to treatment.

Apoptosis signaling networks are classified as extrinsic when mediated by death receptor-ligand interactions or intrinsic when mediated by cellular stress and mitochondrial permeabilization. Both pathways ultimately converge on individual caspases, cysteine-aspartic proteases. Once activated, caspases cleave a number of cell death-related substrates, effecting destruction of the cell.

Tumor cells have devised a number of strategies to circumvent apoptosis. One recently reported molecular mechanism involves the overexpression of members of the IAP (Inhibitor of Apoptosis Protein) family. IAPs sabotage apoptosis by directly interacting with and neutralizing caspases. The prototype IAPs, XIAP and cIAP have three functional domains referred to as BIR 1, 2 & 3 domains. The BIR3 domain interacts directly with caspase 9 and inhibits its ability to bind and cleave its natural substrate, procaspase 3.

A proapoptotic mitochondrial protein, Smac (also known as DIABLO), can neutralize XIAP and/or cIAP by binding to a peptide binding pocket (Smac binding site) on the surface of BIR3 thereby precluding interaction with caspase 9. Binding of peptides derived from Smac has also been reported to trigger autocatalytic polyubiquitination and subsequent proteosome-mediated degradation of cIAP1. The present invention relates to therapeutic molecules that bind to the Smac binding pocket thereby promoting apoptosis in rapidly dividing cells. Such therapeutic molecules are useful for the treatment of proliferative diseases, including cancer.

SUMMARY

The present invention provides compounds of formula M-L-M' which have been found to be effective in promoting apoptosis in rapidly dividing cells. Advantageously, the compounds of the present invention are selectively more toxic to abnormal cells e.g. cells that are proliferating more rapidly than normal cells, particularly in human tumor or cancer cells. Accordingly, the compounds of the present invention are useful in the treatment of diseases and conditions characterized by cell proliferation.

In each of the embodiments below, M and M' are preferably both the same.

In one embodiment of the present invention, a compound of formula M-L-M' is provided where M and M' are each independently a monomeric moiety of Formula (I)

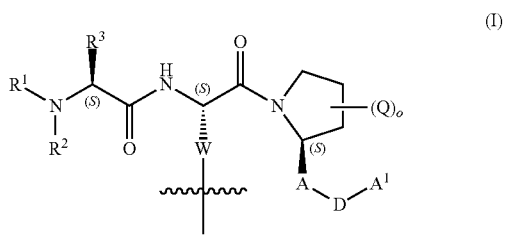

wherein:
$R^1$ is $(C_1-C_4)$alkyl or hydrogen;
$R^2$ is hydrogen, $(C_1-C_4)$alkyl, halo-substituted $(C_1-C_4)$alkyl, $(C_3-C_6)$cycloalkyl, —$CH_2$—$(C_3-C_6)$cycloalkyl, benzyl, HO—$(C_1-C_4)$alkyl-, or $CH_3NHC(O)$—;
$R^3$ is $(C_1-C_4)$alkyl, halo-substituted $(C_1-C_4)$alkyl, or hydrogen;
or $R^2$ along with the nitrogen atom to which $R^2$ is attached is taken together with $R^3$ to form a 3- to 6-membered heterocyclic ring optionally containing 1 to 2 additional hetero-ring atoms each independently selected from N, O and S;
Q is $(C_1-C_4)$alkyl, $(C_1-C_4)$alkoxy, —OH, —C(O)—$(C_1-C_4)$alkyl, —O—C(O)—$(C_1-C_4)$alkyl, —$NH_2$, —NH—$(C_1-C_4)$alkyl, —N$((C_1-C_4)$alkyl$)_2$, —NH—C(O)—$(C_1-C_4)$alkyl, —NHSO$(C_1-C_4)$alkyl, —NHSO(phenyl), —N$((C_1-C_4)$alkyl$)$-SO$(C_1-C_4)$alkyl, —N$((C_1-C_4)$alkyl$)$-SO(phenyl), —NHSO$_2(C_1-C_4)$alkyl, —NHSO$_2$(phenyl), —N$((C_1-C_4)$alkyl$)$-SO$_2(C_1-C_4)$alkyl, or —N$((C_1-C_4)$alkyl$)$-SO$_2$(phenyl);
o is 0, 1, or 2;
A is a 6-membered heteroaryl ring containing at least one N ring heteroatom;
D is a bond, —C(O)—, —O—, —NH—, —S—, —S(O)—, —SO$_2$—, —N$((C_1-C_4)$alkyl$)$-, —N$((C_1-C_4)$alkyl-OH)—, —N$((C_3-C_6)$cycloalkyl$)$-, —NHC(O)—, —N$((C_1-C_4)$alkyl$)$C(O)—, —C(O)NH—, —C(O)—N$((C_1-C_4)$alkyl$)$-, —N$((C_1-C_4)$alkyl-CO$_2$—$(C_1-C_4)$alkyl$)$-, —$(C_1-C_4)$alkylene, $(C_2-C_6)$alkenylene, —CH(OH)—, —C(O)—$(C_1-C_4)$alkylene, —NH—$(C_1-C_4)$alkylene, —S—$(C_1-C_4)$alkylene, —S(O)—$(C_1-C_4)$alkylene, —SO$_2$—$(C_1-C_4)$alkylene, —NHSO$_2(C_1-C_4)$alkylene, —NHSO$(C_1-C_4)$alkylene, or —CH(R)—, where R is $NH_2$, —NH$((C_1-C_4)$alkylene)phenyl), —NH$(C_1-C_4)$alkyl, —O$((C_1-C_4)$alkylene)phenyl) or —O$(C_1-C_4)$alkyl, wherein said $((C_1-C_4)$alkylene)phenyl) or $(C_1-C_4)$alkyl is optionally substituted with halo;
$A^1$ is H, $CF_3$, phenyl, naphthyl, a partially or fully saturated $(C_3-C_6)$cycloalkyl, a 5- to 12 membered partially or fully saturated heterocycle containing 1 to 3 heteroatoms each independently selected from O, S or N, or a 5- to 10-membered heteroaryl containing 1 to 4 heteroatoms each independently selected from O, S or N,
where said phenyl, naphthyl and said heteroaryl are optionally substituted with 1 to 3 substituents each independently selected from halo, $(C_1-C_4)$alkyl, halo-substituted$(C_1-C_4)$alkyl, $(C_1-C_4)$alkoxy, —C(O)NHCH$_3$, —C(O)N(CH$_3$)$_2$, CN, or NO$_2$, and
where said heterocycle and said cycloalkyl are optionally fused to a phenyl or 6-membered heteroaryl containing 1 to 3 heteroatoms each independently selected from O, S or N, and where said heterocycle, said cycloalkyl, said fused heterocycle and said fused cycloakyl are optionally substituted with oxo, halo, $(C_1\text{-}C_4)$alkyl, halo-substituted$(C_1\text{-}C_4)$alkyl, or $(C_1\text{-}C_4)$alkoxy;

W is a bond, $(C_1\text{-}C_{10})$alkylene, $(C_1\text{-}C_{10})$alkenylene, $((C_1\text{-}C_4)\text{alkylene})_m\text{-}(Y)_n\text{—}B$, $((C_1\text{-}C_4)\text{alkenylene})_m\text{-}(Y)_n\text{—}B$, where m and n are each independently 0 or 1, Y is phenylene, naphthylene, a partially or fully saturated 3- to 6-membered cycloalkylene, 5- to 6-membered fully or partially saturated heterocyclene containing 1 to 3 heteroatoms each independently selected from O, S or N, or a 5- to 10-heteroarylene containing 1 to 4 heteroatoms each independently selected from O, S, or N, and B is a bond, —O—, $(C_1\text{-}C_4)$alkylene, or —$(CH_2)$(phenylene), where said $(C_1\text{-}C_{10})$alkylene, $(C_1\text{-}C_{10})$alkenylene, $(C_1\text{-}C_4)$ alkylene, or $(C_1\text{-}C_4)$alkenylene moiety optionally contains an oxygen or nitrogen atom interspersed within the alkylene chain and is optionally substituted with oxo, —$CF_3$, phenyl, naphthyl, a 5- to 10-membered heteroaryl containing 1 to 4 heteroatoms each independently selected from O, S, or N, a partially or fully saturated 5- to 6-membered cycloalkyl, a 5- to 6-membered fully or partially saturated heterocycle containing 1 to 3 heteroatoms each independently selected from O, S or N, and/or 1 or more halo, where said partially or fully saturated heterocyclene is optionally substituted with 1 to 2 substituents each independently selected from oxo, $(C_1\text{-}C_4)$alkyl, or halo, where said heteroaryl or said heteroarylene is optionally substituted with 1 to 3 substituents selected from halo or $(C_1\text{-}C_4)$alkyl, and where said phenylene, said phenyl, said naphthyl, said naphthylene, said cycloalkylene, or said cycloalkyl is optionally substituted with 1 to 3 substitutents each independently selected from halo, —$CF_3$, $(C_1\text{-}C_4)$alkyl, or $(C_1\text{-}C_4)$alkoxy, or when W is $((C_1\text{-}C_4)\text{alkylene})_m\text{-}(Y)_n\text{—}B$ or $((C_1\text{-}C_4)$ alkenylene$)_m\text{-}(Y)_n\text{—}B$ and L is $NR^5\text{—}C(O)\text{—}X^2\text{—}C(O)\text{—}NR^5\text{—}$ or $\text{—}NR^5\text{—}S(O)_2\text{—}X^2\text{—}S(O)_2\text{—}NR^5\text{—}$, B is optionally taken together with $R^5$ along with the nitrogen to which $R^5$ is attached to form a heterocyclic ring selected from the group consisting of aziridinyl, azetidinyl, pyrrolidinyl, 1H-pyrrolyl, piperidinyl, 1H-indolyl, indolinyl, 1H-dihydroimidazolyl, 1H-imidazolyl, piperazinyl, hexahydropyrimidinyl, 1,2,3,4-tetrahydroquinolinyl, 1,2,3,4-tetrahydroisoquinolinyl, 5,6,7,8-tetrahydropyrido[3,4-b]pyrazinyl, oxazolidinyl, and thiazolidinyl, where said heterocyclic ring is optionally substituted with 1 to 3 substituents each independently selected from $(C_1\text{-}C_4)$alkyl, —OH, or oxo;

L is a linker group selected from the group consisting of —C(O)—$NR^5$—$X^1$—$NR^5$—C(O)—, —$S(O)_2$—$NR^5$—$X^1$—$NR^5$—$S(O)_2$—, —$NR^5$—C(O)—$X^2$—C(O)—$NR^5$—, and —$NR^5$—$S(O)_2$—$X^2$—$S(O)_2$—$NR^5$—, where $R^5$ is hydrogen, $(C_1\text{-}C_4)$alkyl, benzyl, or cyclohexyl; and $X^1$ is (i) a bond, (ii) $(C_1\text{-}C_{10})$alkylene, $(C_2\text{-}C_{10})$alkenylene, $(C_2\text{-}C_{10})$alkynylene, $((C_1\text{-}C_{10})\text{alkylene})\text{-}(O(C_1\text{-}C_6)\text{alkylene})_p\text{-}$, or $(C_1\text{-}C_{10})$alkylene-NH$(C_1\text{-}C_6)$alkylene, where p is 0, 1 or 2, (iii) phenylene, napthylene, fluorenylene, 9H-fluoren-9-onylene, 9,10-dihydroanthracenylene, anthracen-9,10-dionylene, a partially or fully saturated $(C_3\text{-}C_8)$cycloalkylene, a 5- to 7-membered heterocyclene containing 1 to 3 heteroatoms each independently selected from O, S, or N, or a 5- to 10-membered heteroarylene containing 1 to 3 heteroatoms each independently selected from O, S or N, where said phenylene is optionally fused to a $(C_5\text{-}C_6)$cycloalkyl, (iv) (phenylene)-G-(phenylene), where G is a bond, O, S, —NH—, —N=N—, —S=S—, —$SO_2$—, $(C_1\text{-}C_6)$ alkylene, $(C_2\text{-}C_6)$alkenylene, $(C_2\text{-}C_{10})$alkynylene, $(C_3\text{-}C_6)$cycloalkylene, a 5- to 6-membered heteroaryl containing 1 to 3 heteroatoms each independently selected from O, S or N, or a 5- to 6-membered partially or fully saturated heterocyclene containing 1 to 3 heteroatoms each independently selected from O, S or N, and where said phenylene is optionally fused to a phenyl, (v) $((C_1\text{-}C_6)\text{alkylene})_r\text{-}Z^1\text{—}((C_1\text{-}C_6)\text{alkylene})_s$, or $((C_1\text{-}C_6)\text{alkenylene})_r\text{-}Z^1\text{—}((C_1\text{-}C_6)\text{alkenylene})_s$, where r and s are each independently 0, 1, or 2; and $Z^1$ is —O—, —N=N—, $(C_3\text{-}C_6)$cycloalkylene, phenylene, a 5- to 6-membered partially or fully saturated heterocyclene containing 1 to 3 heteroatoms each independently selected from O, S or N, or a 5- to -6-membered heteroarylene containing 1 to 3 heteroatoms each independently selected from O, S or N, where said heteroarylene and said heterocyclene are optionally fused to a phenyl, phenylene, a 5- to 6-membered partially or fully saturated heterocyclene containing 1 to 3 heteroatoms each independently selected from O, S or N, or a 5- to -6-membered heteroarylene containing 1 to 3 heteroatoms each independently selected from O, S or N, or (vi) $(C_1\text{-}C_{20})$alkylene or —NH—$((C_1\text{-}C_{20})\text{alkylene})$-NH—, where said alkylene contains 1 to 6 oxygen atoms interspersed within the alkylene chain and optionally 1 to 2 phenylene groups interpersed within the alkylene chain;

or $X^1$ is optionally taken together with both $R^5$ groups along with the nitrogens to which both $R^5$ groups are attached to form an 2,6-diazaspiro[3.3]heptane;

$X^2$ is (i) a bond or —O—, —NH—, or —N$((C_1\text{-}C_4)$alkyl)-, (ii) $(C_1\text{-}C_{10})$alkylene, —$(O(C_1\text{-}C_6)\text{alkylene})_p$-, —$((C_1\text{-}C_6)\text{alkylene O})_q$—, —O—$((C_1\text{-}C_6)\text{alkylene O})_q$—, $(C_2\text{-}C_{10})$alkenylene, $((C_1\text{-}C_{10})\text{alkylene})\text{-}(O(C_1\text{-}C_6)$ alkylene$)_p$-, —O—$((C_1\text{-}C_{10})\text{alkyl})$-O—, $(C_1\text{-}C_{10})$alkylene-NH$(C_1\text{-}C_6)$alkylene, or $(C_2\text{-}C_{10})$alkynylene, where p and q are each independently 1, 2, or 3, (iii) phenylene, napthylene, fluorenylene, 9H-fluoren-9-onylene, 9,10-dihydroanthracenylene, anthracen-9,10-dionylene, a partially or fully saturated $(C_3\text{-}C_8)$cycloalkylene, a 5- to 7-membered heterocyclene containing 1 to 3 heteroatoms each independently selected from O, S, or N, or a 5- to 10-membered heteroarylene containing 1 to 3 heteroatoms each independently selected from O, S or N, where said phenylene is optionally fused to a $(C_5\text{-}C_6)$cycloalkyl, (iv) (phenylene)-G-(phenylene), or —O-(phenylene)-G-(phenylene)-O—, where G is a bond, O, S, —NH—, —N=N—, —S=S—, —$SO_2$—, $(C_1\text{-}C_6)$alkylene, $(C_2\text{-}C_6)$alkenylene, $(C_3\text{-}C_6)$cycloalkylene, a 5- to 6-membered heteroaryl containing 1 to 3 heteroatoms each independently selected from O, S or N, or a 5- to 6-membered partially or fully saturated heterocyclene containing 1 to 3 heteroatoms each independently selected from O, S or N, and where said phenylene is optionally fused to a phenyl, (v) $((C_1-C_6)\text{alkylene})_r-Z^1-((C_1-C_6)\text{alkylene})_s$, $((C_1-C_6)\text{alkenylene})_r-Z^1-((C_1-C_6)\text{alkenylene})_s$, or $-(O(C_1-C_3)\text{alkylene})_u-Z^2-((C_1-C_3)\text{alkylene O})_v-$, where r, s, u, and v are each independently 0, 1, or 2; and $Z^1$ and $Z^2$ are $-O-$, $-N=N-$, $(C_3-C_6)$cycloalkylene, phenylene, a 5- to 6-membered partially or fully saturated heterocyclene containing 1 to 3 heteroatoms each independently selected from O, S or N, or a 5- to -6-membered heteroarylene containing 1 to 3 heteroatoms each independently selected from O, S or N, where said heteroarylene and said heterocyclene are optionally fused to a phenyl, phenylene, a 5- to 6-membered partially or fully saturated heterocyclene containing 1 to 3 heteroatoms each independently selected from O, S or N, or a 5- to -6-membered heteroarylene containing 1 to 3 heteroatoms each independently selected from O, S or N, or (vi) $(C_1-C_{20})$alkylene or $-NH-((C_1-C_{20})\text{alkylene})-NH-$, where said alkylene contains 1 to 6 oxygen atoms interspersed within the alkylene chain and optionally 1 to 2 phenylene groups interspersed within the alkylene chain;

where said group (ii) moieties of $X^1$ and $X^2$ are each independently substituted with one or more fluoro atoms, or 1 to 2 substituents each independently selected from halo, oxo, amino, phenyl, naphthyl, $(C_3-C_6)$cycloalkyl, or 5- to 6-membered heterocycle containing 1 to 3 heteroatoms each independently selected from O, N or S, where said phenyl, said cycloalkyl, and said heterocycle are optionally substituted with 1 to 3 substituents each independently selected from halo, $(C_1-C_4)$alkyl, or trifluoromethyl, where said group (iii) and (iv) moieties of $X^1$ and $X^2$ are optionally substituted with 1 to 4 substituents each independently selected from $(C_1-C_4)$alkyl, $(C_1-C_4)$alkoxy, halo, amino, $-OH$, benzyl, or a fused 5- to 6-membered cycloalkyl, where said $(C_1-C_4)$alkyl, said $(C_1-C_4)$alkoxy, and said fused cycloalkyl are optionally substituted with 1 to 3 substituents selected from halo, $(C_1-C_4)$alkyl, where said group (v) moieties of $X^1$ and $X^2$ are optionally substituted with 1 to 3 substituents each independently selected from halo, hydroxy, oxo, amino, $(C_1-C_4)$alkyl, $(C_1-C_4)$alkoxy, or phenyl; or a pharmaceutically acceptable salt thereof.

Preferably, M and M' are the same; or a pharmaceutically acceptable salt thereof.

In one embodiment, L is $-C(O)-NR^5-X^1-NR^5-C(O)-$, or $-S(O)_2-NR^5-X^1-NR^5-S(O)_2-$, where $R^5$ is hydrogen or $(C_1-C_4)$alkyl; or a pharmaceutically acceptable salt thereof.

In another embodiment, L is $-NR^5-C(O)-X^2-C(O)-NR^5-$, or $-NR^5-S(O)_2-X^2-S(O)_2-NR^5-$, where $R^5$ is hydrogen or $(C_1-C_4)$alkyl; or a pharmaceutically acceptable salt thereof.

In each of the embodiments, $R^1$ is preferably hydrogen, $R^2$ and $R^3$ are preferably both methyl, and D is preferably a bond, $-C(O)-$, $-CH_2-$, $-CH(OH)-$, $-CH(NH_2)-$, $-O-$, $-S-$, $-S(O)-$, $-S(O)_2-$, $-NH-$, $-N((C_1-C_4)\text{alkyl})-$, $-N((C_1-C_4)\text{alkyl-OH})-$, or $-N(\text{cyclopropyl})-$; or a pharmaceutically acceptable salt thereof.

In each of the embodiments, W is preferably $(C_1-C_{10})$alkylene, 5- to 6-membered cycloalkylene, or $((C_1-C_4)\text{alkylene})$phenylene; or a pharmaceutically acceptable salt thereof.

In another embodiment, a compound of formula M-L-M' is provided wherein M and M' are each independently a monomeric moiety of formula (II):

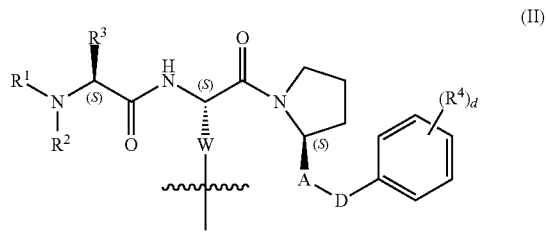

(II)

wherein:

$R^1$ is $(C_1-C_4)$alkyl or hydrogen;

$R^2$ is $(C_1-C_4)$alkyl or hydrogen;

$R^3$ is $(C_1-C_4)$alkyl or hydrogen;

or $R^2$ along with the nitrogen atom to which it is attached is taken together with $R^3$ to form a 3- to 6-membered heterocyclic ring optionally containing 1 to 2 additional hetero-ring atoms each independently selected from N, O and S;

A is a 6-membered heteroaryl ring containing at least one N ring heteroatom, where said heteroaryl is optionally substituted with $(C_1-C_4)$alkyl, $-SCH_3$, $-OCH_3$, or halo;

D is a bond, $-C(O)-$, $-CH_2-$, $-CH(OH)-$, $-CH(NH_2)-$, $-O-$, $-S-$, $-S(O)-$, $-S(O)_2-$, $-NH-$, $-N((C_1-C_4)\text{alkyl})-$, $-N((C_1-C_4)\text{alkyl-OH})-$, or $-N(\text{cyclopropyl})-$;

W is $(C_1-C_{10})$alkylene, 5- to 6-membered cycloalkylene, or $((C_1-C_4)\text{alkylene})$phenylene;

d is 0, 1, 2, or 3;

$R^4$ is halo, $-CF_3$, $(C_1-C_4)$alkyl, or $(C_1-C_4)$alkoxy; and

L is a linker group selected from the group consisting of $-C(O)-NR^5-X^1-NR^5-C(O)-$, $-S(O)_2-NR^5-X^1-NR^5-S(O)_2-$, $-NR^5-C(O)-X^2-C(O)-NR^5-$, and $-NR^5-S(O)_2-NR^5-$, where $R^5$ is hydrogen or $(C_1-C_4)$alkyl; and $X^1$ and $X^2$ are $(C_1-C_{10})$alkylene, $-(O(C_1-C_3)\text{alkylene})_p-$, $-((C_1-C_3)\text{alkylene O})_q-$, $(C_2-C_{10})$alkenylene, phenylene, napthylene, or bis(phenylene), where p and q are each independently 1, 2, 3 or 4; or a pharmaceutically acceptable salt thereof.

In a particular embodiment, A is pyridinyl or pyrimidyl; or a pharmaceutically acceptable salt thereof.

In each of the embodiments, $R^1$ is preferably hydrogen, and $R^2$ and $R^3$ are preferably both methyl; or a pharmaceutically acceptable salt thereof.

In each of the embodiments, D is preferably $-C(O)-$, $-CH_2-$, $-O-$, $-NH-$, $-N((C_1-C_4)\text{alkyl})-$, or $-N(\text{cyclopropyl})-$; or a pharmaceutically acceptable salt thereof.

In each of the embodiments, M and M' are preferably the same monomeric moiety; or a pharmaceutically acceptable salt thereof.

In yet another embodiment, a compound of Formula M-L-M' is provided wherein M and M' are the same and each are a monomeric moiety of Formula (III)

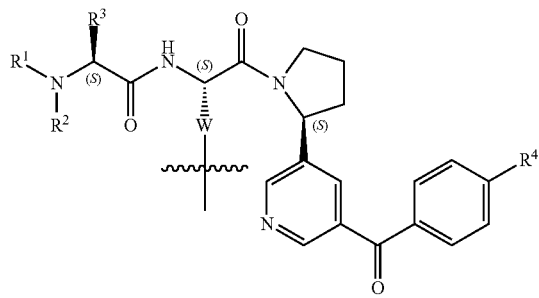

(III)

where,

R¹ is $(C_1-C_4)$alkyl or hydrogen;

R² is $(C_1-C_4)$alkyl or hydrogen;

R³ is $(C_1-C_4)$alkyl or hydrogen, or

R¹ or R² along with the nitrogen to which R¹ or R² is attached is taken together with R³ to form an aziridinyl, azetidinyl, pyrrolidinyl, or piperidinyl;

R⁴ is fluorine;

W is $(C_1-C_{10})$alkylene, or $(C_1-C_4)$alkylenephenylene; and

L is a linker group selected from the group consisting of —C(O)—NR⁵—X¹—NR⁵—C(O)—, —S(O)₂—NR⁵—X¹—NR⁵—S(O)₂—, —NR⁵—C(O)—X²—C(O)—NR⁵—, and —NR⁵—S(O)₂—X²—S(O)₂—NR⁵—, where R⁵ is hydrogen, and X¹ and X² are $(C_1-C_{10})$alkylene, phenylene, naphthylene, or bis(phenylene); or a pharmaceutically acceptable salt thereof.

In one embodiment, R¹ is hydrogen; R² is methyl; and R³ is preferably methyl; or a pharmaceutically acceptable salt thereof.

In another embodiment, R¹ is hydrogen; and R² taken together with R³ forms an azetidinyl; or a pharmaceutically acceptable salt thereof.

In yet another embodiment, W is n-butylene or —CH₂-(phenylene)-; or a pharmaceutically acceptable salt thereof.

In another embodiment, W is n-butylene; or a pharmaceutically acceptable salt thereof.

In yet another embodiment, W is a —CH₂-(phenylene)-; or a pharmaceutically acceptable salt thereof.

In one embodiments, L is —NR⁵—C(O)—X²—C(O)—NR⁵—, where X² is n-propylene, n-butylene, n-pentylene, n-hexylene, n-heptylene, n-octylene, 1,3-phenylene, 1,4-phenylene, or 4,4'-biphenyl; or a pharmaceutically acceptable salt thereof.

In another embodiment, L is —NR⁵—S(O)₂—X²—S(O)₂—NR⁵—, where X² is 1,3-phenylene, 4,4'-biphenyl, 2,7-naphthylene, or 2,6-naphthylene; or a pharmaceutically acceptable salt thereof.

Representative compounds include: Heptanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide}; (S)—N—((S)-1-((S)-2-(5-(4-fluorobenzoyl)pyridin-3-yl)pyrrolidin-1-yl)-6-(3-(N—((S)-6-((S)-2-(5-(4-fluorobenzoyl)pyridin-3-yl)pyrrolidin-1-yl)-5-((S)-2-(methylamino)propanamido)-6-oxohexyl)sulfamoyl)phenylsulfonamido)-1-oxohexan-2-yl)-2-(methylamino)propanamide; N,N'-Bis-[(S)-6-{(S)-2-[5-(4-fluoro-benzoyl)-pyridin-3-yl]-pyrrolidin-1-yl}-5-((S)-2-methylamino-propionylamino)-6-oxo-hexyl]-terephthalamide; (S)—N—((S)-1-((S)-2-(5-(4-fluorobenzoyl)pyridin-3-yl)pyrrolidin-1-yl)-6-(4'-(N—((S)-6-((S)-2-(5-(4-fluorobenzoyl)pyridin-3-yl)pyrrolidin-1-yl)-5-((S)-2-(methylamino)propanamido)-6-oxohexyl)sulfamoyl)biphenyl-4-ylsulfonamido)-1-oxohexan-2-yl)-2-(methylamino)propanamide; N,N'-Bis-[(S)-6-{(S)-2-[5-(4-fluoro-benzoyl)-pyridin-3-yl]-pyrrolidin-1-yl}-5-((S)-2-methylamino-propionylamino)-6-oxo-hexyl]-isophthalamide; Nonanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide}; Decanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide}; (S)—N—((S)-1-((S)-2-(5-(4-fluorobenzoyl)pyridin-3-yl)pyrrolidin-1-yl)-6-(7-(N—((S)-6-((S)-2-(5-(4-fluorobenzoyl)pyridin-3-yl)pyrrolidin-1-yl)-5-((S)-2-(methylamino)propanamido)-6-oxohexyl)sulfamoyl)naphthalene-2-sulfonamido)-1-oxohexan-2-yl)-2-(methylamino)propanamide; (S)—N—((S)-1-((S)-2-(5-(4-fluorobenzoyl)pyridin-3-yl)pyrrolidin-1-yl)-6-(6-(N—((S)-6-((S)-2-(5-(4-fluorobenzoyl)pyridin-3-yl)pyrrolidin-1-yl)-5-((S)-2-(methylamino)propanamido)-6-oxohexyl)sulfamoyl)naphthalene-2-sulfonamido)-1-oxohexan-2-yl)-2-(methylamino)propanamide; Biphenyl-4,4'-dicarboxylic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide}; Biphenyl-4,4'-dicarboxylic acid bis-[((S)-5-[((S)-azetidine-2-carbonyl)-amino]-6-{(S)-2-[5-(4-fluoro-benzoyl)-pyridin-3-yl]-pyrrolidin-1-yl}-6-oxo-hexyl]-amide]; Heptanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); Decanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); Hexanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); N,N'-Bis-{4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-isophthalamide; Nonanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); and Pentanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); or a pharmaceutically acceptable salt thereof.

Preferred representative compounds include: Heptanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide}; N,N'-Bis-[(S)-6-{(S)-2-[5-(4-fluoro-benzoyl)-pyridin-3-yl]-pyrrolidin-1-yl}-5-((S)-2-methylamino-propionylamino)-6-oxo-hexyl]-terephthalamide; N,N'-Bis-[(S)-6-{(S)-2-[5-(4-fluoro-benzoyl)-pyridin-3-yl]-pyrrolidin-1-yl}-5-((S)-2-methylamino-propionylamino)-6-oxo-hexyl]-isophthalamide; Nonanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide}; Decanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide}; Biphenyl-4,4'-dicarboxylic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide}; Biphenyl-4,4'-dicarboxylic acid bis-[((S)-5-[((S)-azetidine-2-carbonyl)-amino]-6-{(S)-2-[5-(4-fluoro-benzoyl)-pyridin-3-yl]-pyrrolidin-1-yl}-6-oxo-hexyl]-amide]; Heptanedioic acid bis-({4-[(S)-3-{(S)-2-[5-(4-fluoro-benzoyl)-pyridin-3-yl]- pyrrolidin-1-yl}-2-((S)-2-methylamino-propionylamino)-3-oxo-propyl]-phenyl}-amide); Decanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); and Nonanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); or a pharmaceutically acceptable salt thereof.

More preferred representative compounds include: Biphenyl-4,4'-dicarboxylic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide}; Decanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide}; Decanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); Nonanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide}; Heptanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); and Nonanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); or a pharmaceutically acceptable salt thereof.

In another aspect of the present invention, a pharmaceutical composition is provided which comprises any one of the compounds described above, or a pharmaceutically acceptable salt thereof, and a pharmaceutically acceptable carrier, diluent or excipient. The pharmaceutical composition may further comprise at least one additional pharmaceutical agent (described herein below). In particular, the at least one additional pharmaceutical agent is paclitaxel, a PI3K inhibitor, a topoisomerase inhibitor, a Trail antibody, recombinant Trail, or a Trail receptor agonist. More particularly, the at least one additional pharmaceutical agent is paclitaxel.

In yet another aspect of the present invention, a method for treating a disease, disorder, or condition associated with the overexpression of an IAP in a subject is provided which comprises the step of administering to a subject in need to such treatment a therapeutically effective amount of any one of the compounds described above, or a pharmaceutically acceptable salt thereof.

In yet another aspect, a method for treating a disease, disorder, or condition mediated by IAPs is provided which comprises the step of administering to a subject in need of such treatment a therapeutically effective amount of any one of the compounds described above, or a pharmaceutically acceptable salt thereof.

In yet another aspect, the use of any one of the compounds described above is provided for inducing or enhancing apoptosis in a tumor or cancer cell.

Any one of the compounds described above may be used as a medicament.

Also is described is described is the use of any one of the compounds described above in the manufacture of a medicament for the treatment of a disease, disorder or condition mediated by IAPs.

In another aspect, the use of any one of the compounds described above is provided for the treatment of a disease, disorder or condition associated with the overexpression of an IAPs.

In yet another aspect, a method for treating a disease, disorder, or condition mediated by IAPs is provided which comprises the step(s) of administering to a patient in need of such treatment (i) any one of the compounds described above, or a pharmaceutically acceptable salt thereof; and (ii) at least one additional pharmaceutical agent.

In particular, the additional pharmaceutical agent is paclitaxel, a PI3K inhibitor, a topoisomerase inhibitor, a Trail antibody, recombinant Trail, or a Trail receptor agonist. More particularly, the additional pharmaceutical agent is paclitaxel.

The compound, or pharmaceutical acceptable salt thereof, and the additional pharmaceutical agent may be administered simultaneously or sequentially.

In yet another aspect, a method for treating a disease, disorder, or condition mediated by IAP is provided which comprises the step of administering to a patient in need of such treatment a pharmaceutical composition comprising any one of the compounds described above, or a pharmaceutically acceptable salt thereof, and a pharmaceutical acceptable carrier. The method composition may further comprise at least one additional pharmaceutical agent. In particular, the additional pharmaceutical agent is paclitaxel, a PI3K inhibitor, a topoisomerase inhibitor, a Trail antibody, recombinant Trail, or a Trail receptor agonist. More particularly, the additional pharmaceutical agent is paclitaxel.

In yet another aspect, a method for treating a disease, disorder, or condition mediated by IAPs is provided which comprises the step(s) of administering to a patient in need of such treatment (i) a first composition comprising any one of the compounds described above, or a pharmaceutically acceptable salt thereof, and a pharmaceutical carrier; and (ii) a second composition comprising at least one additional pharmaceutical agent (described herein below) and a pharmaceutical carrier. In particular, the additional pharmaceutical agent is paclitaxel, a PI3K inhibitor, a topoisomerase inhibitor, a Trail antibody, recombinant Trail, or a Trail receptor agonist. More particularly, the additional pharmaceutical agent is a paclitaxel. The first composition and the second composition may be administered simultaneously or sequentially.

Definitions

As used herein, the term "alkyl" refers to a hydrocarbon moiety of the general formula $C_nH_{2n+1}$. The alkane group may be straight or branched. For example, the term "($C_1$-$C_{10}$) alkyl" refers to a monovalent, straight, or branched aliphatic group containing 1 to 10 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, heptyl, and the like). Similarly, the alkyl portion (i.e., alkyl moiety) of an alkoxy have the same definition as above. When indicated as being "optionally substituted", the alkane radical or alkyl moiety may be unsubstituted or substituted with one or more substituents (generally, one to three substituents except in the case of halogen substituents such as perchloro or perfluoro-alkyls). "Halo-substituted alkyl" refers to an alkyl group having at least one halogen substitution.

The term "alkenyl" refers to an alkyl moiety containing at least one unsaturation in the alkyl group. The alkenyl group may be straight or branched. For example, vinyl, prop-1-enyl, prop-2-enyl, allenyl, 2-methylprop-2-enyl, 3-methylbut-2-enyl, butadienyl, and the like.

The term "alkynyl" refers to an alkyl moiety containing at least one triple bond. The alkynyl group may be straight of branched. For example, CH₃—C≡C—, H—C≡C—CH₂—, CH₃—C≡C—CH₂—, H—C≡C—CH(CH₃)—, H—C≡C—CH₂CH₂—, H—C≡C—CH(CH₃)CH₂—, H—C≡C—CH₂—C≡C—CH₂—, and the like.

The term "alkylene" or "alkylenyl" refers to an alkyl moiety where the moiety contains two binding sites. The alkylene group may be straight (e.g., —(CH₂)—, —(CH₂)₂—, —(CH₂)₃—, or branched (e.g., —CH(CH₃)—, —C(CH₃)₂—, —CH₂CH(CH₃)—, —CH(CH₃)—CH₂—, —C(CH₃)₂—CH₂—, etc.). Suitable alkylene moieties are the same as those described above for alkyl except with two binding sites instead of just one.

The term "alkenylene" or "alkenylenyl" refers to an alkenyl moiety containing two binding sites. For example, —CH₂—CH=CH—CH₂—, —CH=CH—CH=CH—, and the like. Suitable alkenylene moieties are the same as those described above for alkenyl except with two binding sites instead of just one.

The term "alkynylene" or "alkynylenyl" refers to an alkynyl moiety containing two binding sites. For example, —CH₂—C≡C—CH₂—. Suitable alkynylene moieties are the same as those described above for alkynyl except with two binding sites instead of just one.

The term "aryl" refers to aromatic moieties having a single (e.g., phenyl) or a fused ring system (e.g., naphthalene, anthracene, phenanthrene, etc.). A typical aryl group is a 6- to 14-membered aromatic carbocyclic ring(s). A fused aromatic ring system may also include a phenyl fused to a partially or fully saturated cycloalkyl. For example, 2,3-dihydroindenyl, 1,2,3,4-tetrahydronaphthalenyl, 1,2-dihydronaphthalenyl, 2,3-dihydronaphthalenyl, 9,10-dihydroanthracenyl, fluorenyl, and the like.

The term "arylene" refers to a carbocyclic aromatic moiety having two binding sites. Suitable arylenes include those groups described above for an aryl moiety except with two binding sites rather than one. For example, 1,2-phenylene, 1,3-phenylene, 1,4-phenylene, 1,3-naphthylene, 1,4-naphthylene, 1,5-naphthylene, 1,6-naphthylene, 1,7-naphthylene, 2,3-naphthylene, 2,4-napthylene, 2,5-naphthylene, 2,6-naphthylene, 2,7-naphthylene, 3,4-naphthylene, 3,5-naphthylene, 3,6-naphthylene, 3,7-naphthylene, etc. The two binding sites on the fused arylene system may be on the same ring or different rings.

The term "partially or fully saturated cycloalkyl" refers to a carbocyclic ring which is fully hydrogenated (e.g., cyclopropyl, cyclobutyl, cyclopentyl, cyclohexyl, cycloheptyl, cyclooctyl, etc.) or partially hydrogenated (e.g., cyclopropenyl, cyclobutenyl, cyclopentyl, cyclopenta-1,3-dienyl, cyclohexenyl, cyclohexa-1,3-dienyl, cyclohexa-1,4-dienyl, etc.). The carbocyclic ring may be a single ring (as described above), a bicyclic ring (e.g., octahydropentalenyl, bicyclo[1.1.1]pentanyl, bicyclo[2.1.1]hexanyl, bicyclo[2.1.1]hex-2-enyl, bicyclo[2.2.1]hept-2-enyl, bicyclo[2.2.1]heptanyl, bicyclo[2.2.2]octanyl, bicyclo[2.2.2]oct-2-enyl, bicyclo[2.2.2]octa-2,5-dienyl, etc.) or a spiral ring (e.g., spiro[2.2]pentanyl, etc.), and the like.

The term "partially or fully saturated cycloalkylene" refers to a carbocyclic ring having either no unsaturation in the ring (fully hydrogenated) or at least one unsaturation (partially hydrogenated) without being aromatic and contains two binding sites. Suitable ring systems include those described above for a partially or fully saturated cycloalkyl except having two bind sites instead of one. For example, 1,2-cyclopropyl, 1,2-cycloprop-1-enyl, 1,2-cyclobutyl, 1,3-cyclobutyl, 1,2-cyclobut-1-enyl, 3,4-cyclobut-1-enyl, 3,5-cyclopent-1-enyl, 1,4-cyclopenta-1,3-dienyl, 1,5-cyclopenta-1,3-dienyl, 1,2-cyclopenta-1,3-dienyl, 1,3-cyclopenta-1,3-dienyl, etc. The carbocyclic ring may be a single ring, a bicyclic ring, or a spiral ring where the two binding sites on the bicyclic ring and spiral ring may be on the same ring or different rings. See, e.g., the illustration below.

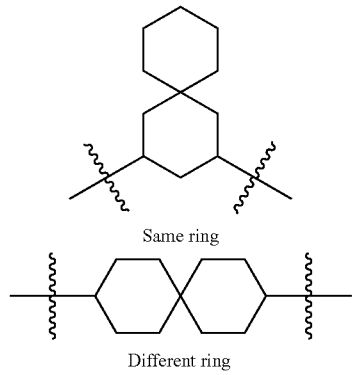

Same ring

Different ring

The term "partially or fully saturated heterocycle" refers to a nonaromatic ring that is either partially or fully hydrogenated and may exist as a single ring, bicyclic ring (including fused rings) or a spiral ring. Unless specified otherwise, the heterocyclic ring is generally a 3- to 12-membered ring containing 1 to 3 heteroatoms (preferably 1 or 2 heteroatoms) independently selected from sulfur, oxygen and/or nitrogen. Partially saturated or fully saturated heterocyclic rings include groups such as epoxy, aziridinyl, azetidinyl, tetrahydrofuranyl, dihydrofuranyl, dihydropyridinyl, pyrrolidinyl, imidazolidinyl, imidazolinyl, 1H-dihydroimidazolyl, hexahydropyrimidinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, oxazolidinyl, thiazolidinyl, octahydropyrrolo[3,2-b]pyrrolyl, and the like. A partially saturated heterocyclic ring also includes groups wherein the heterocyclic ring is fused to an aryl or heteroaryl ring (e.g., 2,3-dihydrobenzofuranyl, indolinyl (or 2,3-dihydroindolyl), 2,3-dihydrobenzothiophenyl, 2,3-dihydrobenzothiazolyl, 1,2,3,4-tetrahydroquinolinyl, 1,2,3,4-tetrahydroisoquinolinyl, 5,6,7,8-tetrahydropyrido[3,4-b]pyrazinyl, and the like). Examples of spiral rings include 2,6-diazaspiro[3.3]heptanyl, 3-azaspiro[5.5]undecanyl, 3,9-diazaspiro[5.5]undecanyl, and the like.

The term "partially or fully saturated heterocyclene" refers to a partially or fully saturated heterocyclic ring (as described above) except having two binding sites instead of one. The heterocyclene ring may be a single ring, a bicyclic ring, or a spiral ring where the two binding sites on the bicyclic ring and spiral ring may be on the same ring or different rings. See, e.g., the illustration below.

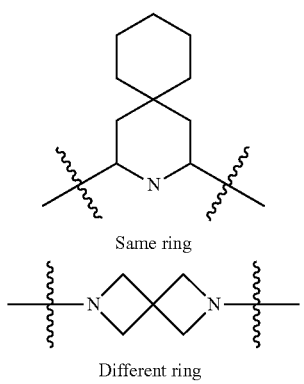

Same ring

Different ring

The term "heteroaryl" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, 1H-benzo[d][1,2,3]triazolyl, and the like.). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. The fused heteroaryl ring system may consist of two heteroaryl rings fused together or a hetereoaryl fused to an aryl (e.g., phenyl).

The term "heteroarylene" refers to a heteroaryl having two binding sites instead of one. Suitable heteroarylene groups include those described above for heteroaryl having two binding sites instead of one.

Unless specified otherwise, the term "compounds of the present invention" refers to compounds of Formula (I), (II) and (III), and salts thereof, as well as all stereoisomers (including diastereoisomers and enantiomers), rotamers, tautomers and isotopically labeled compounds (including deuterium substitutions), as well as inherently formed moieties (e.g., polymorphs, solvates and/or hydrates).

DETAILED DESCRIPTION

The present invention provides compounds and pharmaceutical formulations thereof that are useful in the treatment of diseases, conditions and/or disorders mediated or caused by the inhibition of apoptosis.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, N.Y. (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amino, or carboxyl groups) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). Suitable carboxyl protecting groups (C(O)O-Pg) include alkyl esters (e.g., methyl, ethyl or t-butyl), benzyl esters, silyl esters, and the like. The need for such protection is readily determined by one skilled in the art. For a general description of protecting groups and their use, see T. W. Greene, Protective Groups in Organic Synthesis, John Wiley & Sons, New York, 1991.

Scheme 1 (below) describes a potential route for producing compounds of formula M-L-M' by reacting starting material (SM-1) with a coupling site-containing amino acid moiety (SM-2), which may also include a protecting group at C", to form the amide intermediate (Ia). After removal of the amino-protecting group, intermediate (Ia) can then be reacted with starting material (SM-3) to form the diamide Intermediate (1b), which is equivalent to monomer M or M' having a coupling site (C"). Intermediate (Ib) may then be reacted with a linker (SM-4) to form a compound of the present invention (M-L-M') where C and C' are complementary reactive groups with the coupling site (C") such that a bond is formed between the monomeric unit and the linker. If C" contains a protecting group, then the protecting group is removed prior to reacting with SM-4. For example, an amino group (C") on the monomeric units reacting with an acid chloride (C and C') to form two amide bonds to form the linking group —NH—C(O)—X—C(O)—NH—. Groups A, D, A¹, Q, n, W, Lg, X, and L are as defined earlier. Those of skill in the art will appreciate that additional protecting groups may be needed depending upon the remote functionalities used in the various starting materials and intermediates (e.g., when $R^2$ is hydrogen). Each of the reactions shown in Scheme 1 below can be carried out under conditions known to those of skill in the art. For a more detailed description of the conditions see the example section below.

Scheme 1

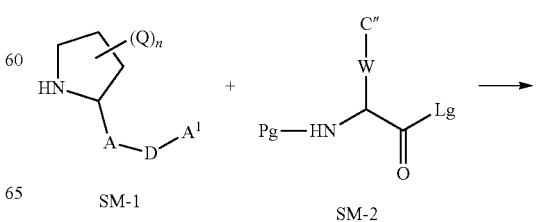

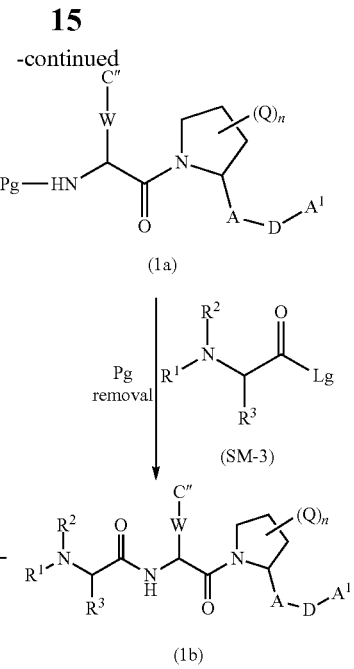

Lg = leaving group

Where the monomers M and M' are the same, the compound of formula M-L-M' may be obtained by the general Scheme 1 shown above. When the monomers M and M' are different, the starting material (SM-1) contains groups A, D, A¹, Q or n that are different and/or the starting material (SM-2) contains groups W or C" that are different for the synthesis of either M or M'. In other words, two different monomeric intermediates (1b) are reacted with the linker compound (SM-4). The various combinations of monomeric units can be controlled by using protecting groups at the different coupling sites to direct the desired combinations.

Various SM-2 compounds may be used in the preparation of the compounds of the present invention to provide different W moieties, such as amino substituted (NHR) alpha-amino acid compounds, amino-substituted (NH₂) alpha-amino acid compounds, and carboxyl-substituted alpha-amino acids. The binding sites on W (C") may or may not include a protecting group which can be removed prior to coupling to the linker compound.

Suitable amino substituted (NHR) alpha-amino acid compounds (which may be modified to include a protecting group) include 2,2-diaminoacetic acid, (S)-2-amino-2-(piperidin-4-yl)acetic acid, 3-(2-amino-2-carboxyethyl)pyrrolidine-1-carboxylic acid, (S)-2-amino-3-(aminooxy)propanoic acid, 2-amino-2-(piperidin-2-yl)acetic acid, (S)-2-amino-4-((R)-2,2-dimethyloxazolidin-5-yl)butanoic acid, (S)-2-amino-3-((S)-aziridin-2-yl)propanoic acid, (S)-2-amino-3-((S)-pyrrolidin-3-yl)propanoic acid, (S)-2-amino-3-(1H-indol-3-yl)propanoic acid, (S)-2-amino-2-(azetidin-3-yl)acetic acid, (S)-2-amino-6-(methylamino)hexanoic acid, 2-amino-3-(indolin-7-yl)propanoic acid, (S)-2-amino-4-(aminooxy)butanoic acid, (S)-methyl 2-amino-3-(1H-imidazol-5-yl)propanoic acid, (2S)-2-amino-3-(indolin-3-yl)propanoic acid, (S)-2-amino-2-(1H-pyrrol-3-yl)acetic acid, 2-amino-3-(piperidin-3-yl)propanoic acid, (S)-2-amino-3-(4-(aminooxymethyl)-phenyl)propanoic acid, 2-amino-2-(pyrrolidin-2-yl)acetic acid, 2-amino-3-(piperidin-2-yl)propanoic acid, (S)-2-amino-3-((S)-1,2,3,4-tetrahydroisoquinolin-3-yl)propanoic acid, 2-amino-2-(pyrrolidin-3-yl)acetic acid, 2-amino-3-(piperidin-4-yl)propanoic acid, 2-amino-3-(5,6,7,8-tetrahydropyrido[3,4-b]pyrazin-7-yl)propanoic acid, (S)-2-amino-3-((S)-azetidin-2-yl)propanoic acid, (S)-2-amino-3-(piperazin-1-yl)propanoic acid, (S)-2-amino-6-(cyclohexylamino)hexanoic acid, (S)-2-amino-3-(azetidin-3-yl)propanoic acid, 2-amino-3-(1-aminopyrrolidin-2-yl)propanoic acid, (S)-3-(4-(1H-imidazol-2-yl)phenyl)-2-aminopropanoic acid, (S)-2-amino-5-(aminooxy)pentanoic acid, (S)-2-amino-3-(2-(aminooxy)acetamido)-propanoic acid, (R)-2-amino-6-(benzylamino)hexanoic acid, (S)-2-amino-3-(1H-imidazol-5-yl)-propanoic acid, (E)-2-amino-4-(piperidin-4-yl)but-3-enoic acid, (S)-2-amino-3-(4-(isopropylaminomethyl)-phenyl)propanoic acid, (S)-2-amino-3-((S)-2,3-dihydro-1H-pyrrol-2-yl)propanoic acid, (S)-2-amino-4-(piperidin-4-yl)butanoic acid, 2-amino-3-(4-(piperazin-1-yl)phenyl)propanoic acid, (S)-2-amino-3-((S)-pyrrolidin-2-yl)propanoic acid, (S)-2-amino-4-(piperazin-1-yl)butanoic acid, 2-amino-3-(2-(piperazin-1-yl)phenyl)propanoic acid, (S)-2-amino-2-((S)-piperidin-3-yl)acetic acid, (S)-2-amino-6-(isopropylamino)hexanoic acid, 2-amino-3-(4-(tert-butyldimethylsilyloxy)pyrrolidin-2-yl)propanoic acid, and (S)-2-amino-4-(2-(aminooxy)acetamido)butanoic acid.

Suitable amino-substituted (NH₂) alpha-amino acid compounds (which may be modified to include a protecting group) include (R)-2,3-diaminopropanoic acid, (S)-2-amino-3-(2-amino-1H-imidazol-4-yl)propanoic acid, (S)-2-amino-4-(2-aminopyrimidin-4-yl)butanoic acid, (2R,3R)-2,3-diaminobutanoic acid, (2S,3R)-2-amino-3-(2-aminoacetoxy)butanoic acid, (2R,5R)-2,5-diamino-6,6,6-trifluorohexanoic acid, (S)-2,4-diaminobutanoic acid, (S)-2-amino-3-(2-aminophenyl)propanoic acid, 2-amino-3-(4-(aminomethyl)cyclohexyl)propanoic acid, (S)-2,5-diaminopentanoic acid, (R)-2-amino-3-(3-aminophenyl)propanoic acid, (S)-2-amino-4-(2-aminophenyl)-4-oxobutanoic acid, (R)-2-amino-4-(aminooxy)butanoic acid, (S)-2-amino-3-(4-aminophenyl)propanoic acid, 2-amino-3-(2-amino-5-chlorophenyl)propanoic acid, (E)-2,6-diaminohex-4-enoic acid, 2-amino-3-(2-aminopyridin-3-yl)propanoic acid, 2-amino-3-(2-amino-1H-indol-3-yl)propanoic acid, (R)-2,6-diaminohexanoic acid, 2-amino-3-(4-aminopyridin-3-yl)propanoic acid, 2-amino-3-(5-amino-1H-indol-3-yl)propanoic acid, (S)-2-amino-3-(2-aminoethoxy)propanoic acid, 2-amino-3-(6-amino-9H-purin-9-yl)propanoic acid, (S,E)-2-amino-4-(2-aminoethoxy)but-3-enoic acid, (S)-2,6-diamino-5,5-difluorohexanoic acid, (2S)-2-amino-5-(2-amino-5-methyl-4-oxo-4,5-dihydro-1H-imidazol-1-yl)pentanoic acid, (S)-2,7-diaminoheptanoic acid, 2-amino-3-(2-aminopyrimidin-5-yl)propanoic acid, 2-amino-3-(3-aminonaphthalen-2-yl)propanoic acid, 2,6-diamino-5-fluorohexanoic acid, (S)-2-amino-3-(2-(aminomethyl)-phenyl)propanoic acid, 2-amino-3-(4-amino-2,6-dichlorophenyl)-propanoic acid, (S)-2-amino-3-(2-aminoethoxy)propanoic acid, (S)-2-amino-3-(4-(aminomethyl)-phenyl)propanoic acid, 2-amino-4-(2-aminophenyl)-3-bromo-4-oxobutanoic acid, (S)-2-amino-2-(4-aminophenyl)acetic acid, (S)-2-amino-3-(3-(aminomethyl)-phenyl)propanoic acid, 2-amino-3-(2-amino-5-iodopyridin-3-yl)propanoic acid, and 2-amino-3-(4-amino-5-methylpyridin-3-yl)propanoic acid.

Suitable carboxyl-substituted alpha-amino acids (which may be modified to include a protecting group) include (S)-2-aminosuccinic acid, (R)-2-aminooctanedioic acid, (2S,4S)-2-amino-4-(pyridin-3-ylmethyl)-pentanedioic acid, (2R,3R)-2-amino-3-methylsuccinic acid, (1S,3S)-3-((S)-amino(carboxy)methyl)-2,2-difluorocyclopropane-carboxylic acid, (2S,4S)-2-amino-4-(pyridin-4-ylmethyl)pentanedioic acid, (S)-2-aminopentanedioic acid, (S)-4-(amino(carboxy)methyl)benzoic acid, (2S,4R)-2-amino-4-(thiophen-2-ylmethyl)pentanedioic acid, (2R)-2-amino-3-fluorosuccinic acid, 2-(amino(carboxy)-methyl)benzoic acid, (2S,4S)-2-amino-4-benzylpentanedioic acid, (1S,2S)-2-((S)-amino(carboxy)methyl)cyclopropanecarboxylic acid, (2R,4R)-2-amino-4-((tetrahydro-2H-pyran-4-yl)methyl)pentanedioic acid, (2S,3S)-2-amino-3-methylpentanedioic acid, (2S,4S)-2-amino-4-butylpentanedioic acid, (S)-3-(2-amino-2-carboxyethyl)-1H-indole-4-carboxylic acid, (S)-2-aminohexanedioic acid, (2S,4S)-2-amino-4-isobutylpentanedioic acid, (S)-2-(2-amino-2-carboxyethyl)-2H-indazole-6-carboxylic acid, (2S,4S)-2-amino-4-methylpentanedioic acid, (R)-4-(amino(carboxy)-methyl)-3-methylbenzoic acid, (2S,4S)-2-amino-4-(4-methylbenzyl)pentanedioic acid, (2S)-2-amino-4-fluoropentanedioic acid, (S)-4-(2-amino-2-carboxyethyl)benzoic acid, (2R,3R)-2-amino-3-(4-chlorophenyl)pentanedioic acid, (S)-4-amino-2,2-dimethylpentanedioic acid, (S)-3-(2-amino-2-carboxyethyl)benzoic acid, (S)-4-(4-amino-4-carboxybutanoyloxy)benzoic acid, (S)-2-aminoheptanedioic acid, 5-(amino(carboxy)methyl)-4-methylthiophene-2-carboxylic acid, (2S,4S)-2-amino-4-(4-methoxybenzyl)pentanedioic acid, 2-aminoheptanedioic acid, (R)-2-amino-6-(2-carboxyethylamino)hexanoic acid, (2S,4S)-2-amino-4-(naphthalen-2-ylmethyl)-pentanedioic acid, 4-amino-2,2-difluoropentanedioic acid, (S)-2-amino-4-(3-carboxypropanoyloxy)butanoic acid, (2S,4S)-2-amino-4-(4-(trifluoromethyl)-benzyl)pentanedioic acid, (S)-2-aminopentanedioic acid, (2S,4S)-2-amino-4-(furan-2-ylmethyl)pentanedioic acid, (2S,4S)-2-amino-4-(4-bromobenzyl)pentanedioic acid, (R)-3-(amino(carboxy)methyl)bicyclo[1.1.1]pentane-1-carboxylic acid, 3-(amino(carboxy)methyl)-1,2,2-trimethylcyclopentanecarboxylic acid, (S)-2-((3-(2-amino-2-carboxyethyl)-2,6-dioxo-2,3-dihydropyrimidin-1(6H)-yl)methyl)benzoic acid, (2S,4S)-2-amino-4-benzylpentanedioic acid, (2S,3R)-2-((S)-amino(carboxy)methyl)-3-phenylcyclopropanecarboxylic acid, and (S)-2-((3-(2-amino-2-carboxyethyl)-5-iodo-2,6-dioxo-2,3-dihydropyrimidin-1(6H)-yl)methyl)benzoic acid.

A variety of different linker compounds, C—X—C' (SM-4), may be used in the preparation of the compounds of the present invention, including but not limited to dicarboxylic acid chloride compounds, disulphonyl chloride compounds, and diamines.

Suitable dicarboxylic acid chloride compounds include oxalyl dichloride, pyridine-2,4-dicarbonyl dichloride, (2E,2'E)-3,3'-(1,4-phenylene)bis-2-propenoyl chloride, malonyl dichloride, pyrazine-2,3-dicarbonyl dichloride, dodecanedioyl dichloride, fumaroyl dichloride, 1-methyl-1H-pyrazole-3,4-dicarbonyl dichloride, cyclohexane-1,4-diylbis(methylene)dicarbonochloridate, succinyl dichloride, thiophene-2,5-dicarbonyl dichloride, (3R,6R)-hexahydrofuro[3,2-b]furan-3,6-diyl dicarbonochloridate, bis(chlorocarbonyl)methylamine, (E)-oct-4-enedioyl dichloride, 2,2'-(ethane-1,2-diylbis(oxy))bis(ethane-2,1-diyl) dicarbonochloridate, 2,2-dimethylmalonyl dichloride, cyclohexane-1,4-dicarbonyl dichloride, 2,2,3,3,4,4-hexafluoropentanedioyl dichloride, glutaroyl dichloride, octanedioyl dichloride, biphenyl-2,2'-dicarbonyl dichloride, 2,2'-oxydiacetyl chloride, butane-1,4-diyl dicarbonochloridate, biphenyl-4,4'-dicarbonyl dichloride, cyclobutane-1,2-dicarbonyl dichloride, 2-bromoterephthaloyl dichloride, adipoyl dichloride, (1R,2S,3S,4S)-bicyclo[2.2.1]hept-5-ene-2,3-dicarbonyl dichloride, 4-bromoisophthaloyl dichloride, ethane-1,2-diyl dicarbonochloridate, (1R,3S,4S)-bicyclo[2.2.1]hept-5-ene-2,3-dicarbonyl dichloride, 1-benzyl-1H-pyrazole-3,5-dicarbonyl dichloride, 1H-pyrazole-3,5-dicarbonyl dichloride, 4-methylthiazole-2,5-dicarbonyl dichloride, 4,4'-oxydibenzoyl chloride, 1H-pyrazole-4,5-dicarbonyl dichloride, nonanedioyl dichloride, 2,3-diphenylfumaroyl dichloride, 1H-1,2,3-triazole-4,5-dicarbonyl dichloride, 2,2,3,3-tetrafluorosuccinyl dichloride, (E)-4,4'-(diazene-1,2-diyl)dibenzoyl chloride, 2,2-diethylmalonyl dichloride, 2,2'-oxybis(ethane-2,1-diyl)dicarbonochloridate, 2,2,3,3,4,4,5,5-octafluorohexanedioyl dichloride, 3-methylhexanedioyl dichloride, 4-methoxyisophthaloyl dichloride, 2,3,5,6-tetrachloroterephthaloyl dichloride, 2,2-dimethylpentanedioyl dichloride, (E)-2,2'-(diazene-1,2-diyl)dibutanoyl chloride, (E)-2,2'-(diazene-1,2-diyl)dibenzoyl chloride, heptanedioyl dichloride, decanedioyl dichloride, 4,4'-(propane-2,2-diyl)bis(4,1-phenylene)dicarbonochloridate, isophthaloyl dichloride, 1H-indole-3,5-dicarbonyl dichloride, 4,5-dibromophthaloyl dichloride, terephthaloyl dichloride, hexane-1,6-diyl dicarbonochloridate, 1,1'-binaphthyl-2,2'-dicarbonyl dichloride, phthaloyl dichloride, 2-benzylsuccinyl dichloride, 4,4'-(cyclohexane-1,4-diyl)bis(4,1-phenylene)dicarbonochloridate, pyridine-3,5-dicarbonyl dichloride, naphthalene-2,3-dicarbonyl dichloride, 5-amino-2,4,6-triiodoisophthaloyl dichloride, pyridine-2,6-dicarbonyl dichloride, naphthalene-2,6-dicarbonyl dichloride, pyridine-3,4-dicarbonyl dichloride, and 5-aminoisophthaloyl dichloride.

Alternatively, dicarboxylic acid compounds can be converted to their acid chloride equivalents by treating with the appropriate reagent (e.g., thionyl chloride, phosphorus trichloride or phosphorus pentachloride). The dicarboxylic acid compounds can also be modified by making the hydroxyl group of the carboxylic acid moieties a leaving group which can subsequently be displaced to create a link to the monomeric units. Suitable dicarboxylic acid compounds include 2,2'-(ethane-1,2-diylbis(oxy))diacetic acid, 2,2'-(2,2'-oxybis(ethane-2,1-diyl)bis(oxy))diacetic acid, 4,7,9,12-tetraoxapentadecane-1,15-dioic acid, 2,2'-(2,2'-(2,2'-oxybis(ethane-2,1-diyl)bis(oxy))bis(2,1-phenylene))bis(oxy)diacetic acid, and 2,2'-(2,2'-(2,2'-(ethane-1,2-diylbis(oxy))bis(ethane-2,1-diyl))bis(oxy)bis(2,1-phenylene))bis(oxy)diacetic acid.

Suitable disulphonyl chloride linkers include methanedisulfonyl dichloride, 2,3-dihydro-1H-indene-4,6-disulfonyl dichloride, biphenyl-4,4'-disulfonyl dichloride, pyrosulfuryl chloride, 5-chlorothiophene-2,4-disulfonyl dichloride, 9H-fluorene-2,7-disulfonyl dichloride, methylene disulfochloridate, 2,4,6-trimethylbenzene-1,3-disulfonyl dichloride, 4,4'-methylenedibenzene-1-sulfonyl chloride, butane-1,4-disulfonyl dichloride, 4-amino-6-chlorobenzene-1,3-disulfonyl dichloride, 4,4'-oxydibenzene-1-sulfonyl chloride, benzene-1,2-disulfonyl dichloride, naphthalene-2,7-disulfonyl dichloride, 9-oxo-9H-fluorene-2,7-disulfonyl dichloride, benzene-1,3-disulfonyl dichloride, naphthalene-2,6-disulfonyl dichloride, 9,10-dioxo-9,10-dihydroanthracene-2,7-disulfonyl dichloride, piperazine-1,4-disulfonyl dichloride, 4-chloro-6-hydroxybenzene-1,3-disulfonyl dichloride, 9,10-dioxo-9,10-dihydroanthracene-2,6-disulfonyl dichloride, 4-methylbenzene-1,3-disulfonyl dichloride, 5-chloro-4-hydroxybenzene-1,3-disulfonyl dichloride, 2,2'-oxybis(1,1,2,2-tetrafluoroethanesulfonyl chloride), 2,4-dimethylbenzene-1,3-disulfonyl dichloride, 2,4,5,6-tetramethylbenzene-1,3-disulfonyl dichloride, 3,3'-sulfonyldibenzene-1-sulfonyl chloride, 4,4'-(2-(bromomethyl)oxazole-4,5-diyl)dibenzene-1-sulfonyl chloride, 4,6-dimethoxybenzene-1,3-disulfonyl dichloride, 4,4'-disulfanediyldibenzene-1-sulfonyl chloride, 4,5-dichlorobenzene-1,3-disulfonyl dichloride, and 4,4'-(2-methyloxazole-4,5-diyl)dibenzene-1-sulfonyl chloride.

Suitable diamino compounds which are commercially available or readily prepared from literature preparations include 2,6-diazaspiro[3.3]heptane; 2,2-dimethylpropane-1, 3-diamine; 4,7,10,13,16-pentaoxanonadecane-1,19-diamine; 3,3'-oxydipropan-1-amine; 2,2'-(ethane-1,2-diylbis (oxy))diethanamine; 3,3'-(2,2'-oxybis(ethane-2,1-diyl)bis (oxy))dipropan-1-amine; 2,2'-(2,2'-oxybis(ethane-2,1-diyl) bis(oxy))diethanamine; 2,3'-(ethane-1,2-diylbis(oxy)) dipropan-1-amine; propane-1,3-diamine; butane-1,4-diamine; 4-[2-(4-aminophenyl)ethynyl]aniline; 1,4-bis(3-aminophenyl)butadiyne; 1,4-diamino-2-butyne; hex-3-yne-2,5-diamine; hexa-2,4-diyne-1,6-diamine (see, e.g., Jeon, J. H.; Sayre, L. M., *Biochem. Biophys. Res. Commun.* 2003, 304(4), 788-794); $N^1,N^4$-diethylbut-2-yne-1,4-diamine; (E)-$N^1,N^4$-diethylbut-2-ene-1,4-diamine; 7cis-octahydro-pyrrolo[3,4-c]pyridine; 1,1'-ethylenedipiperazine; 1,5-diethyl-3,7-diaza-bicyclo[3.3.1]nonan-9-one; 1-ethyl-5-methyl-3,7-diaza-bicyclo[3.3.1]nonan-9-ol; 1-ethyl-5-methyl-3,7-diaza-bicyclo[3.3.1]nonan-9-one; 4,10-diaza-12-crown-4-ether; 1,5,9-triazacyclododecane; 1,5-dimethyl-3,7-diaza-bicyclo [3.3.1]nonan-9-ol; 4,4-bipiperidine; 1,5-dimethyl-3,7-diaza-bicyclo[3.3.1]nonan-9-one; 1,5-dimethyl-3,7-diazabicyclo [3.3.1]nonane; 2,8-diazaspiro[5,5]undecane; decahydro-2,7-naphthyridine; 1,4,7-triazacyclononane; 6,6-dimethyl-1,4-diazepane; (S)-2,7-diazaspiro[4.4]nonane; cis-octahydro-pyrrolo[3,4-c]pyridine; 1,5-diazacyclooctane; 6-methyl-[1, 4]diazepane; 3,7-diazabicyclo[3.3.0]octane; homopiperazine; 2,6-diazaspiro[3.3]heptane; piperazine; (3a5,7aR)-octahydro-pyrrolo[2,3-c]p; (3aR,7aS)-octahydro-pyrrolo[2,3-c]p; 1-(furan-2-yl)-N-(piperidin-4-ylmethyl) methanamine; 2,2,2-trifluoro-N-(pyrrolidin-3-ylmethyl) ethanamine; N-((morpholin-2-yl)methyl)ethanamine; methyl-morpholin-2-ylmethyl-amine; methyl-piperidin-4-ylmethyl-amine; ethyl-pyrrolidin-3-ylmethyl-amine; methyl-pyrrolidin-3-ylmethyl-amine; N-methyl-3-azetidinemethanamine; and (2,3-dihydro-1H-pyrrolo[2,3-b]pyridin-5-yl)methanamine. Those of skill in the art will know how to make modifications to the literature preparations or commercial compounds to make additional derivatives.

The dimeric compounds may be isolated and used as the compound per se or as its salt. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfornate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes various isotopically labeled compounds as defined herein, for example those into which radioactive isotopes, such as $^3$H, $^{13}$C, and $^{14}$C, are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life, reduced dosage requirements, reduced cyp inhibition (competitive or time dependent) or an improvement in therapeutic index. For example, substitution with deuterium may modulate undesirable side effects of the undeuterated compound, such as competitive cyp inhibition, time dependent cyp inactivation, etc. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

It will be recognized by those skilled in the art that the compounds of the present invention may contain chiral centers and as such may exist in different isomeric forms. As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound.

"Enantiomers" are a pair of stereoisomers that are non-superimposable mirror images of each other. A 1:1 mixture of a pair of enantiomers is a "racemic" mixture. The term is used to designate a racemic mixture where appropriate.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)— or (S)—.

Unless specified otherwise, the compounds of the present invention are meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of the invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

Compounds of the present invention have been found to induce or enhance apoptosis and therefore useful in the treatment of cancer. Consequently, a compound of the present invention may be used in the manufacture of a medicament for the treatment of diseases, conditions or disorders associated with the overexpression of an IAP in a subject (or mammal, preferably a human), inducing apoptosis in a tumor or cancer cell, inhibiting the binding of an IAP protein to a caspase protein, or sensitizing a tumor or cancer cell to an apoptotic signal. In the process, a compound of the present invention may also induce the degradation of individual or multiple IAPs in cells (specifically cIAP1, cIAP2 and/or XIAP), and may induce expression of TNFα in some cells.

The compounds of the present invention are typically used as a pharmaceutical composition (e.g., a compound of the present invention and at least one pharmaceutically acceptable carrier). As used herein, the term "pharmaceutically acceptable carrier" includes generally recognized as safe (GRAS) solvents, dispersion media, surfactants, antioxidants, preservatives (e.g., antibacterial agents, antifungal agents), isotonic agents, salts, preservatives, drug stabilizers, buffering agents (e.g., maleic acid, tartaric acid, lactic acid, citric acid, acetic acid, sodium bicarbonate, sodium phosphate, and the like), and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated. For purposes of this invention, solvates and hydrates are considered pharmaceutical compositions comprising a compound of the present invention and a solvent (i.e., solvate) or water (i.e., hydrate).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical composition comprising a therapeutically effective amount of a compound of the present invention is generally formulated for use as a parenteral administration. The pharmaceutical compositions (e.g., intravenous (iv) formulation) can be subjected to conventional pharmaceutical operations such as sterilization and/or can contain conventional inert diluents, or buffering agents, as well as adjuvants, such as preservatives, stabilizers, wetting agents, emulsifers and buffers well known to those of skill in the art.

In certain instances, it may be advantageous to administer the compound of the present invention in combination with at least one additional pharmaceutical (or therapeutic) agent (e.g., an anti-cancer agent or adjunct therapy typically used in chemotherapy). The compound of the present invention may be administered either simultaneously with, or before or after, one or more other therapeutic agent(s). Alternatively, the compound of the present invention may be administered separately, by the same or different route of administration, or together in the same pharmaceutical composition as the other agent(s).

Suitable additional anti-cancer agents include (i) Taxane anti-neoplastic agents such as Cabazitaxel (1-hydroxy-7β,10β-dimethoxy-9-oxo-5β,20-epoxytax-11-ene-2α,4,13α-triyl-4-acetate-2-benzoate-13-[(2R,3S)-3-{[(tert-butoxy)carbonyl]amino}-2-hydroxy-3-phenylpropanoate), larotaxel ((2α,3ξ,4α,5β,7α,10β,13α)-4,10-bis (acetyloxy)-13-({(2R,3S)-3-[(tent-butoxycarbonyl)amino]-2-hydroxy-3-phenylpropanoyl}oxy)-1-hydroxy-9-oxo-5,20-epoxy-7,19-cyclotax-11-en-2-yl benzoate) and paclitaxel;

(ii) Vascular Endothelial Growth Factor (VEGF) receptor inhibitors and antibodies such as Bevacizumab (sold under the trademark Avastin® by Genentech/Roche), axitinib, (N-methyl-2-[[3-[(E)-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide, and described in POT Publication No. WO 021066470), pasireotide (also known as SOM230, and described in PCT Publication No. WO 02/010192), and sorafenib (sold under the tradename Nexavar®);

(iii) Tyrosine kinase inhibitors such as Erlotinib hydrochloride (sold under the trademark Tarceva® by Genentech/ Roche), Linifanib (N-[4-(3-amino-1H-indazol-4-yl)phenyl]-N'-(2-fluoro-5-methylphenyl)urea, also known as ABT 869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996), dasatinib (sold under the tradename Sprycel® by Bristol-Myers Squibb), armala (also known as pazopanib, sold under the tradename Votrient® by GlaxoSmithKline), and imatinib and imatinib mesylate (sold under the tradenames Gilvec® and Gleevec® by Novartis);

(iv) Bcr/Abl kinase inhibitors such as nilotinib hydrochloride (sold under the tradename Tasigna® by Novartis);

(v) DNA Synthesis inhibitors such as Capecitabine (sold under the trademark Xeloda® by Roche), gemcitabine hydrochloride (sold under the trademark Gemzar® by Eli Lilly and Company), and nelarabine ((2R,3S,4R,5R)-2-(2-amino-6-methoxy-purin-9-yl)-5-(hydroxymethyl)oxolane-3,4-diol, sold under the tradenames Arranon® and Atriance® by GlaxoSmithKline);

(vi) Antineoplastic agents such as oxaliplatin (sold under the tradename Eloxatin® ay Sanofi-Aventis and described in U.S. Pat. No. 4,169,846);

(vii) Epidermal growth factor receptor (EGFR) inhibitors such as Gefitnib (sold under the tradename Iressa®), N-[4-[(3-Chloro-4-fluorophenyl)amino]-7-[[(3"S")-tetrahydro-3-furanyl]oxy]-6-quinazolinyl]-4(dimethylamino)-2-butenamide, sold under the tradename Tovok® by Boehringer Ingelheim), cetuximab (sold under the tradename Erbitux® by Bristol-Myers Squibb), and panitumumab (sold under the tradename Vectibix® by Amgen);

(viii) Pro-apoptotic receptor agonists (PARAs) such as Dulanermin (also known as AMG-951, available from Amgen/Genentech);

(ix) PI3K inhibitors such as 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730), and 2-Methyl-2-[4-[3-methyl-2-oxo-8-(quinolin-3-yl)-2,3-dihydroimidazo[4,5-c]quinolin-1-yl]phenyl] propionitrile (also known as BEZ 235 or NVP-BEZ 235, and described in PCT Publication No. WO 06/122806);

(x) BCL-2 inhibitors such as 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]-sulfonyl] benzamide (also known as ABT-263 and described in PCT Publication No. WO 09/155386);

(xi) Topoisomerase I inhibitors such as Irinotecan (sold under the trademark Camptosar® by Pfizer), topotecan hydrochloride (sold under the tradename Hycamtin® by GlaxoSmithKline);

(xii) Topoisomerase II inhibitors such as etoposide (also known as VP-16 and Etoposide phosphate, sold under the tradenames Toposar®, VePesid® and Etopophos®), and teniposide (also known as VM-26, sold under the tradename Vumon®);

(xiii) CTLA-4 inhibitors such as Tremelimumab (IgG2 monoclonal antibody available from Pfizer, formerly known as ticilimumab, CP-675,206), and ipilimumab (CTLA-4 antibody, also known as MDX-010, CAS No. 477202-00-9);

(xiv) Histone deacetylase inhibitors (HDI) such as Vorinostat (sold under the tradename Zolinza® by Merck) and Panobinostat (N-hydroxy-3-[4-[[[2-(2-methyl-1H-indol-3- yl)ethyl]amino]methyl]phenyl]-(2E)-2-Propenamide described in PCT Publication No. 02/0022577 or U.S. Pat. No. 7,067,551);

(xv) Alkylating agents such as Temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), and thiotepa (also known as thiophosphoamide, TESPA and TSPA, sold under the tradename Thioplex®;

(xvi) Anti-tumor antibiotics such as doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), and mitomycin C (sold under the tradename Mutamycin®);

(xvii) Anti-mitotic agents such as Docetaxel (sold under the tradename Taxotere® by Sanofi-Aventis);

(xviii) Proteasome inhibitors such as Bortezomib (sold under the tradename Velcade®);

(xix) Plant Alkaloids such as Paclitaxel protein-bound (sold under the tradename Abraxane®), vinblastine (also known as vinblastine sulfate, vincaleukoblastine and VLB, sold under the tradenames Alkaban-AQ® and Velban®), vincristine (also known as vincristine sulfate, LCR, and VCR, sold under the tradenames Oncovin® and Vincasar Pfs®), vinorelbine (sold under the tradename Navelbine®), and paclitaxel (sold under the tradenames Taxol and Onxal™);

(xx) Glucocorticosteroids such as Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S, 9R,10S,11S,13S,14S,16R,17R)-9-fluoro-11,17-dihydroxy-17-(2-hydroxyacetyl)-10,13,16-trimethyl-6,7,8,9,10,11,12, 13,14,15,16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), and methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®);

(xxi) Tumor necrosis factor-related apoptosis-inducing ligand (TRAIL, also referred to as Apo2 Ligand) receptor agonists such as TRAIL antibodies (e.g., Adecatumumab, Belimumab, Cixutumumab, Conatumumab, Figitumumab, Iratumumab, Lexatumumab, Lucatumumab, Mapatumumab, Necitumumab, Ofatumumab, Olaratumab, Panitumumab, Pritumumab, Pritumumab, Robatumumab, Votumumab, Zalutumumab, and TRAIL (referred to as anti-DR-5) antibodies described in U.S. Pat. No. 7,229,617 and PCT Publication No. WO2008/066854, incorporated herein by reference), and recombinant TRAIL (e.g., Dulanermin (also known as AMG 951 (rhApo2L/TRAIL)); and (xxii) Tumor-vascular disrupting agents such as Vadimezan (5,6-dimethyl-9-oxo-9H-Xanthene-4-acetic acid described in U.S. Pat. No. 5,281,620).

A preferred anti-cancer agent for use in combination with a compound of the present invention is paclitaxel.

Another preferred anti-cancer agent for use in combination with a compound of the present invention is a PI3K inhibitor (e.g., 2-Methyl-2-[4-[3-methyl-2-oxo-8-(quinolin-3-yl)-2,3-dihydroimidazo[4,5-c]quinolin-1-yl]phenyl]propionitrile).

Another preferred anti-cancer agent for use in combination with a compound of the present invention is a TRAIL (or anti-DR-5) antibody or recombinant TRAIL.

Suitable therapeutic agents for adjunct therapy include steroids, anti-inflammatory agents, anti-histamines, anti-emetics, and other agents well-known to those of skill in art for use in improving the quality of care for patients being treated for the diseases, conditions, or disorders described herein.

The compound of the present invention or pharmaceutical composition thereof for use in humans is typically administered intravenously via infusion at a therapeutic dose of less than or equal to about 100 mg/kg, 75 mg/kg, 50 mg/kg, 25 mg/kg, 10 mg/kg, 7.5 mg/kg, 5.0 mg/kg, 3.0 mg/kg, 1.0 mg/kg, 0.5 mg/kg, 0.05 mg/kg or 0.01 mg/kg, but preferably not less than about 0.0001 mg/kg. The dosage may depend upon the infusion rate at which the formulation is administered. In general, the therapeutically effective dosage of a compound, the pharmaceutical composition, or the combinations thereof, is dependent on the species of the subject, the body weight, age and individual condition, the disorder or disease or the severity thereof being treated. A physician, pharmacist, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations.

In general, a therapeutically effective amount of a compound of the present invention is administered to a patient in need of treatment. The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

In one non-limiting embodiment, the term "a therapeutically effective amount" refers to the amount of a compound of the present invention, when administered to a subject, is effective to (1) at least partially alleviate, inhibit, prevent and/or ameliorate a condition, a disorder or a disease mediated by IAP, or characterized by normal or abnormal activity of such IAP mediation or action; or (2) enhance programmed cancerous cell death (apoptosis). Preferably, when administered to a cancer cell, or a tissue, or a non-cellular biological material, or a medium, the compound of the present invention is effective to at least partially increase or enhance apoptosis. Not to be bound by any particular mechanism, a compound of the present may inhibit the binding of IAP protein to a caspase protein and/or may initiate degradation of XIAP, cIAP1 and/or cIAP2, directly or indirectly.

In one embodiment, a method for inhibiting the binding of an IAP protein to a caspase protein is provided which comprises contacting the IAP protein with a compound of the present invention.

In another embodiment, a method of inducing apoptosis in a tumor or cancer cell is provided which comprises introducing into the cell, a compound of the present invention.

In yet another embodiment, a method of sensitizing a tumor or cancer cell to an apoptotic signal is provided which comprises introducing into the cell a compound of the present invention.

In yet another embodiment, a method for treating a disease, disorder, or condition associated with the overexpression of an IAP in a mammal, is provided which comprises administering to the mammal an effective amount of a compound of the present invention.

In yet another embodiment, a method for treating cancer in a mammal is provided which comprises administering to a mammal in need of such treatment an effective amount of a compound of the present invention. A particularly useful method is the treatment of breast cancer.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. Preferably, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder, refers (i) to ameliorating the disease or disorder (i.e., slowing or arresting or reducing the development of the disease or at least one of the clinical symptoms thereof); (ii) to alleviating or ameliorating at least one physical parameter including those which may not be discernible by the patient; or (iii) to preventing or delaying the onset or development or progression of the disease or disorder. In general, the term "treating" or "treatment" describes the management and care of a patient for the purpose of combating the disease, condition, or disorder and includes the administration of a compound of the present invention to prevent the onset of the symptoms or complications, alleviating the symptoms or complications, or eliminating the disease, condition or disorder.

As used herein, a subject is "in need of" a treatment if such subject would benefit biologically, medically or in quality of life from such treatment (preferably, a human).

Another aspect of the invention is a product comprising a compound of the present invention and at least one other therapeutic agent (or pharmaceutical agent) as a combined preparation for simultaneous, separate or sequential use in therapy to enhance apoptosis.

In the combination therapies of the invention, the compound of the present invention and the other therapeutic agent may be manufactured and/or formulated by the same or different manufacturers. Moreover, the compound of the present invention and the other therapeutic (or pharmaceutical agent) may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of the present invention for treating a disease or condition by inhibiting IAPs (or enhancing apoptosis), wherein the medicament is prepared for administration with another therapeutic agent. The invention also provides for the use of another therapeutic agent, wherein the medicament is administered as a combination of a compound of the present invention with the other therapeutic agent.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

The preparation of (4-fluoro-phenyl)-((S)-5-pyrrolidin-2-yl-pyridin-3-yl)-methanone is described in Example 2 (Step 5) of PCT Publication No. WO 08/016893.

Example 1

Preparation of Heptanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide} (1A)

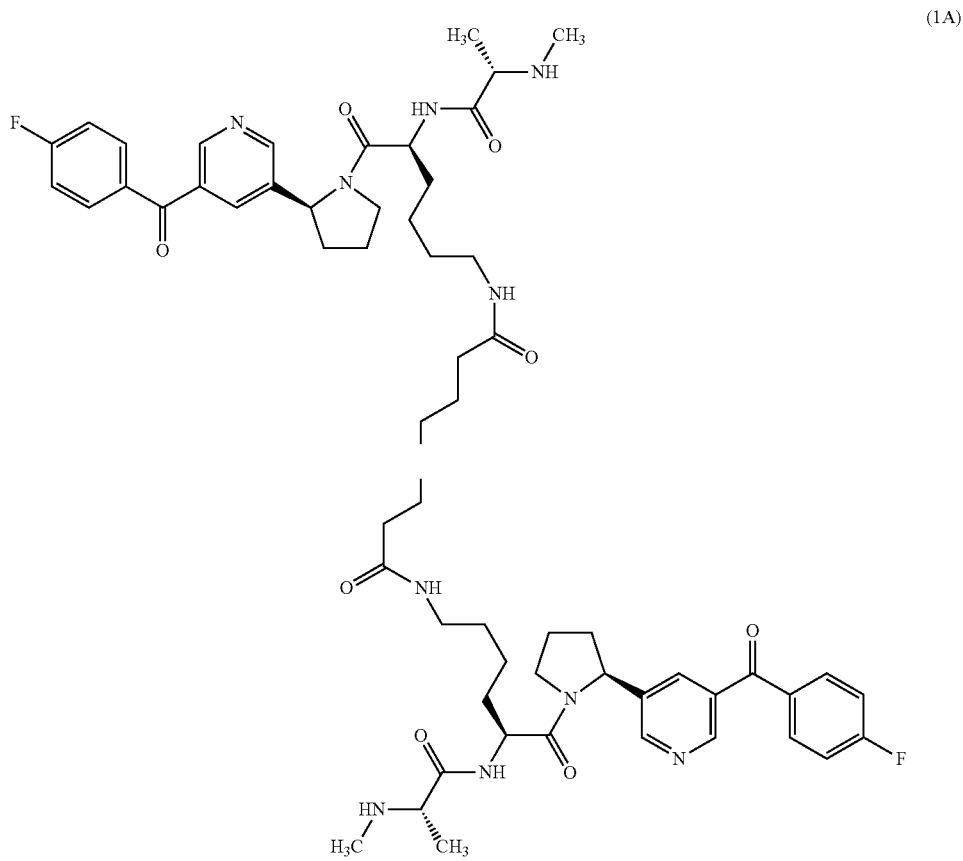

(1A)

Step 1: Preparation of Intermediate ((S)-5-tert-butoxycarbonylamino-6-{(S)-2-[5-(4-fluoro-benzoyl)-pyridin-3-yl]-pyrrolidin-1-yl}-6-oxo-hexyl)-carbamic acid 9H-fluoren-9-ylmethyl ester (I-1a)

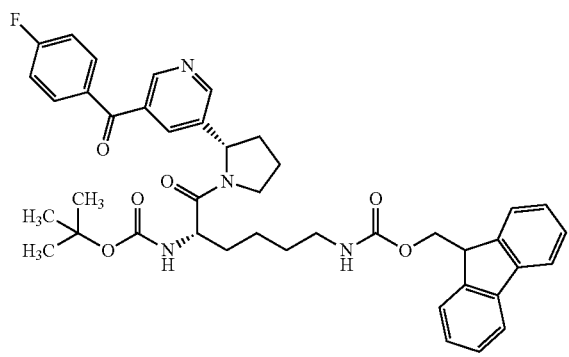

(I-1a)

To a solution of (4-fluoro-phenyl)-((S)-5-pyrrolidin-2-yl-pyridin-3-yl)-methanone (1.0 g, 3.7 mmol), (S)-2-tert-butoxycarbonylamino-6-(9H-fluoren-9-ylmethoxycarbonylamino)-hexanoic acid (2.0 g, 4.4 mmol) and ethyldiisopropylamine (3 mL) in DMF (20 mL) was added a solution of 2-(1H-benzo[d][1,2,3]triazol-1-yl)-1,1,3,3-tetramethylisouronium hexafluorophosphate (V) (1.67 g, 4.4 mmol) and 1H-benzo[d][1,2,3]triazol-1-ol (0.6 g, 4.4 mmol) in DMF (10 mL) and the mixture was shaken for 16 hours. The reaction mixture was diluted with ethyl acetate (300 mL), washed sequentially with brine (2×) (300 mL), saturated aqueous bicarbonate solution (300 mL), brine (300 mL), water (300 mL), and brine (300 mL), then dried over $Na_2SO_4$/$MgSO_4$, and concentrated in vacuo to provide crude ((S)-5-tert-butoxycarbonylamino-6-{(S)-2-[5-(4-fluoro-benzoyl)-pyridin-3-yl]pyrrolidin-1-yl}-6-oxo-hexyl)-carbamic acid 9H-fluoren-9-ylmethyl ester as a light yellow foam.

MS (ESI) m/e 721.6 (M+H$^+$); HPLC (Novapak 150×3.9 mm C18 column: mobile phase: 35-90% acetonitrile/water with 0.1% TFA, at 2 mL/minute over 5 minutes) t 3.655 minutes. The crude compound was carried forward to the next step without purification.

Step 2: Preparation of Intermediate ((S)-5-amino-6-{(S)-2-[5-(4-fluoro-benzoyl)-pyridin-3-yl]-pyrrolidin-1-yl}-6-oxo-hexyl)-carbamic acid 9H-fluoren-9-ylmethyl ester (I-1b)

(I-1b)

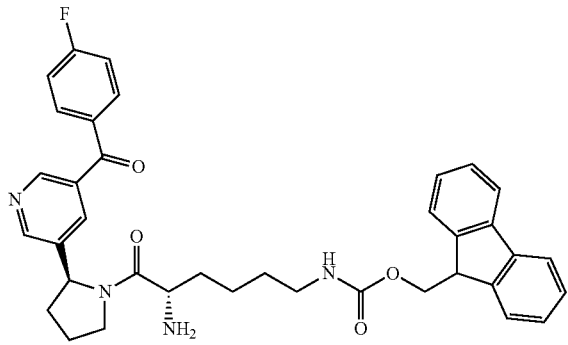

To a solution of ((S)-5-tert-butoxycarbonylamino-6-{(S)-2-[5-(4-fluoro-benzoyl)-pyridin-3-yl]-pyrrolidin-1-yl}-6-oxo-hexyl)-carbamic acid 9H-fluoren-9-ylmethyl ester (I-1a) in dichloromethane (15 mL) was added trifluoroacetic acid (5 mL). After stirring for 45 minutes, the reaction mixture was concentrated in vacuo to afford crude ((S)-5-amino-6-{(S)-2-[5-(4-fluoro-benzoyl)-pyridin-3-yl]pyrrolidin-1-yl}-6-oxo-hexyl)-carbamic acid 9H-fluoren-9-ylmethyl ester as a dark amber residue.

MS (ESI) m/e 621.5 (M+H$^+$); HPLC (Novapak 150×3.9 mm C18 column: mobile phase: 35-90% acetonitrile/water with 0.1% TFA, at 2 mL/minute over 5 minutes.) t 2.297 minutes. The crude compound was carried forward to the next step without purification.

Step 3: Preparation of Intermediate ((S)-5-[(S)-2-(tert-butoxycarbonyl-methyl-amino)-propionylamino]-6-{(S)-2-[5-(4-fluoro-benzoyl)-pyridin-3-yl]-pyrrolidin-1-yl}-6-oxo-hexyl)-carbamic acid 9H-fluoren-9-ylmethyl ester (I-1c)

(I-1c)

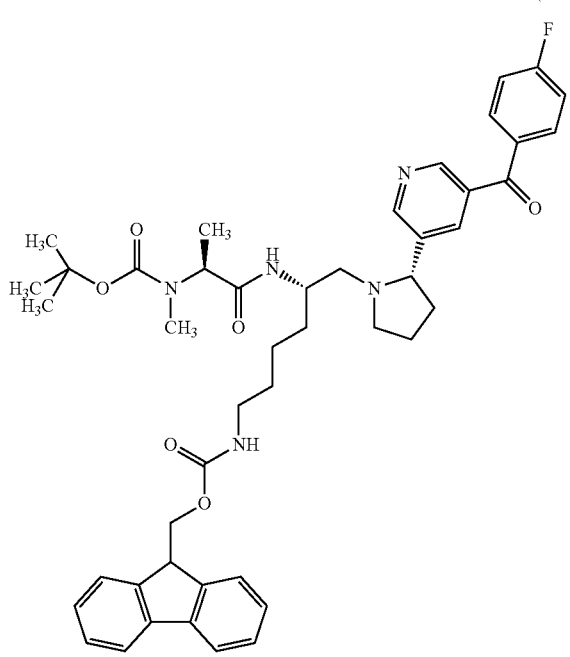

To a solution of 3((S)-5-amino-6-{(S)-2-[5-(4-fluoro-benzoyl)-pyridin-3-yl]-pyrrolidin-1-yl}-6-oxo-hexyl)-carbamic acid 9H-fluoren-9-ylmethyl ester (I-1b: 2.3 g, 3.7 mmol), (S)-2-(tert-butoxycarbonyl-methyl-amino)-propionic acid (0.89 g, 4.4 mmol) and ethyldiisopropylamine (7 ml) in DMF (20 mL) was added a solution of 2-(1H-benzo[d][1,2,3]triazol-1-yl)-1,1,3,3-tetramethylisouronium hexafluorophosphate (V) (1.67 g, 4.4 mmol) and 1H-benzo[d][1,2,3]triazol-1-ol (0.6 g, 4.4 mmol) in DMF (10 mL) and the mixture shaken for 16 hours. The reaction mixture was diluted with ethyl acetate (300 mL), washed sequentially with brine (2×) (300 mL), saturated aqueous bicarbonate solution (300 mL), brine (300 mL), water (300 mL) and brine (300 mL), then dried over Na$_2$SO$_4$/MgSO$_4$, and concentrated in vacuo to provide crude ((S)-5-[(S)-2-(tert-butoxycarbonyl-methyl-amino)-propionylamino]-6-{(S)-2-[5-(4-fluoro-benzoyl)-pyridin-3-yl]-pyrrolidin-1-yl}-6-oxo-hexyl)-carbamic acid 9H-fluoren-9-ylmethyl ester as a light yellow foam.

MS (ESI) m/e 806.6 (M+H$^+$); HPLC (Novapak 150×3.9 mm C18 column: mobile phase: 35-90% acetonitrile/water with 0.1% TFA, at 2 mL/minute over 5 minutes.) t 3.669 minutes. The crude compound was carried forward to the next step without purification.

Step 4: Preparation of Intermediate [(S)-1-((S)-5-amino-1-{(S)-2-[5-(4-fluoro-benzoyl)-pyridin-3-yl]-pyrrolidine-1-carbonyl}-pentylcarbamoyl)-ethyl]-methyl-carbamic acid tert-butyl ester (I-1d)

(I-1d)

To ((S)-5-[(S)-2-(tert-butoxycarbonyl-methyl-amino)-propionylamino]-6-{(S)-2-[5-(4-fluoro-benzoyl)-pyridin-3-yl]-pyrrolidin-1-yl}-6-oxo-hexyl)-carbamic acid 9H-fluoren-9-ylmethyl ester (I-1c: 2.98 g, 3.7 mmol) was added 2M dimethylamine in THF (20 mL) and the mixture was stirred for 2 hours. The reaction mixture was concentrated in vacuo and purification was accomplished with semi-preparative reverse phase HPLC (300×50 mm) eluting w/10-60% acetonitrile/water over 45 minutes, followed by lyophilization of the desired fractions to provide [(S)-1-((S)-5-amino-1-{(S)-2-[5-(4-fluoro-benzoyl)-pyridin-3-yl]-pyrrolidine-1-carbonyl}-pentylcarbamoyl)-ethyl]-methyl-carbamic acid tert-butyl ester (1.5 g, 69% over 4 steps).

MS (ESI) m/e 584.5 (M+H$^+$); HPLC (Novapak 150×3.9 mm C18 column: mobile phase: 15-90% acetonitrile/water with 0.1% TFA, at 2 mL/minute over 5 minutes.) t 2.537 minutes.

Step 5: Preparation of Intermediate Compound (I-1e)

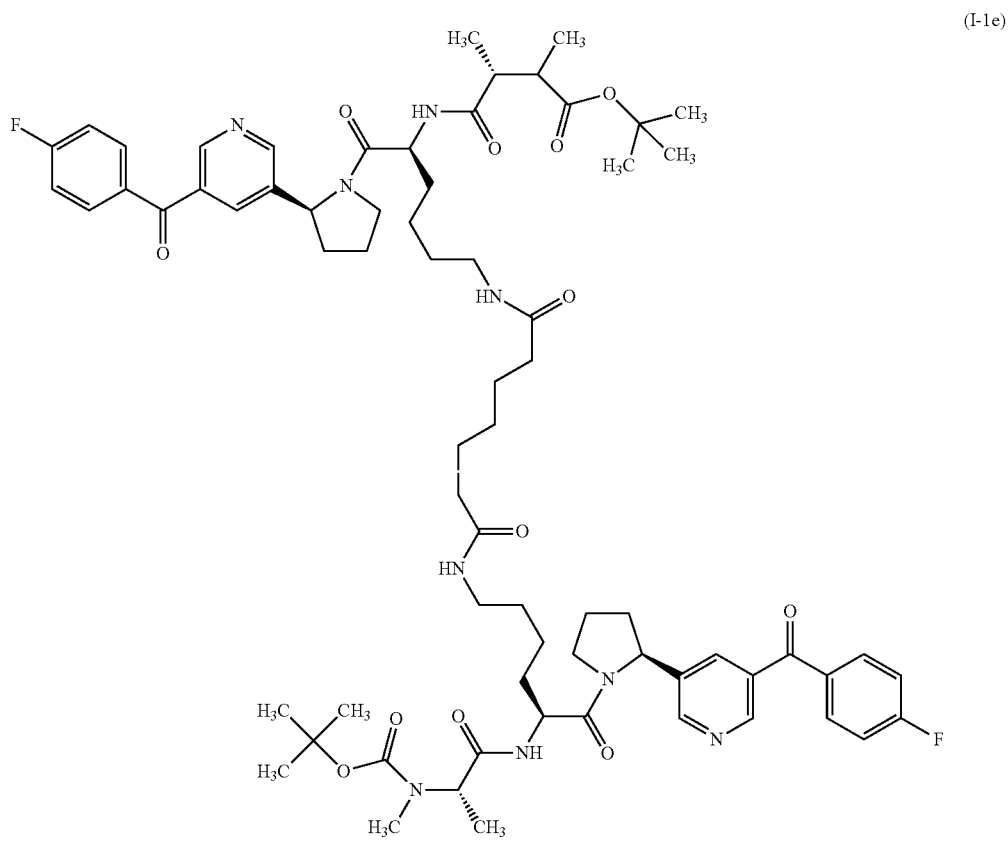 [SMILES: CC(C(=O)OC(C)(C)C)[C@@H](C)C(=O)N[C@@H](CCCCNC(=O)CCCCCC(=O)NCCCC[C@H](NC(=O)[C@H](C)N(C)C(=O)OC(C)(C)C)C(=O)N1CCC[C@H]1c1cncc(C(=O)c2ccc(F)cc2)c1)C(=O)N1CCC[C@H]1c1cncc(C(=O)c2ccc(F)cc2)c1]

(I-1e)

To a solution of [(S)-1-((S)-5-amino-1-{(S)-2-[5-(4-fluoro-benzoyl)-pyridin-3-yl]-pyrrolidine-1-carbonyl}-pentylcarbamoyl)-ethyl]-methyl-carbamic acid tert-butyl ester (I-1d: 0.150 g, 0.257 mmol), and ethyldiisopropylamine (0.066 g, 0.512 mmol) in DCM (5 mL) was added a solution of heptanedioyl dichloride (0.025 g, 0.128 mmol) in DCM (1 mL) and the mixture was shaken for 30 minutes. The reaction mixture was washed with saturated aqueous bicarbonate solution (100 mL), and concentrated in vacuo to provide crude title compound (I-1e).

MS (ESI) m/e 1292.2 (M+H$^+$); HPLC (Novapak 150×3.9 mm C18 column: mobile phase: 35-90% acetonitrile/water with 0.1% TFA, at 2 mL/minute over 5 minutes) t 2.729 minutes. The crude compound was carried forward to the next step without purification.

Final Step: Preparation of Heptanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide} (1A)

To a solution of Intermediate (I-1e: 35 mg, 0.025 mmol) in dichloromethane (4 mL) was added trifluoroacetic acid (2 mL) and the mixture was stirred for 30 minutes. The reaction mixture was concentrated in vacuo to afford a dark amber residue. Purification was accomplished by semi-preparative reverse phase HPLC (300×50 mm) eluting w/10-60% acetonitrile/water w/0.1% TFA modifier over 45 minutes. followed by lyophilization of the desired fractions providing the trifluoroacetate salt of Compound 1A (Example 1A-1). The material was neutralized by passing through a column of bicarbonate MP resin eluting sequentially with methanol (10 mL), then concentrated in vacuo to afford the free base of the title Compound (1A). This material was dissolved in ethyl acetate (10 mL) and methanol (0.5 mL) and treated with a saturated solution of citric acid in ethyl acetate (5.5 mL). The precipitate that resulted was filtered off under nitrogen and dried under vacuum, to provide the citric acid salt of Compound 1A (Example 1A-2: 21.8 mg, 15.6% over 3 steps).

$^1$H NMR (400 MHz, CD$_3$OD): δ 8.61-8.82 (m, 4.56, H), 7.81-8.11 (m, 6.74H), 7.20-7.37 (m, 4.19H), 7.02-7.16 (m, 0.91H), 5.31-5.44 (m, 1.02H), 5.12-5.23 (m, 2.01H), 4.62-4.73 (m, 1.91H), 4.22-4.36 (m, 1.01H), 3.94-4.05 (m, 1.90H), 3.75-3.94 (m, 3.92H), 3.59-3.75 (m, 1.37H), 3.44-3.54 (m, 0.65H), 3.04-3.25 (m, 4.37H), 2.70-2.90 (m, 10.17H), 2.60-2.70 (m, 4.46H), 2.54-2.60 (m, 0.55H), 2.38-2.54 (m, 2.96H), 1.74-2.23 (m, 12.54H), 1.28-1.74 (m, 19.81H); MS (ESI) m/e 1092.1 (M+H$^+$);

HPLC (Novapak 150×3.9 mm C18 column: mobile phase: 10-90% acetonitrile/water with 0.1% TFA, at 2 mL/minute over 5 minutes) t 2.645 minutes.

The compounds in Table 1A below were prepared using procedures analogous to those described above for the preparation of Example 1A, 1A-1 and 1A-2 with the appropriate starting materials.

TABLE 1A

| Example No. | |
|---|---|
| 1B | 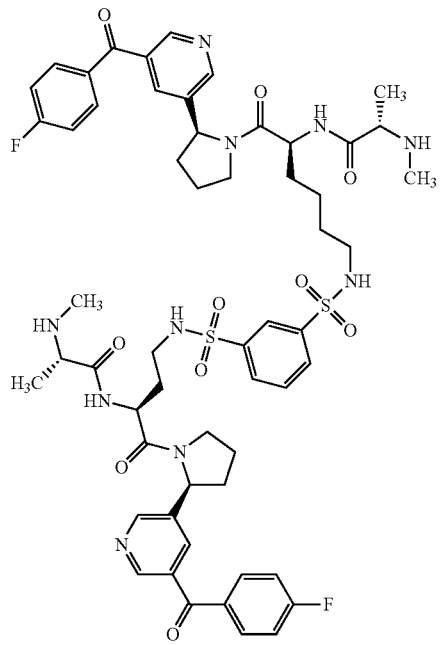 [SMILES: CN[C@@H](C)C(=O)N[C@@H](CCCCNS(=O)(=O)c1cccc(S(=O)(=O)NCC[C@H](NC(=O)[C@H](C)NC)C(=O)N2CCC[C@H]2c2cncc(C(=O)c3ccc(F)cc3)c2)c1)C(=O)N1CCC[C@H]1c1cncc(C(=O)c2ccc(F)cc2)c1] |

(S)-N-((S)-1-((S)-2-(5-(4-fluorobenzoyl)pyridin-3-yl)pyrrolidin-1-yl)-6-(3-(N-((S)-6-((S)-2-(5-(4-fluorobenzoyl)pyridin-3-yl)pyrrolidin-1-yl)-5-((S)-2-(methylamino)propanamido)-6-oxohexyl)sulfamoyl)phenylsulfonamido)-1-oxohexan-2-yl)-2-(methylamino)propanamide
MS (ESI) m/e 1167.7 (M + H$^+$);
Retention time = 2.733 (10-90% Acetonitrile/H$_2$O, 0.1% TFA) 2 mL/minute

| 1C | 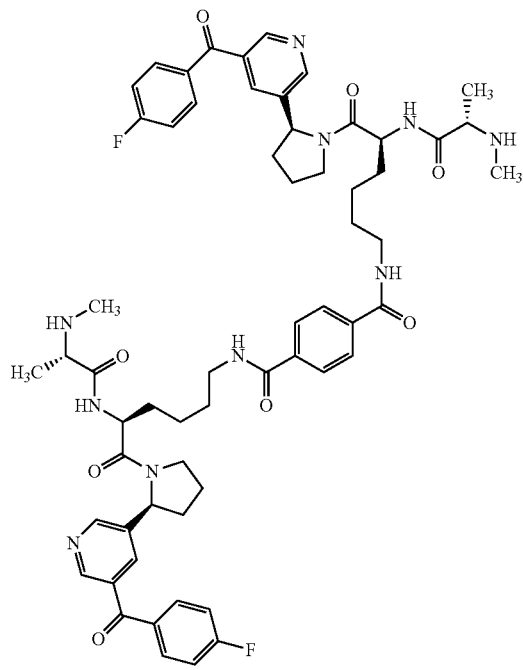 [SMILES: CN[C@@H](C)C(=O)N[C@@H](CCCCNC(=O)c1ccc(C(=O)NCCCC[C@H](NC(=O)[C@H](C)NC)C(=O)N2CCC[C@H]2c2cncc(C(=O)c3ccc(F)cc3)c2)cc1)C(=O)N1CCC[C@H]1c1cncc(C(=O)c2ccc(F)cc2)c1] |

N,N'-Bis-[(S)-6-{(S)-2-[5-(4-fluorobenzoyl)-pyridin-3-yl]-pyrrolidin-1-yl}-5-((S)-2-methylamino-propionylamino)-6-oxo-hexyl]-terephthalamide
MS (ESI) m/e 1098 (M + H$^+$);
Retention time = 4.31 (10-95% Acetonitrile/H$_2$O, 0.1% TFA) 1.5 mL/minute TABLE 1A-continued

| Example No. | |
|---|---|
| 1D | 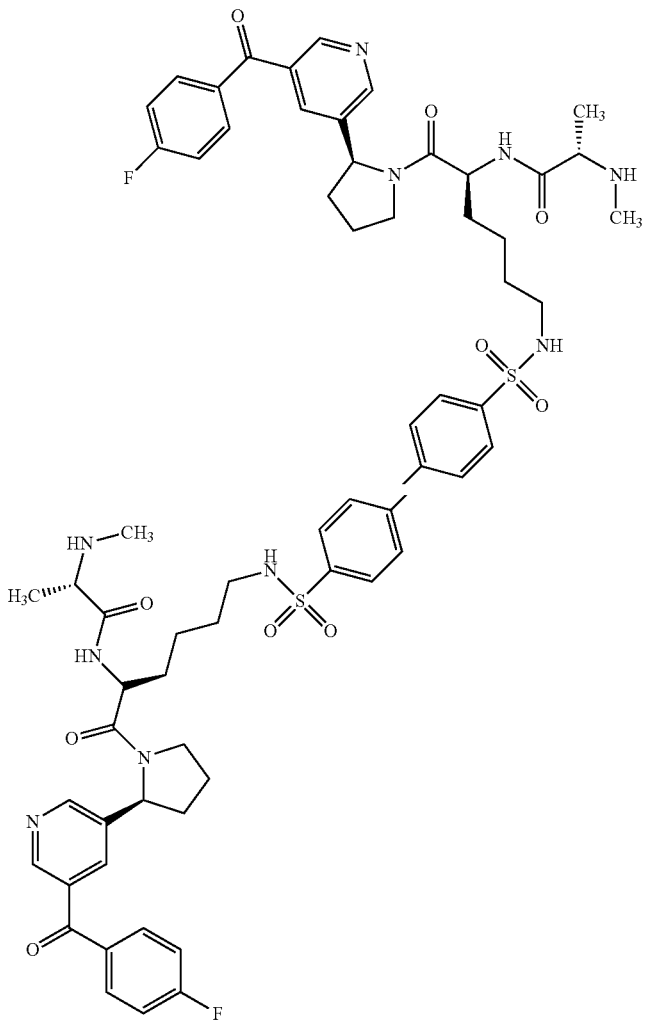 |

(S)-N-((S)-1-((S)-2-(5-(4-fluorobenzoyl)pyridin-3-yl)pyrrolidin-1-yl)-6-(4'-(N-((S)-6-((S)-2-(5-(4-fluorobenzoyl)pyridin-3-yl)pyrrolidin-1-yl)-5-((S)-2-(methylamino)propanamido)-6-oxohexyl)sulfamoyl)biphenyl-4-ylsulfonamido)-1-oxohexan-2-yl)-2-(methylamino)propanamide The citrate salt of the product was generated as a white solid (35 mg, yield 13.7% in three steps):

$^1$H NMR (400 MHz, CD$_3$OD): δ 8.59-8.84(m, 5.05 H), 8.00-8.09(m, 0.94 H), 7.78-7.99(m, 12.62 H), 7.59-7.76(m, 1.40 H), 7.20-7.35 (m, 4.31 H), 5.33-5.45(m, 0.96 H), 5.10-5.31(m, 2.59 H), 4.63-4.73 (m, 2.15 H), 4.22-4.36(m, 1.12 H), 3.74-4.04(m, 6.09 H), 3.55-3.74 (m, 1.58 H), 3.44-3.52(m, 0.57 H), 3.03-3.16(m, 1.05 H), 2.85-2.98 (m, 3.54 H), 2.68-2.85(m, 8.38 H), 2.55-2.68(m, 5.11 H), 2.36-2.55 (m, 3.22 H), 2.03-2.16(m, 3.59 H), 1.73-1.99(m, 4.77 H), 1.30-1.71 (m, 15.07 H);

MS (ESI) m/e 1246.3 (M + H$^+$);

HPLC (Novapak 150 × 3.9 mm C18 column: mobile phase: 10-90% acetonitrile/water with 0.1% TFA, at 2 mL/minute over 5 minutes) t 2.838 minutes TABLE 1A-continued

| Example No. | |
|---|---|
| 1E | 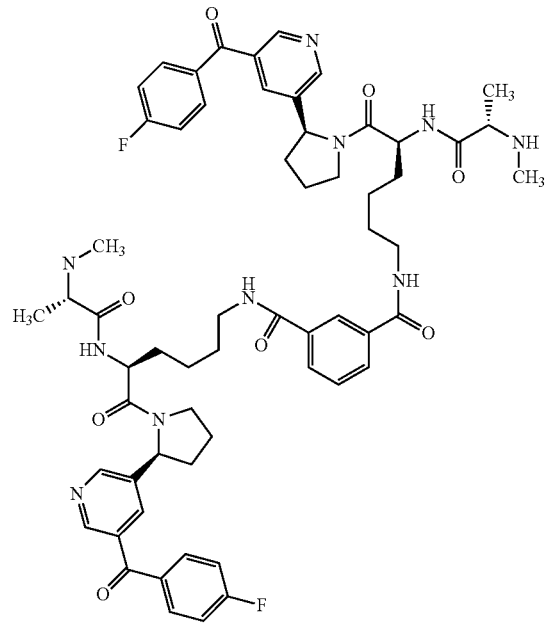 [SMILES: CN[C@@H](C)C(=O)N[C@@H](CCCCNC(=O)c1cccc(C(=O)NCCCC[C@H](NC(=O)[C@H](C)NC)C(=O)N2CCC[C@H]2c2cncc(C(=O)c3ccc(F)cc3)c2)c1)C(=O)N1CCC[C@H]1c1cncc(C(=O)c2ccc(F)cc2)c1]<br>N,N'-Bis-[(S)-6-{(S)-2-[5-(4-fluoro-benzoyl)-pyridin-3-yl]-pyrrolidin-1-y}-5-((S)-2-methylamino-propionylamino)-6-oxo-hexyl]-isophthalamide<br>The citrate salt of the product was generated as a white solid (6.6 mg, yield 4.7% in three steps):<br>$^1$H NMR (400 MHz, CD$_3$OD): δ 8.57-8.79(m, 4.49 H), 8.21-8.32(m, 1.50 H), 8.02-8.10(m, 0.84 H), 7.82-8.01(m, 6.90 H), 7.61-7.81(m, 1.60 H), 7.46-7.61(m, 1.84 H), 7.19-7.35(m, 4.03 H), 6.90-7.16(m, 1.86 H), 5.34-5.47(m, 1.00 H), 5.11-5.27(m, 2.07 H), 4.64-4.77(m, 2.01 H), 4.25-4.39(m, 1.08 H), 3.95-4.06(m, 1.71 H), 3.73-3.95(m, 3.77 H), 3.54-3.73(m, 1.50 H), 3.44-3.54(m, 1.56 H), 3.35-3.44(m, 2.89 H), 3.08-3.17(m, 0.74 H), 2.66-2.88(m, 9.70 H), 2.53-2.66(m, 4.24 H), 2.38-2.53(m, 2.66 H), 2.02-2.16(m, 3.11 H), 1.81-2.00(m, 3.87 H), 1.56-1.77(m, 5.08 H), 1.32-1.56(m, 7.93 H), 1.08-1.22(m, 1.34 H);<br>MS (ESI) m/e 1098.1 (M + H$^+$);<br>HPLC (Novapak 150 × 3.9 mm C18 column: mobile phase: 10-90% acetonitrile/water with 0.1% TFA, at 2 mL/minute over 5 minutes.) t 2.617 minutes. |
| 1F | 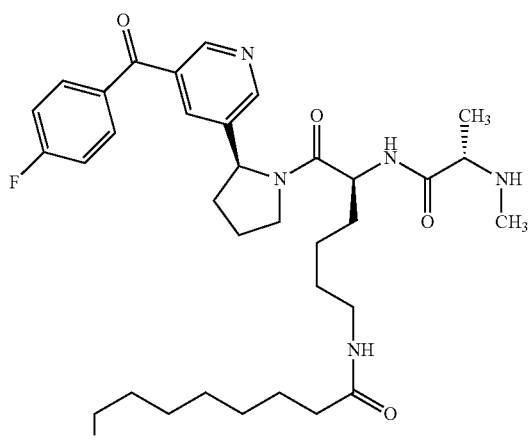 |

TABLE 1A-continued

Example No.

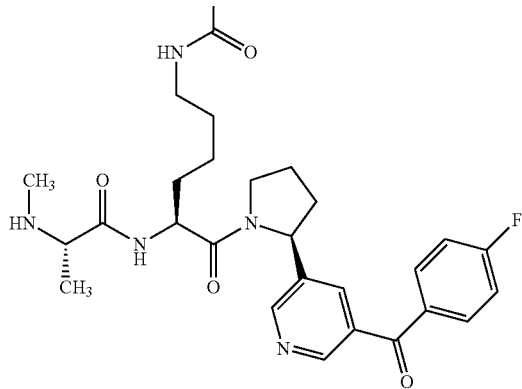

Nonanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide}

The citrate salt of the product was generated as a white solid (10.2 mg, yield 7.1% in three steps):

$^1$H NMR (400 MHz, CD$_3$OD): δ 8.59-8.82(m, 4.51 H), 8.02-8.09(m, 0.70 H), 7.84-8.02(m, 5.52 H), 7.60-7.81(m, 1.14 H), 7.43-7.60(m, 0.91 H), 7.22-7.37(m, 3.96 H), 7.03-7.15(m, 0.60 H), 6.75-6.83(m, 0.45 H), 5.31-5.44(m, 0.84 H), 5.12-5.29(m, 2.14 H), 4.62-4.74(m, 1.83 H), 4.22-4.37(m, 0.91 H), 3.94-4.05(m, 1.75 H), 3.75-3.94(m, 3.77 H), 3.55-3.74(m, 1.26 H), 3.41-3.55(m, 1.01 H), 3.05-3.26(m, 4.45 H), 2.70-2.87(m, 11.25 H), 2.54-2.69(m, 4.71 H), 2.37-2.54 (m, 2.84 H), 2.04-2.22(m, 6.83 H), 1.88-1.99(m, 2.19 H), 1.75-1.88 (m, 2.09 H), 1.27-1.72(m, 22.69 H), 1.13-1.21(m, 0.97 H);

MS (ESI) m/e 1120.3 (M + H$^+$);

HPLC (Novapak 150 × 3.9 mm C18 column: mobile phase: 10-90% acetonitrile/water with 0.1% TFA, at 2 mL/minute over 5 minutes.) t 2.695 minutes.

1G

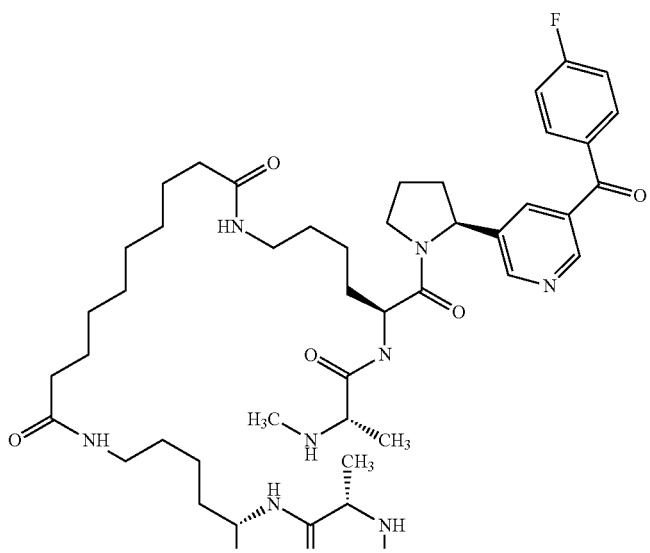

TABLE 1A-continued

| Example No. | |
|---|---|

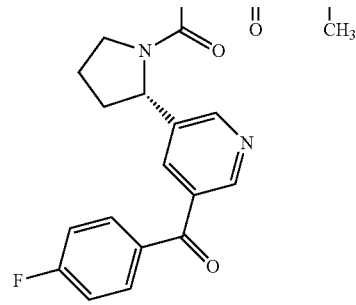

Decanedioic acid bis-{[(S)-6-{(S)-2-[5-(4-fluoro-benozyl)-pyridin-3-yl]-pyrrolidin-1-yl}-5-((S)-2-methylamino-propionylamino)-6-oxo-hexyl]-amide}

The citrate salt of the product was generated as a white solid (6.3 mg, yield 4.3% in three steps):

$^1$H NMR (400 MHz, CD$_3$OD): δ 8.63-8.82(m, 5.00 H), 8.02-8.09(m, 1.03 H), 7.83-8.01(m, 5.97 H), 7.26-7.38(m, 4.17 H), 6.94-7.19(m, 2.76 H), 5.30-5.42(m, 1.52H), 5.12-5.24(m, 2.47 H), 4.61-4.74(m, 2.26 H), 4.22-4.35(m, 1.39 H), 3.95-4.06(m, 2.04 H), 3.75-3.95(m, 4.18 H), 3.54-3.75(m, 2.38 H), 3.45-3.52(m, 0.97 H), 3.33-3.36(m, 1.55 H), 3.06-3.25(m, 4.57 H), 2.71-2.89(m, 11.85 H), 2.61-2.70 (m, 3.97 H), 2.39-2.55(m, 3.03 H), 1.75-2.21(m, 11.47 H), 1.18-1.71(m, 23.17 H);

MS (ESI) m/e 1134.2 (M + H$^+$);

HPLC (Novapak 150 × 3.9 mm C18 column: mobile phase: 10-90% acetonitrile/water with 0.1% TFA, at 2 mL/minute over 5 minutes.) t 2.751 minutes.

| 1H | |
|---|---|

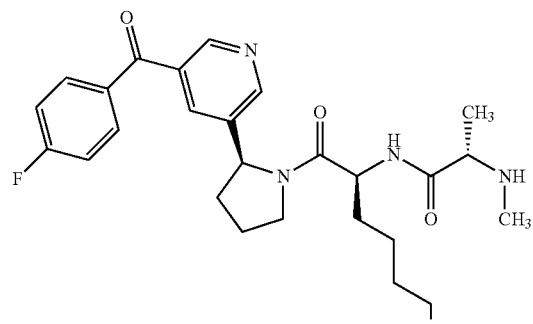

TABLE 1A-continued

Example No.

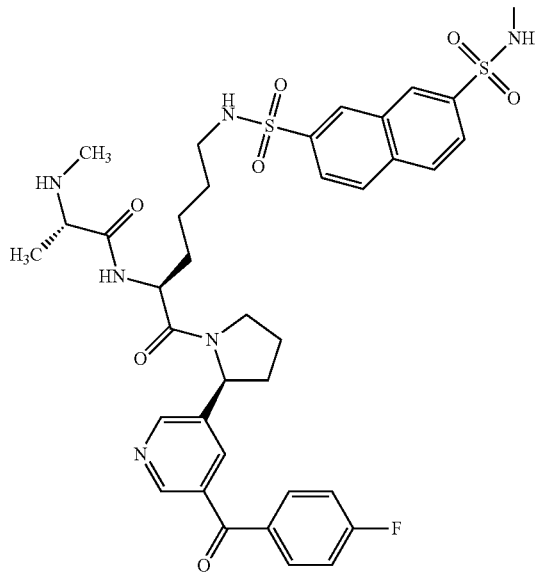

(S)-N-((S)-1-((S)-2-(5-(4-fluorobenzoyl)pyridin-3-yl)pyrrolidin-1-yl)-6-(7-(N-
((S)-6-((S)-2-(5-(4-fluorobenzoyl)pyridin-3-yl)pyrrolidin-1-yl)-5-((S)-2-
(methylamino)propanamido)-6-oxohexyl)sulfamoyl)naphthalene-2-
sulfonamido)-1-oxohexan-2-yl)-2-(methylamino)propanamide
MS (ESI) m/e 1220 (M + H$^+$);
Retention time = 2.821 (10-90% acetonitrile/H$_2$O, 0.1% TFA) 2 mL/minute

1I

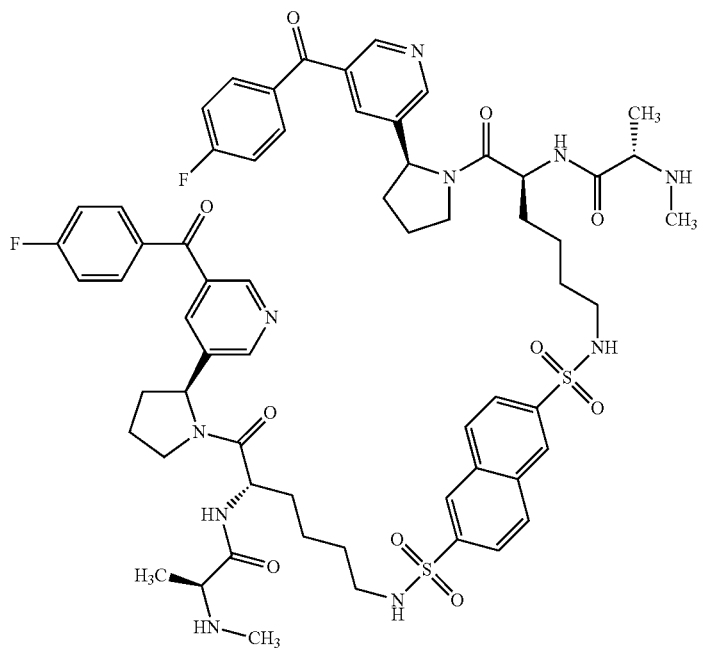 [SMILES: CN[C@@H](C)C(=O)N[C@@H](CCCCNS(=O)(=O)c1ccc2cc(S(=O)(=O)NCCCC[C@H](NC(=O)[C@H](C)NC)C(=O)N3CCC[C@H]3c3cncc(C(=O)c4ccc(F)cc4)c3)ccc2c1)C(=O)N1CCC[C@H]1c1cncc(C(=O)c2ccc(F)cc2)c1]

(S)-N-((S)-1-((S)-2-(5-(4-fluorobenzyl)pyridin-3-yl)pyrrolidin-1-yl)-6-(6-(N-
((S)-6-((S)-2-(5-(4-fluorobenzoyl)pyridin-3-yl)pyrrolidin-1-yl)-5-((S)-2-
(methylamino)propanamido)-6-oxohexyl)sulfamoyl)naphthalene-2-
sulfonamido)-1-oxohexan-2-yl)-2-(methylamino)propanamide
MS (ESI) m/e 1220 (M + H$^+$);
Retention time = 2.788 (10-90% acetonitrile/H$_2$O, 0.1% TFA) 2 mL/minute TABLE 1A-continued

| Example No. | |
|---|---|
| 1J | 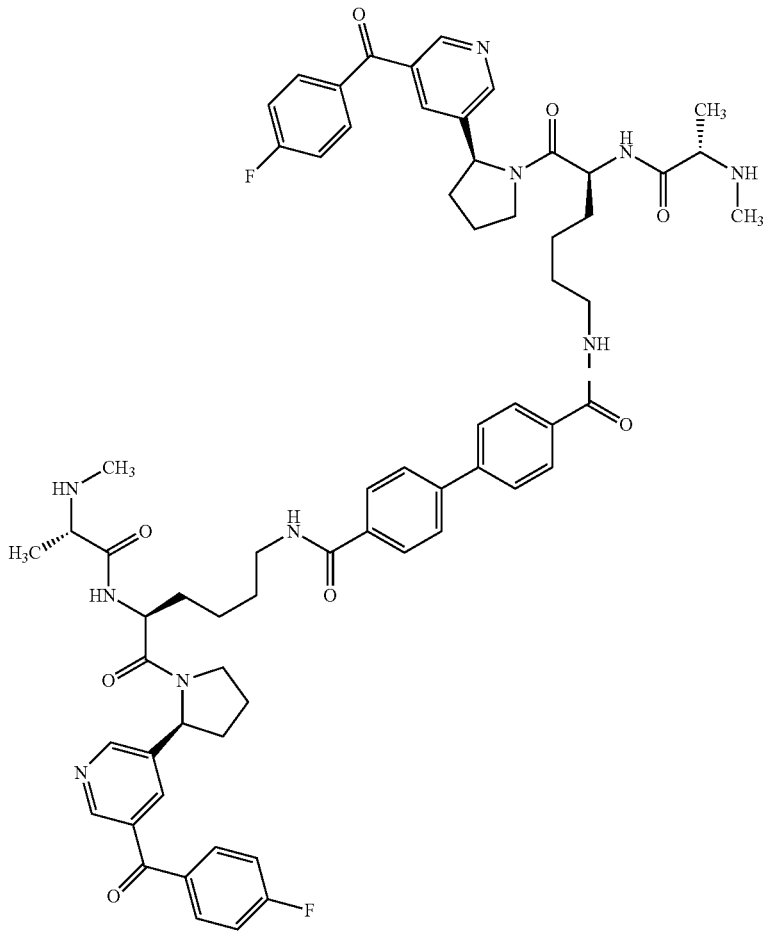 [SMILES: [2H]C([2H])([2H])N[C@@H](C)C(=O)N[C@@H](CCCCNC(=O)c1ccc(-c2ccc(C(=O)NCCCC[C@H](NC(=O)[C@H](C)NC)C(=O)N3CCC[C@H]3c3cncc(C(=O)c4ccc(F)cc4)c3)cc2)cc1)C(=O)N1CCC[C@H]1c1cncc(C(=O)c2ccc(F)cc2)c1] |

Biphenyl-4,4'-dicarboxylic acid bis-{[(S)-6-{(S)-2-[5-(4-fluorobenzoyl)-pyridin-3-yl]-pyrrolidin-1-yl}-5-((S)-2-methylamino-propionylamino)-6-oxo-hexyl]-amide}

The citrate salt of the product was generated as a white solid (2.25 g, yield 53% in three steps):

$^1$H NMR (400 MHz, CD$_3$OD): δ 1.3-1.57(m, 12.5 H), 1.57-1.80(m, 7.4 H), 1.80-2.01(m, 5.4 H), 2.01-2.14(m, 4.4 H), 2.38-2.52(m, 3.5 H), 3.10-3.15(m, 0.4 H), 3.36-3.45(m, 4.3 H), 3.45-3.55(m, 0.9 H), 3.6-3.7(m, 0.9 H), 3.74-3.84(m, 2.5 H), 3.85-3.94(m, 2H), 3.96-4.06(m, 1.9 H), 4.28-4.36(m, 0.4 H), 4.67-4.76(m, 2.2 H), 5.12-5.21(m, 1.9 H), 5.37-5.45(m, 0.4 H), 7.19-7.33(m, 4.7 H), 7.68-7.78(m, 4.8 H), 7.83-7.93(m, 9.5 H), 7.93-7.97(m, 1.9 H), 8.01-8.06(m, 0.4 H), 8.64-8.72(m, 4.2 H), 8.73-8.77(m, 0.4 H);

MS (ESI) m/e 1173.57 (M + H$^+$);

HPLC (Novapak 150 × 3.9 mm C18 column: mobile phase: 10-90% acetonitrile/water with 0.1% TFA, at 2 mL/minute over 5 minutes.) t 2.994 minutes.

TABLE 1A-continued
| Example No. | |
|---|---|
| 1K | 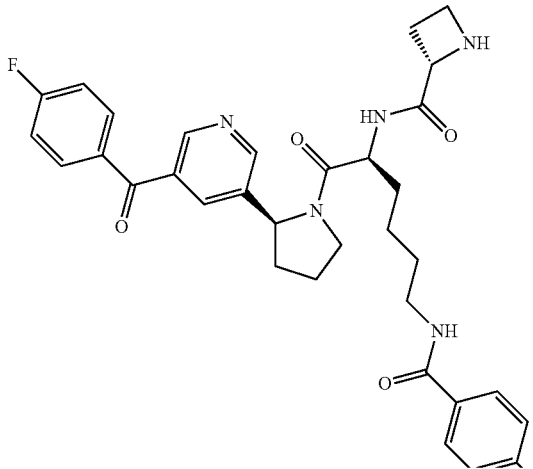<br><br>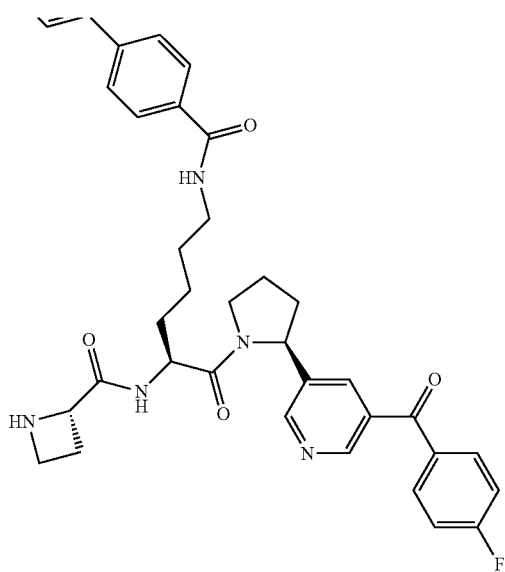<br><br>Biphenyl-4,4'-dicarboxylic acid bis-[((S)-5-[((S)-azetidine-2-carbonyl)-amino]-6-{(S)-2-[5-(4-fluoro-benzoyl)-pyridin-3-yl]-pyrrolidin-1-yl}-6-oxo-hexyl)-amide]<br>MS (ESI) m/e 1170.37 (M + H$^+$);<br>Retention time = 2.67 (10-90% acetonitrile/H$_2$O, 0.1% TFA) 2 mL/minute |

TABLE 1B

1L

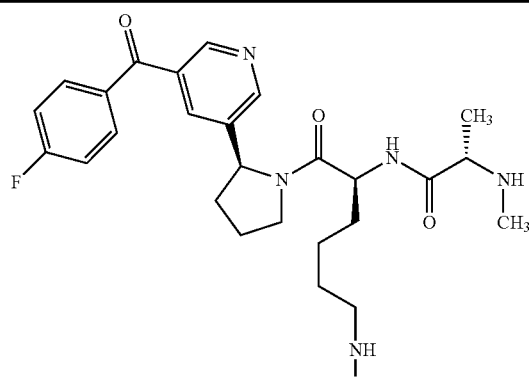

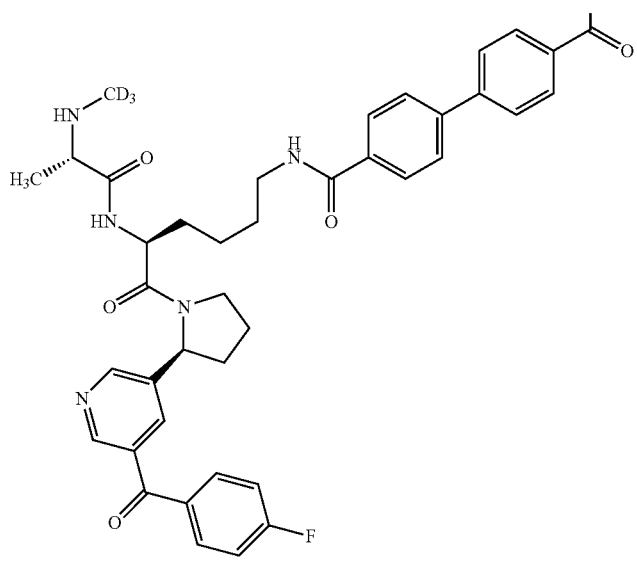

Biphenyl-4,4'-dicarboxylic acid bis-{[(S)-6-{(S)-2-[5-(4-fluoro-benzoyl)-pyridin-3-yl]-pyrrolidin-1-yl}-5-((S)-2-(trideuteromethyl-amino-propionylamino)-6-oxo-hexyl)]-amide}

Example 1L may be made by one skilled in the art, by the same process used to make other examples from Table 1A (specifically 1J) by the substitution of (S)-2-(tert-butoxycarbonyl-trideuteromethyl-amino)-propionic acid for (S)-2-(tert-butoxycarbonyl-methyl-amino)-propionic acid in Step 3 of the procedure above. (S)-2-(tert-butoxycarbonyl-trideuteromethyl-amino)-propionic acid is made by the alkylation of (S)-2-tert-Butoxycarbonylamino-propionic acid with trideuteromethyl iodide using sodium hydride.

Example 2
Preparation of Heptanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide) (2A)
(2A)
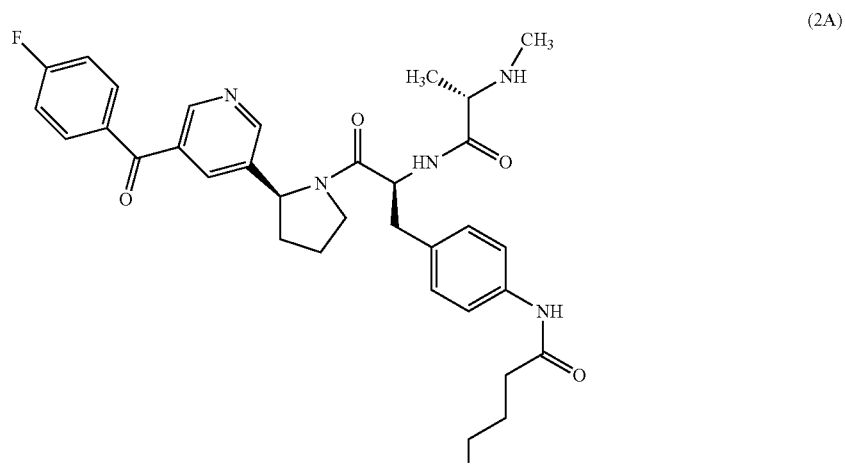
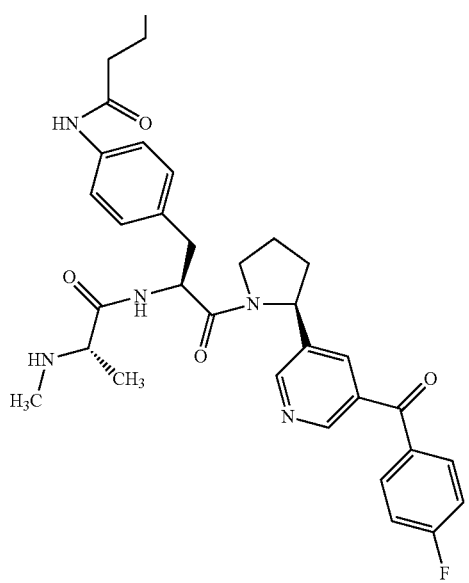

Step 1: Preparation of Intermediate [4-((S)-2-tert-butoxycarbonylamino-3-{(S)-2-[5-(4-fluoro-benzoyl)-pyridin-3-yl]-pyrrolidin-1-yl}-3-oxo-propyl)-phenyl]-carbamic acid 9H-fluoren-9-ylmethyl ester (I-2a)

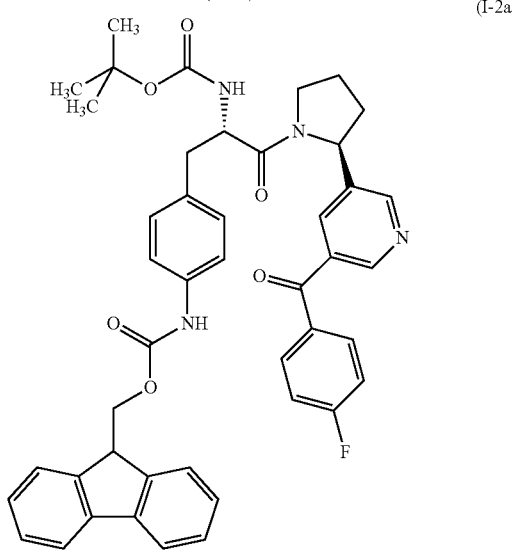

To a solution of (4-fluoro-phenyl)-((S)-5-pyrrolidin-2-yl-pyridin-3-yl)-methanone (1.0 g, 3.7 mmol), (S)-2-tert-butoxycarbonylamino-3-[4-(9H-fluoren-9-ylmethoxycarbonylamino)-phenyl]-propionic acid (2.21 g, 4.4 mmol) and ethyldiisopropylamine (3 mL) in DMF (20 mL) was added a solution of 2-(1H-benzo[d][1,2,3]triazol-1-yl)-1,1,3,3-tetramethylisouronium hexafluorophosphate(V) (1.67 g, 4.4 mmol) and 1H-benzo[d][1,2,3]triazol-1-ol (0.6 g, 4.4 mmol) in DMF (10 mL) and the reaction mixture was shaken for 16 hours. The reaction mixture was diluted with ethyl acetate (300 ml), washed sequentially with brine (2×) (300 mL), saturated aqueous bicarbonate solution (300 mL), brine (300 mL), water (300 mL), and brine (300 mL), then dried over Na$_2$SO$_4$/MgSO$_4$, and concentrated in vacuo to provide the crude product [4-((S)-2-tert-butoxycarbonylamino-3-{(S)-2-[5-(4-fluoro-benzoyl)-pyridin-3-yl]-pyrrolidin-1-yl}-3-oxo-propyl)-phenyl]-carbamic acid 9H-fluoren-9-ylmethyl ester as a light yellow foam.

MS (ESI) m/e 755.5 (M+H$^+$); HPLC (Novapak 150×3.9 mm C18 column: mobile phase: 35-90% acetonitrile/water with 0.1% TFA, at 2 mL/minute over 5 minutes.) t 3.885 minutes. The crude compound was carried forward to the next step without purification.

Step 2: Preparation of Intermediate ((S)-5-amino-6-{(S)-2-[5-(4-fluoro-benzoyl)-pyridin-3-yl]-pyrrolidin-1-yl}-6-oxo-hexyl)-carbamic acid 9H-fluoren-9-ylmethyl ester (I-2b)

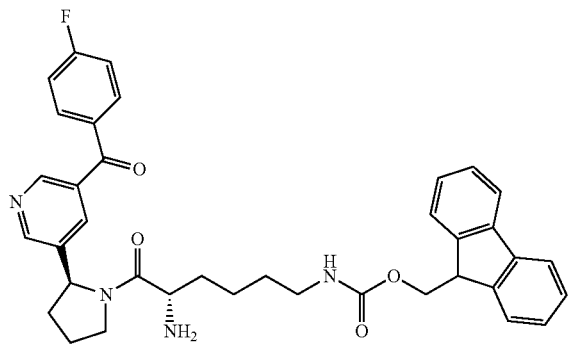

To a solution of [4-((S)-2-tert-butoxycarbonylamino-3-{(S)-2-[5-(4-fluoro-benzoyl)-pyridin-3-yl]-pyrrolidin-1-yl}-3-oxo-propyl)-phenyl]-carbamic acid 9H-fluoren-9-ylmethyl ester (I-2a) in dichloromethane (15 mL) was added trifluoroacetic acid (5 mL). After stirring for 45 minutes, the reaction mixture was concentrated in vacuo to afford crude ((S)-5-amino-6-{(S)-2-[5-(4-fluoro-benzoyl)-pyridin-3-yl] pyrrolidin-1-yl}-6-oxo-hexyl)-carbamic acid 9H-fluoren-9-ylmethyl ester as a dark amber residue.

HPLC (Novapak 150×3.9 mm C18 column: mobile phase: 35-90% acetonitrile/water with 0.1% TFA, at 2 mL/minute over 5 minutes.) t 2.473 minutes. The crude product was carried forward to the next step without purification.

Step 3: Preparation of Intermediate [4-((S)-2-[(S)-2-(tert-butoxycarbonyl-methyl-amino)-propionylamino]-3-{(S)-2-[5-(4-fluoro-benzoyl)-pyridin-3-yl]-pyrrolidin-1-yl}-3-oxo-propyl)-phenyl]-carbamic acid 9H-fluoren-9-ylmethyl ester (I-2c)

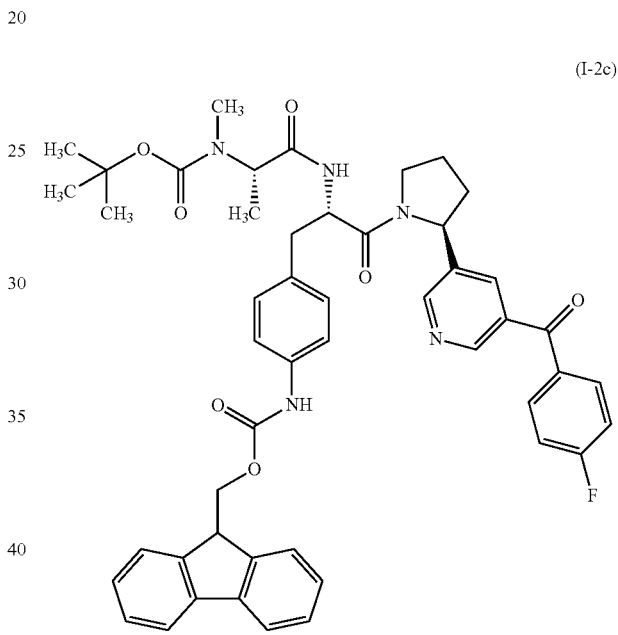

To a solution of [4-((S)-2-amino-3-{(S)-2-[5-(4-fluoro-benzoyl)-pyridin-3-yl]-pyrrolidin-1-yl}-3-oxo-propyl)-phenyl]-carbamic acid 9H-fluoren-9-ylmethyl ester (I-2b: 2.4 g, 3.7 mmol), (S)-2-(tert-butoxycarbonyl-methyl-amino)-propionic acid (0.89 g, 4.4 mmol) and ethyldiisopropylamine (7 mL) in DMF (20 mL) was added a solution of 2-(1H-benzo[d][1,2,3]triazol-1-yl)-1,1,3,3-tetramethylisouronium hexafluorophosphate(V) (1.67 g, 4.4 mmol) and 1H-benzo[d][1,2,3]triazol-1-ol (0.6 g, 4.4 mmol) in DMF (10 mL) and the reaction mixture was shaken for 16 hours. The reaction mixture was diluted with ethyl acetate (300 mL), washed sequentially with brine (2×) (300 mL), saturated aqueous bicarbonate solution (300 mL), brine (300 mL), water (300 mL), and brine (300 mL), then dried over Na$_2$SO$_4$/MgSO$_4$, and concentrated in vacuo to provide crude [4-((S)-2-[(S)-2-(tert-butoxycarbonyl-methyl-amino)-propionylamino]-3-{(S)-2-[5-(4-fluoro-benzoyl)-pyridin-3-yl]-pyrrolidin-1-yl}-3-oxo-propyl)-phenyl]-carbamic acid 9H-fluoren-9-ylmethyl ester as a yellow foam.

MS (ESI) m/e 840.7 (M+H$^+$); HPLC (Novapak 150×3.9 mm C18 column: mobile phase: 35-90% acetonitrile/water with 0.1% TFA, at 2 mL/minute over 5 minutes.) t 3.902 minutes. The crude product was carried forward to the next step without purification.

Step 4: Preparation of Intermediate [(S)-1-((S)-1-(4-amino-benzyl)-2-{(S)-2-[5-(4-fluoro-benzoyl)-pyridin-3-yl]-pyrrolidin-1-yl}-2-oxo-ethylcarbamoyl)-ethyl]-methyl-carbamic acid tert-butyl ester (I-2d)

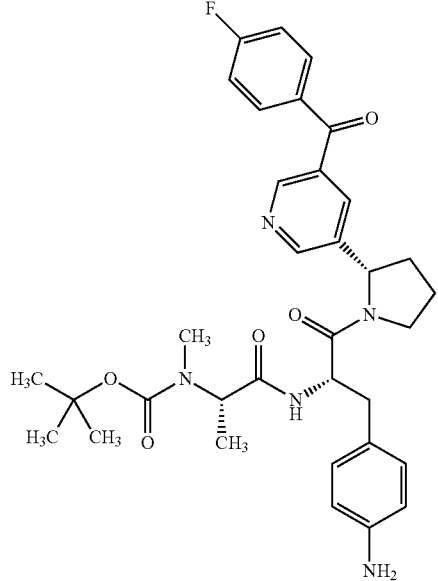

(I-2d)

To [4-((S)-2-[(S)-2-(tert-butoxycarbonyl-methyl-amino)-propionylamino]-3-{(S)-2-[5-(4-fluoro-benzoyl)-pyridin-3-yl]-pyrrolidin-1-yl}-3-oxo-propyl)-phenyl]-carbamic acid 9H-fluoren-9-ylmethyl ester (I-2c: 2.98 g, 3.7 mmol) was added 2M dimethylamine in THF (20 mL) and the reaction mixture was stirred for 2 hours. The reaction mixture was concentrated in vacuo and purification was accomplished with semi-preparative reverse phase HPLC (300×50 mm) eluting w/10-60% acetonitrile/water over 45 minutes. followed by lyophilization of the desired fractions. This provided [(S)-1-((S)-1-(4-amino-benzyl)-2-{(S)-2-[5-(4-fluoro-benzoyl)-pyridin-3-yl]-pyrrolidin-1-yl}-2-oxo-ethylcarbamoyl)-ethyl]-methyl-carbamic acid tert-butyl ester (1.5 g, 65.6% over 4 steps).

MS (ESI) m/e 618.5 (M+H$^+$); HPLC (Novapak 150×3.9 mm C18 column: mobile phase: 15-90% acetonitrile/water with 0.1% TFA, at 2 mL/minute over 5 minutes.) t 2.677 minutes.

Step 5: Preparation of Intermediate (I-2e)

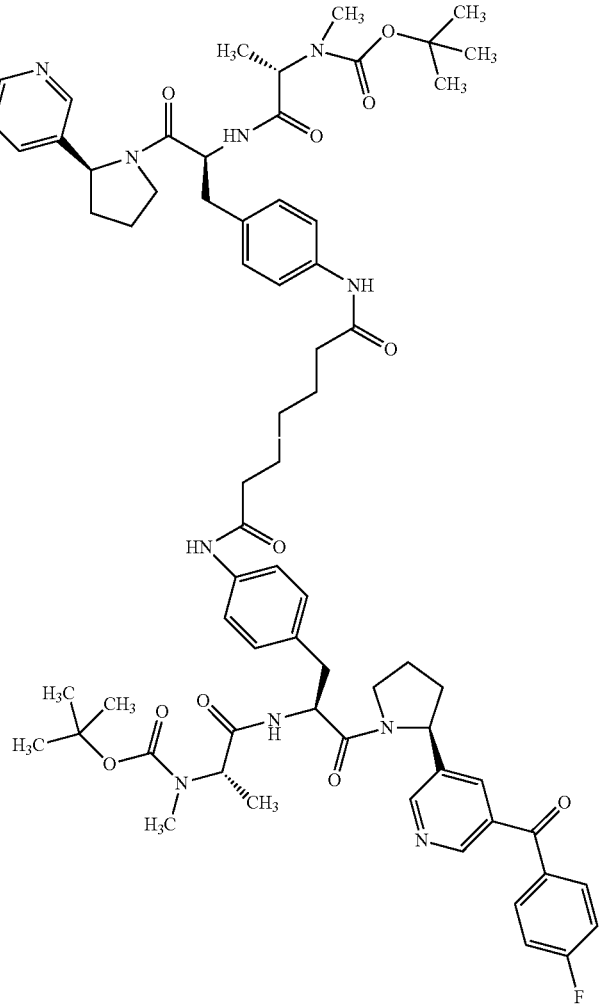

(I-2e)

To a solution of [(S)-1-((S)-1-(4-amino-benzyl)-2-{(S)-2-[5-(4-fluoro-benzoyl)-pyridin-3-yl]-pyrrolidin-1-yl}-2-oxo-ethylcarbamoyl)-ethyl]-methyl-carbamic acid tert-butyl ester (I-2d: 0.150 g, 0.243 mmol), and triethylamine (0.126 g, 0.971 mmol) in DCM (5 mL) was added a solution of heptanedioyl dichloride (0.024 g, 0.121 mmol) in DCM (1 mL) and the mixture was shaken for 16 hours. The reaction mixture was washed with sat. bicarbonate solution (100 ml), and concentrated in vacuo to provide crude Intermediate (I-2e).

HPLC (Novapak 150×3.9 mm C18 column: mobile phase: 35-90% acetonitrile/water with 0.1% TFA, at 2 mL/minute over 5 minutes.) t 2.977 minutes. The crude product was carried forward directly to the next step without purification.

Final Step: Preparation of Heptanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide)-(2A)

To a solution of Intermediate I-2e (35 mg, 0.025 mmol) in dichloromethane (4 mL) was added trifluoroacetic acid (2 mL) and the mixture stirred for 30 minutes. The reaction mixture was then concentrated in vacuo to afford crude Compound 2A as a dark amber residue. Purification by semi-preparative reverse phase HPLC (300×50 mm) eluting w/10-60% acetonitrile/water over 45 minutes followed by lyophilization of the desired fractions gave the trifluoroacetate salt of Compound 2A (Compound 2A-1). The material was neutralized by passing through a column of bicarbonate MP resin eluting sequentially with methanol (10 mL), then concentrated in vacuo to afford the free base (Compound 2A). This material was dissolved in ethyl acetate (10 mL) and methanol (0.5 mL) and treated with a saturated solution of citric acid in ethyl acetate (5.5 mL). The precipitate that resulted was filtered off under nitrogen and dried under vacuum, to provide the citric acid salt of Compound 2A (Compound 2A-2: 2.4 mg, 0.85% over 3 steps):

$^1$H NMR (400 MHz, CD$_3$OD): δ 8.66-8.86 (m, 3.52H), 8.49-8.65 (m, 3.03H), 7.86-8.04 (m, 5.86H), 7.38-7.58 (m, 4.83H), 7.07-7.38 (m, 8.44H), 5.10-5.25 (m, 2.44H), 5.00-5.10 (m, 2.07H), 4.45-5.09 (m, 3.05H), 3.97-4.08 (m, 1.65H), 3.45-3.91 (m, 6.99H), 2.92-3.19 (m, 4.15H), 2.74-2.92 (m, 14.96H), 2.33-2.53 (m, 8.74H), 2.06-2.22 (m, 2.00H), 1.58-2.02 (m, 7.89H), 1.40-1.58 (m, 5.16H), 1.21-1.28 (m, 1.72H):

MS (ESI) m/e 1159.8 (M+H$^+$);

HPLC (Novapak 150×3.9 mm C18 column: mobile phase: 10-90% acetonitrile/water with 0.1% TFA, at 2 mL/minute over 5 minutes) t 2.742 minutes.

The compounds in Table 2 below were prepared using procedures analogous to those described above for the preparation of Example 2A, 2A-1 and 2A-2 with the appropriate starting materials.

TABLE 2

| Ex. No. | |
|---|---|
| 2B | 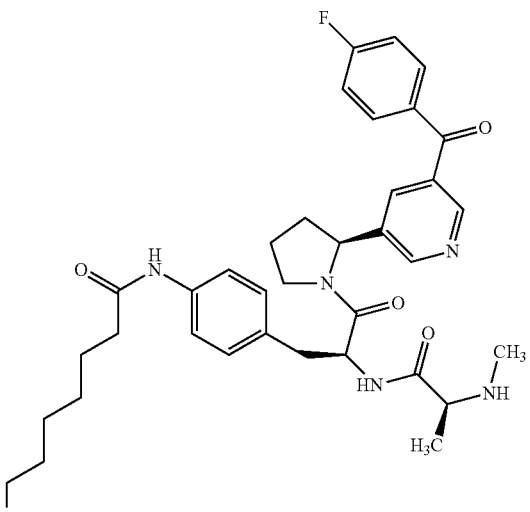 |

| Ex. No. |
|---|

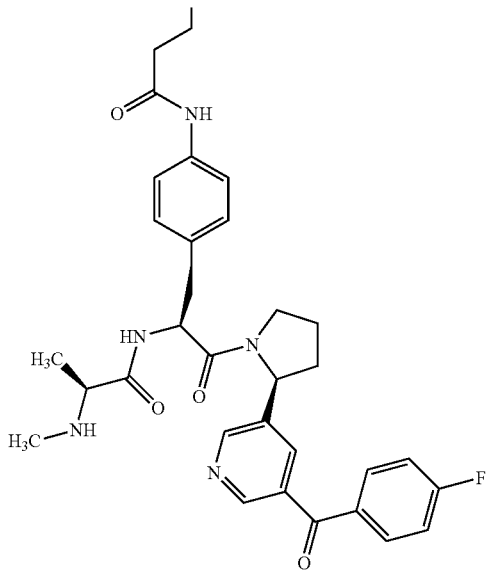

Decanedioic acid bis-({4-[(S)-3-{(S)-2-[5-(4-fluoro-benzoyl)-pyridinyl-3-yl]-pyrrolidin-1-yl}-2-((S)-2-methylamino-propionylamino)-3-oxo-propyl]-phenyl}-amide)
The citrate salt of the product was generated as a white solid (18 mg, yield 6.2% in three steps):
$^1$H NMR (400 MHz, CD$_3$OD): δ 8.64-8.81(m, 3.49 H), 8.49-8.64(m, 3.04 H), 7.84-8.01(m, 6.23 H), 7.34-7.57(m, 5.41 H), 7.08-7.35(m, 8.87 H), 5.08-5.22(m, 2.42 H), 4.97-5.08(m, 2.09 H), 4.63-4.74(m, 1.30 H), 4.52-4.63(m, 1.36 H), 3.93-4.05(m, 1.80 H), 3.54-3.81(m, 5.03 H), 3.43-3.52(m, 1.30 H), 3.34-3.36(m, 1.30 H), 3.97-3.20(m, 3.84 H), 2.86-2.97(m, 1.39 H), 2.67-2.86(m, 8.94 H), 2.25-2.52(m, 9.24 H), 2.02-2.25(m, 3.18 H), 1.75-1.99(m, 3.83 H), 1.53-1.75(m, 4.19 H), 1.28-1.53(m, 10.12 H);
MS (ESI) m/e 1201.8 (M + H$^+$);
HPLC (Novapak 150 × 3.9 mm C18 column: mobile phase: 10-90% acetonitrile/water with 0.1% TFA, at 2 mL/minute over 5 minutes) t 2.945 minutes.

2C

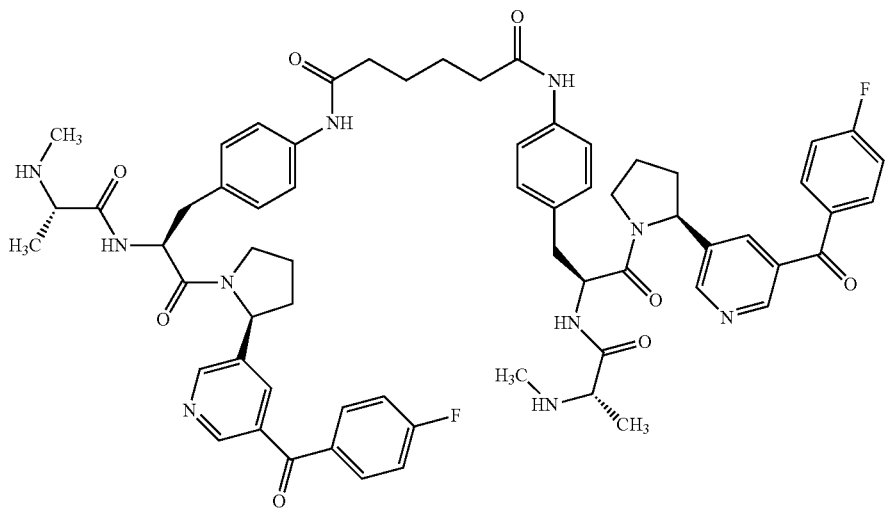 [SMILES: CN[C@@H](C)C(=O)N[C@@H](Cc1ccc(NC(=O)CCCCC(=O)Nc2ccc(C[C@H](NC(=O)[C@H](C)NC)C(=O)N3CCC[C@H]3c3cncc(C(=O)c4ccc(F)cc4)c3)cc2)cc1)C(=O)N1CCC[C@H]1c1cncc(C(=O)c2ccc(F)cc2)c1]

Hexanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide)
MS (ESI) m/e 1146 (M + H$^+$);
Retention time = 2.702 ((10-90% acetonitrile/H$_2$O, 0.1% TFA) 2 mL/minute TABLE 2-continued
| Ex. No. | |
|---|---|
| 2D | 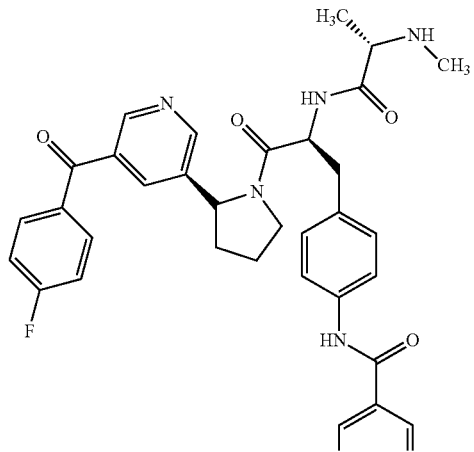<br>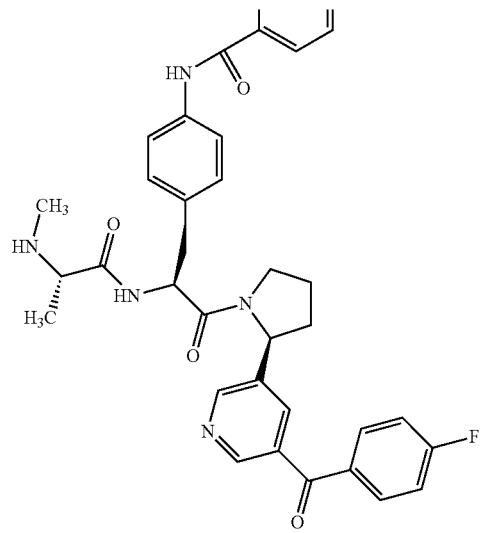<br>N,N'-Bis-{4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-pheny}-isophthalamide |

| Ex. No. | |
|---|---|
| 2E | 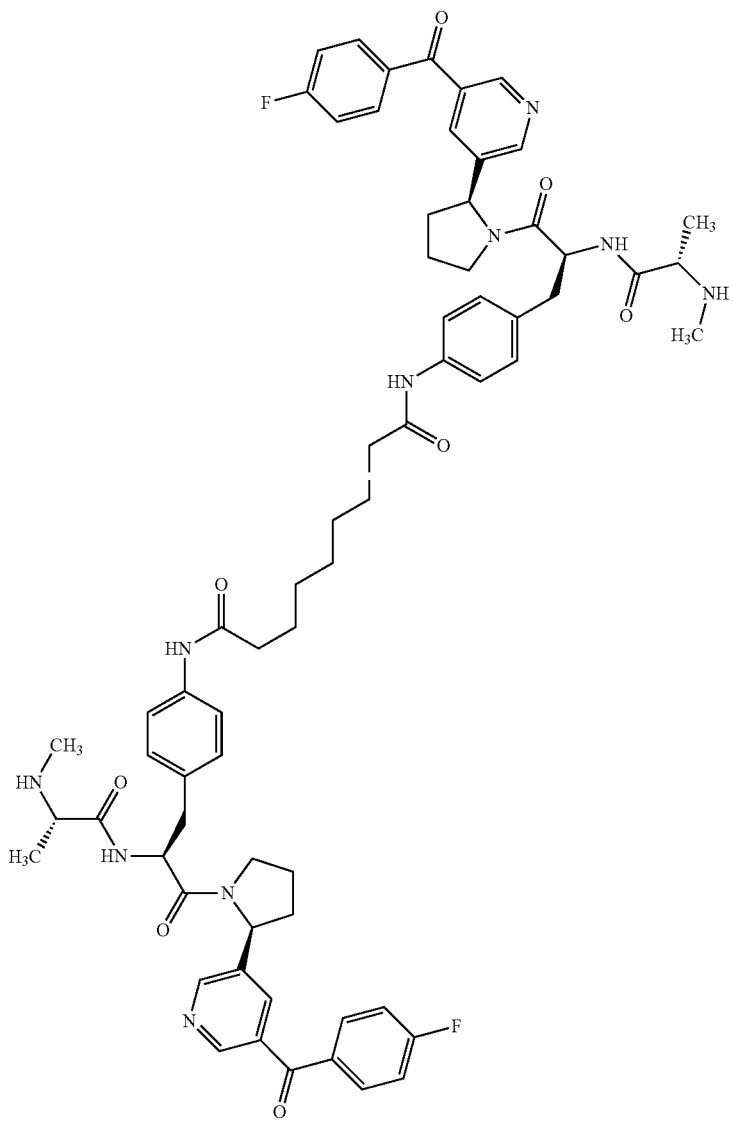 [SMILES: CN[C@@H](C)C(=O)N[C@@H](Cc1ccc(NC(=O)CCCCCCCC(=O)Nc2ccc(C[C@H](NC(=O)[C@H](C)NC)C(=O)N3CCC[C@H]3c3cncc(C(=O)c4ccc(F)cc4)c3)cc2)cc1)C(=O)N1CCC[C@H]1c1cncc(C(=O)c2ccc(F)cc2)c1] |

Nonanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide)

The citrate salt of the product was generated as a white solid (20.5 mg, yield 7.1% in three steps):

$^1$H NMR (400 MHz, CD$_3$OD): δ 8.66-8.86(m, 3.50 H), 8.44-8.64(m, 3.47 H), 7.80-8.07(m, 6.63 H), 7.61-7.77(m, 1.93 H), 7.38-7.58(m, 4.64 H), 7.08-7.37(m, 7.90 H), 5.10-5.37(m, 3.60 H), 4.99-5.10(m, 2.00 H), 4.54-4.78(m, 2.69 H), 4.39-4.52(m, 1.21 H), 3.97-4.08(m, 1.49 H), 3.47-3.89(m, 6.49 H), 2.91-3.02(m, 4.28 H), 2.71-2.91(m, 7.39 H), 2.54-2.66(m, 0.86 H), 2.27-2.53(m, 7.82 H), 2.05-2.24(m, 2.35 H), 1.53-2.00(m, 6.85 H), 1.29-1.53(m, 7.53 H);

MS (ESI) m/e 1188.1 (M + H$^+$);

HPLC (Novapak 150 × 3.9 mm C18 column: mobile phase: 10-90% acetonitrile/water with 0.1% TFA, at 2 mL/minute over 5 minutes) t 2.864 minutes.

| Ex. No. | |
|---|---|
| 2F | 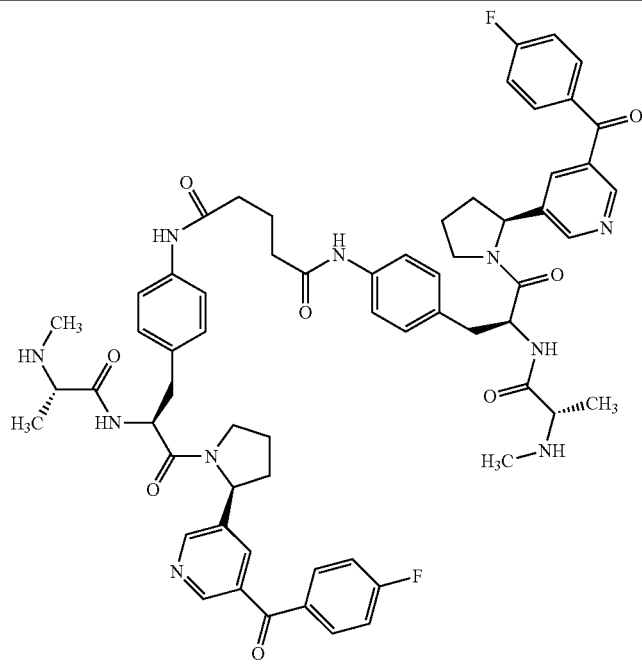<br>Pentanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide)<br>MS (ESI) m/e 1132 (M + H$^+$);<br>Retention time = 2.689 (10-90% acetonitrile/H$_2$O, 0.1% TFA) 2 mL/minute |

Pharmacological Data

The compounds described herein above were profiled using a cellular assay (using SKOV3 or Panc3.27 tumor cells) and a binding assay to determine the competition between the compounds of the present invention and smac7 mer peptide for XIAP-BIR3 and cIAP1-BIR3 binding groove occupancy.

Cellular Assay—Treatment of SKOV3 or Panc3.27 Tumor Cells with Dimeric IAP Antagonists On day one adherent SKOV3 and Panc3.27 cells are plated into two 96-well, clear, flat bottom plates. All wells in row A contain 90 uL of media. All wells in rows B-G contain a total volume of 90 uL per well and 2000 cells per well for SKOV3 and 4000 cells per well for Panc3.27 cell lines. Plates are then incubated overnight for 18 hours at 37° C., 5% CO$_2$.

On day two cells are treated with the compounds of formula M-L-M'. Treatments are done in triplicate. The compounds are first serially diluted in DMSO and then added to media giving a final concentration of 0.2% DMSO when added to cells. Cells are treated with 10 uL of serially diluted compounds of formula M-L-M' at a final concentration of 1000 nM, 200 nM, 40 nM, 8 nM, 1.6 nM, 0.32 nM, 0.06 nM, 0.013 nM, 0.0026 nM, and one untreated well. Plate two is used as a time zero plate.

To measure cell viability 50 uL of Cell Titer Glo (CTG) solution is added to row A, media only and B, cells and media. CTG is purchased from Promega Corporation catalog number G7573. The solution is prepared according to manufacturer's instructions. CTG measures the amount of ATP released from viable cells that is proportional to the number of cells in each well. After incubating for ten minutes with CTG plates are measured on a luminescent reader at 700 nM wavelength. Read time is approximately one second per well for a 96-well plate.

On day five 50 uL of CTG is added to plate one, rows A-G, incubated for 10 minutes at room temperature and read on a luminescent reader. Raw data is adjusted to account for the time zero plate as well as background noise. Triplicate values are averaged and percent control growth is calculated. Percent control growth is calculated using the following logical test: If well read data point (a) is greater than time zero data point (t=0), then 100*[(a)−(t=0)]/[(72 hour total growth)−(t=0)], OR 100*[(a)−(t=0)]/[(t=0)]. Data is represented by line graph with the concentration of compound on the x axis and percent control growth on the y axis.

The results are presented in Table 3 below.

Binding Assay

The present method includes utility of a Surface plasmon resonance (SPR)-based biosensor (Biacore™ GE Healthcare, Uppsala, Sweden) to examine competition between the compounds of the present invention and smac7 mer peptide for XIAP-BIR3 and cIAP1-BIR3 binding groove occupancy.

Biacore™ utilizes the phenomenon of surface plasmon resonance (SPR) to detect and measure binding interactions. In a typical Biacore experiment, one of the interacting molecules is immobilized on a flexible dextran matrix while the interacting partner is flowed over the derivatized surface. A binding interaction results in an increase in mass on the sensor surface and a corresponding direct change in the refractive index of the medium in the vicinity of the sensor surface. Changes in refractive index or signal are recorded in resonance units (R.U.) Signal changes due to association and dissociation of complexes are monitored in a non-invasive manner, continuously and in real-time, the results of which are reported in the form of a sensorgram.

Solution Inhibition Assay Format:

Biacore™ T100 (GE Healthcare, Uppsala, Sweden) was used to conduct all experiments reported herein. Sensor surface preparation and interaction analyses were performed at 25° C. Buffer and Biacore reagents were purchased from GE Healthcare. Running buffer containing 10 mM Hepes, pH7.4, 150 mM sodium chloride, 1.25 mM Dithiothreitol, 2% Dimethyl sulfoxide and 0.05% polysorbate 20 was utilized throughout all experiments.

Biotinylated smac7 mer peptide was diluted to 10 nM in running buffer and captured onto a sensor surface pre-derivatized with streptavidin (sensor chip SA) towards peptide surface densities in the range 40-100 R.U. Peptide captured surfaces were blocked with 500 μM $PEO_2$-Biotin (Thermo Scientific). A blank flowcell was similarly blocked with $PEO_2$-biotin and served as a reference flowcell in the competition assay.

Interaction analyses were performed by first equilibrating each compound within a six point seven fold compound dilution series in the range 1 μM to 0.06 nM with either 100 nM XIAP-BIR3 or 6 nM cIAP1-BIR3 for at least one hour during instrument start-up procedures. Protein compound mixtures were then injected over reference and smac7 mer peptide surfaces in series for 60 seconds at a flow-rate of 64 μL/minutes. Surface regeneration was performed at the end of each analysis cycle by a 30 second injection of 10 mM Glycine, pH 2.5, 1M Sodium Chloride, 0.05% polysorbate 20. Additionally, control compound samples and control XIAP-BIR3 or cIAP1-BIR3 samples were prepared and run at regular intervals to monitor surface and assay performance.

Data analyses were carried out using Biacore™ T100 evaluation software v2.0 to validate assay quality. Binding level report points were plotted versus logarithmic compound concentration values and analyzed in Graphpad prism 5 via non-linear regression using a one-site competition model. EC50 values were generated and used as a measure of inhibitor potency.

The results are presented in Table 3 below.

In vitro combination studies were performed according to the cellular assay described above, except that cells were dosed with a fixed concentration of the IAP inhibitor and the dose level of the combination agent was varied. Combination activity (either additive or synergistic) occurs when either agent alone has no single agent activity and the IC50 of the second agent shifts leftward (i.e., agent potency was increased) by ≧5 fold as a result of the combination. A ≧5 fold increase in potency was observed for the combination of Example 1J with Paclitaxel; whereas, neither Example 1J nor paclitaxel alone showed significant activity.

In vivo combination studies were modeled after the in vitro studies described above. Cohorts of mice (n=8) were treated with (1) Cohort A: Example 1J (3 mg/kg, 1× per week), (2) Cohort B: Paclitaxel (12 mg/kg, 3× per week), or (3) Cohort C: a combination of Example 1J (3 mg/kg, 1× per week)+ Paclitaxel (12 mg/kg, 3× per week). Studies typically initiated dosing when xenograft tumors were 100 $mm^3$ and lasted 2-3 weeks. Positive combination activity occurs when neither single agent treatment alone results in significant anti-tumor activity (i.e. the growth of the tumor in the treated animals is >50% of that seen in untreated animals) but the combination results in >80% control of the tumor growth compared to the untreated animals. For both Cohorts A and B tumor growth control was <50%, while tumor growth control of >80% was observed for Cohort C (combination of Example 1J with Paclitaxel).

What is claimed is:

1. A compound of formula M-L-M', where M and M' are each independently a monomeric moiety of Formula (I)

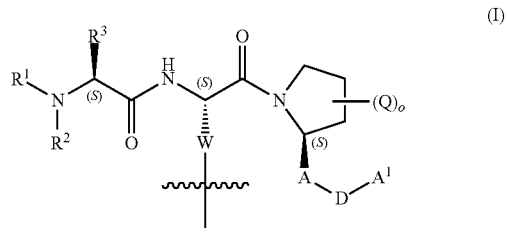

TABLE 3

| Ex No | Salt form tested | XIAP-BIR3 Binding Biacore (Competitive) EC50 [nmol $l^{-1}$] | CIAP-BIR3 Binding Biacore (Competitive) EC50 [nmol $l^{-1}$] | SKOV3 proliferation IC50 [nmol $l^{-1}$] | PANC proliferation IC50 [nmol $l^{-1}$] |
|---|---|---|---|---|---|
| 1A | citrate | 125.6-131 | 0.68-0.70 | 41.02-77.14 | 72.44-427.06 |
| 1B | citrate | 66.5-72.8 | 0.68-0.68 | 81.09-83.8 | 43.55-246.21 |
| 1C | citrate | 412.9-425.4 | 4.75-4.89 | 84.04-127.07 | 63.29-146.59 |
| 1D | citrate | 88.5-128.9 | 0.31-0.34 | 37.37-84.19 | 12.32-118.99 |
| 1E | citrate | 138.6-158.3 | 0.47-0.52 | 26.71-79.39 | 26.81-184.72 |
| 1F | citrate | 128.6-144.8 | 0.68-0.69 | 16.13-20.14 | 12.85-105.76 |
| 1G | citrate | 97.2-108.4 | 0.71-0.71 | 9.64-16.36 | 5.22-27.87 |
| 1H | citrate | 46.3-53.5 | 0.88-0.88 | 80.8-86.38 | 13.29-140.02 |
| 1I | citrate | 47.1-58.3 | 11.14-12.41 | 79.26-80.08 | 35.59-116.45 |
| 1J | citrate | 60.4-162.4 | 0.58-3.12 | <0.026-5.94 | <0.0026-6.67 |
| 1K | citrate | 636.5-704 | 18.43-19.42 | 9419.38-9461.02 | >10000 |
| 2A | citrate | 145.8-153.9 | 0.73-0.74 | 23.47-25.84 | no data |
| 2B | citrate | 130.6-193.7 | 0.37-0.41 | 7.39-15.44 | 11.7-25.89 |
| 2C | citrate | 124.7-138.5 | 0.58-0.60 | 59.74-316.56 | 144.07-390.69 |
| 2D | citrate | 228.3-238.5 | 0.66-0.68 | 107.4-290.83 | 166.84-693.91 |
| 2E | citrate | 99.4-103.5 | 0.73-0.81 | 17.15-23.51 | 37.62-95.65 |
| 2F | citrate | 122.7-125.9 | 0.70-0.70 | 966.63->10000 | 88.26-393.41 | wherein:

$R^1$ is $(C_1-C_4)$alkyl or hydrogen;

$R^2$ is hydrogen, $(C_1-C_4)$alkyl, halo-substituted $(C_1-C_4)$alkyl, $(C_3-C_6)$cycloalkyl, —$CH_2$—$(C_3-C_6)$cycloalkyl, benzyl, HO—$(C_1-C_4)$alkyl-, or $CH_3NHC(O)$—;

$R^3$ is $(C_1-C_4)$alkyl, halo-substituted $(C_1-C_4)$alkyl, or hydrogen;

or $R^2$ along with the nitrogen atom to which $R^2$ is attached is taken together with $R^3$ to form a 3- to 6-membered heterocyclic ring optionally containing 1 to 2 additional hetero-ring atoms each independently selected from N, O and S;

Q is $(C_1-C_4)$alkyl, $(C_1-C_4)$alkoxy, —OH, —C(O)—$(C_1-C_4)$alkyl, —O—C(O)—$(C_1-C_4)$alkyl, —$NH_2$, —NH—$(C_1-C_4)$alkyl, —N$((C_1-C_4)$alkyl$)_2$, —NH—C(O)—$(C_1-C_4)$alkyl, —NHSO$(C_1-C_4)$alkyl, —NHSO(phenyl), —N$((C_1-C_4)$alkyl)-SO$(C_1-C_4)$alkyl, —N$((C_1-C_4)$alkyl)-SO(phenyl), —NHSO$_2(C_1-C_4)$alkyl, —NHSO$_2$(phenyl), —N$((C_1-C_4)$alkyl)-SO$_2(C_1-C_4)$alkyl, or —N$((C_1-C_4)$alkyl)-SO$_2$(phenyl);

o is 0, 1, or 2;

A is a 6-membered heteroaryl ring containing at least one N ring heteroatom;

D is a bond, —C(O)—, —O—, —NH—, —S—, —S(O)—, —SO$_2$—, —N$((C_1-C_4)$alkyl)-, —N$((C_1-C_4)$alkyl-OH)—, —N$((C_3-C_6)$cycloalkyl)-, —NHC(O)—, —N$((C_1-C_4)$alkyl)C(O)—, —C(O)NH—, —C(O)—N$((C_1-C_4)$alkyl)-, —N$((C_1-C_4)$alkyl-CO$_2$—$(C_1-C_4)$alkyl)-, —$(C_1-C_4)$alkylene, $(C_2-C_6)$alkenylene, —CH(OH)—, —C(O)—$(C_1-C_4)$alkylene, —NH—$(C_1-C_4)$alkylene, —S—$(C_1-C_4)$alkylene, —S(O)—$(C_1-C_4)$alkylene, —SO$_2$—$(C_1-C_4)$alkylene, —NHSO$_2(C_1-C_4)$alkylene, —NHSO$(C_1-C_4)$alkylene, or —CH(R)—, where R is $NH_2$, —NH$((C_1-C_4)$alkylene)phenyl, —NH$(C_1-C_4)$alkyl, —O$((C_1-C_4)$alkylene)phenyl or —O$(C_1-C_4)$alkyl, wherein said $((C_1-C_4$alkylene)phenyl or $(C_1-C_4)$alkyl is optionally substituted with halo;

$A^1$ is H, $CF_3$, phenyl, naphthyl, a partially or fully saturated $(C_3-C_6)$cycloalkyl, a 5- to 12 membered partially or fully saturated heterocycle containing 1 to 3 heteroatoms each independently selected from O, S or N, or a 5- to 10-membered heteroaryl containing 1 to 4 heteroatoms each independently selected from O, S or N, where said phenyl, naphthyl and said heteroaryl are optionally substituted with 1 to 3 substituents each independently selected from halo, $(C_1-C_4)$alkyl, halo-substituted$(C_1-C_4)$alkyl, $(C_1-C_4)$alkoxy, —C(O)NHCH$_3$, —C(O)N(CH$_3$)$_2$, CN, or NO$_2$, and where said heterocycle and said cycloalkyl are optionally fused to a phenyl or 6-membered heteroaryl containing 1 to 3 heteroatoms each independently selected from O, S or N, and where said heterocycle, said cycloalkyl, said fused heterocycle and said fused cycloakyl are optionally substituted with oxo, halo, $(C_1-C_4)$alkyl, halo-substituted$(C_1-C_4)$alkyl, or $(C_1-C_4)$alkoxy;

W is a bond, $(C_1-C_{10})$alkylene, $(C_2-C_{10})$alkenylene, $((C_1-C_4)$alkylene$)_m$-$(Y)_n$—B, or $((C_2-C_4)$alkenylene$)_m$-$(Y)_n$—B, where m and n are each independently 0 or 1, Y is phenylene, naphthylene, a partially or fully saturated 3- to 6-membered cycloalkylene, 5- to 6-membered fully or partially saturated heterocyclene containing 1 to 3 heteroatoms each independently selected from O, S or N, or a 5- to 10-heteroarylene containing 1 to 4 heteroatoms each independently selected from O, S, or N, and B is a bond, —O—, $(C_1-C_4)$alkylene, or —(CH$_2$)(phenylene), where said $(C_1-C_{10})$alkylene, $(C_2-C_{10})$alkenylene, $(C_1-C_4)$alkylene, or $(C_2-C_4)$alkenylene moiety optionally contains an oxygen or nitrogen atom interspersed within the alkylene chain and is optionally substituted with oxo, —$CF_3$, phenyl, naphthyl, a 5- to 10-membered heteroaryl containing 1 to 4 heteroatoms each independently selected from O, S, or N, a partially or fully saturated 5- to 6-membered cycloalkyl, a 5- to 6-membered fully or partially saturated heterocycle containing 1 to 3 heteroatoms each independently selected from O, S or N, and/or 1 or more halo, where said partially or fully saturated heterocyclene is optionally substituted with 1 to 2 substituents each independently selected from oxo, $(C_1-C_4)$alkyl, or halo, where said heteroaryl or said heteroarylene is optionally substituted with 1 to 3 substituents selected from halo or $(C_1-C_4)$alkyl, and where said phenylene, said phenyl, said naphthyl, said naphthylene, said cycloalkylene, or said cycloalkyl is optionally substituted with 1 to 3 substituents each independently selected from halo, —$CF_3$, $(C_1-C_4)$alkyl, or $(C_1-C_4)$alkoxy, or when W is $((C_1-C_4)$alkylene$)_m$-$(Y)_n$—B or $((C_2-C_4)$alkenylene$)_m$-$(Y)_n$—B and L is $NR^5$—C(O)—$X^2$—C(O)—$NR^5$— or —$NR^5$—S(O)$_2$—$X^2$—S(O)$_2$—$NR^5$—, B is optionally taken together with $R^5$ along with the nitrogen to which $R^5$ is attached to form a heterocyclic ring selected from the group consisting of aziridinyl, azetidinyl, pyrrolidinyl, 1H-pyrrolyl, piperidinyl, 1H-indolyl, indolinyl, 1H-dihydroimidazolyl, 1H-imidazolyl, piperazinyl, hexahydropyrimidinyl, 1,2,3,4-tetrahydroquinolinyl, 1,2,3,4-tetrahydroisoquinolinyl, 5,6,7,8-tetrahydropyrido[3,4-b]pyrazinyl, oxazolidinyl, and thiazolidinyl, where said heterocyclic ring is optionally substituted with 1 to 3 substituents each independently selected from $(C_1-C_4)$alkyl, —OH, or oxo;

L is a linker group selected from the group consisting of —C(O)—$NR^5$—$X^1$—$NR^5$—C(O)—, —S(O)$_2$—$NR^5$—$X^1$—$NR^5$—S(O)$_2$—, —$NR^5$—C(O)—$X^2$—C(O)—$NR^5$—, and —$NR^5$—S(O)$_2$—$X^2$—S(O)$_2$—$NR^5$—, where $R^5$ is hydrogen, $(C_1-C_4)$alkyl, benzyl, or cyclohexyl; and $X^1$ is
(i) a bond,
(ii) $(C_1-C_{10})$alkylene, $(C_2-C_{10})$alkenylene, $(C_2-C_{10})$alkynylene, —$((C_1-C_{10})$alkylene)-O$(C_1-C_6)$alkylene$)_t$-, or $(C_1-C_{10})$alkylene-NH$(C_1-C_6)$alkylene, where t is 0, 1 or 2,
(iii) phenylene, naphthylene, fluorenylene, 9H-fluoren-9-onylene, 9,10-dihydroanthracenylene, anthracen-9,10-dionylene, a partially or fully saturated $(C_3-C_8)$cycloalkylene, a 5- to 7-membered heterocyclene containing 1 to 3 heteroatoms each independently selected from O, S, or N, or a 5- to 10-membered heteroarylene containing 1 to 3 heteroatoms each independently selected from O, S or N, where said phenylene is optionally fused to a $(C_5-C_6)$cycloalkyl,
(iv) (phenylene)-G-(phenylene), where G is a bond, O, S, —NH—, —N═N—, —S═S—, —SO$_2$—, $(C_1-C_6)$alkylene, $(C_2-C_6)$alkenylene, $(C_2-C_{10})$alkynylene, $(C_3-C_6)$cycloalkylene, a 5- to 6-membered heteroaryl containing 1 to 3 heteroatoms each independently selected from O, S, or N, or a 5- to 6-membered partially or fully saturated heterocyclene containing 1 to 3 heteroatoms each independently selected from O, S or N, and where said phenylene is optionally fused to a phenyl, (v) $((C_1-C_6)alkylene)_r-Z^1-((C_1-C_6)alkylene)_s$, or $((C_2-C_6)alkenylene)_r-Z^1-((C_2-C_6)alkenylene)_s$, where r and s are each independently 0, 1, or 2; and $Z^1$ is —O—, —N=N—, $(C_3-C_6)$cycloalkylene, phenylene, a 5- to 6-membered partially or fully saturated heterocyclene containing 1 to 3 heteroatoms each independently selected from O, S or N, or a 5- to 6-membered heteroarylene containing 1 to 3 heteroatoms each independently selected from O, S or N, where said heteroarylene and said heterocyclene are optionally fused to a phenyl, phenylene, a 5- to 6-membered partially or fully saturated heterocyclene containing 1 to 3 heteroatoms each independently selected from O, S or N, or a 5- to -6-membered heteroarylene containing 1 to 3 heteroatoms each independently selected from O, S or N, or (vi) $(C_1-C_{20})$alkylene or —NH—$((C_1-C_{20})$alkylene)-NH—, where said alkylene contains 1 to 6 oxygen atoms interspersed within the alkylene chain and optionally 1 to 2 phenylene groups interspersed within the alkylene chain;

or $X^1$ is optionally taken together with both $R^5$ groups along with the nitrogens to which both $R^5$ groups are attached to form an 2,6-diazaspiro[3.3]heptane;

$X^2$ is (i) a bond or —O—, —NH—, or —N$((C_1-C_4)$alkyl)-, (ii) $(C_1-C_{10})$alkylene, —O$(C_1-C_6)$alkylene$)_p$-, —$((C_1-C_6)$alkylene O$)_q$—, —O—$((C_1-C_6)$alkylene O$)_q$—, $(C_2-C_{10})$alkenylene, $((C_1-C_{10})$alkylene)-(O$(C_1-C_6)$alkylene$)_p$-, —O—$((C_1-C_{10})$alkyl)-O—, or $(C_1-C_{10})$alkylene-NH$(C_1-C_6)$alkylene, or $(C_2-C_{10})$alkynylene, where p and q are each independently 1, 2, or 3, (iii) phenylene, naphthylene, fluorenylene, 9H-fluoren-9-onylene, 9,10-dihydroanthracenylene, anthracen-9,10-dionylene, a partially or fully saturated $(C_3-C_8)$ cycloalkylene, a 5- to 7-membered heterocyclene containing 1 to 3 heteroatoms each independently selected from O, S, or N, or a 5- to 10-membered heteroarylene containing 1 to 3 heteroatoms each independently selected from O, S or N, where said phenylene is optionally fused to a $(C_5-C_6)$cycloalkyl, (iv) (phenylene)-G-(phenylene), or —O-(phenylene)-G-(phenylene)-O—, where G is a bond, O, S, —NH—, —N=N—, —S=S—, —SO$_2$—, $(C_1-C_6)$ alkylene, $(C_2-C_6)$alkenylene, $(C_3-C_6)$cycloalkylene, a 5- to 6-membered heteroaryl containing 1 to 3 heteroatoms each independently selected from O, S or N, or a 5- to 6-membered partially or fully saturated heterocyclene containing 1 to 3 heteroatoms each independently selected from O, S or N, and where said phenylene is optionally fused to a phenyl, (v) $((C_1-C_6)alkylene)_r-Z^1-((C_1-C_6)alkylene)_s$, $((C_2-C_6)alkenylene)_r Z^1-((C_2-C_6)alkenylene)_s$, or —(O$(C_1-C_3)$alkylene$)_u$-$Z^2$—$((C_1-C_3)$alkylene O$)_v$—, where r, s, u, and v are each independently 0, 1, or 2; and $Z^1$ and $Z^2$ are —O—, —N=N—, $(C_3-C_6)$cycloalkylene, phenylene, a 5- to 6-membered partially or fully saturated heterocyclene containing 1 to 3 heteroatoms each independently selected from O, S or N, or a 5- to -6-membered heteroarylene containing 1 to 3 heteroatoms each independently selected from O, S or N, where said heteroarylene and said heterocyclene are optionally fused to a phenyl, phenylene, a 5- to 6-membered partially or fully saturated heterocyclene containing 1 to 3 heteroatoms each independently selected from O, S or N, or a 5- to -6-membered heteroarylene containing 1 to 3 heteroatoms each independently selected from O, S or N, or (vi) $(C_1-C_{20})$alkylene or —NH—$((C_1-C_{20})$alkylene)-NH—, where said alkylene contains 1 to 6 oxygen atoms interspersed within the alkylene chain and optionally 1 to 2 phenylene groups interspersed within the alkylene chain;

where said group (ii) moieties of $X^1$ and $X^2$ are each independently substituted with one or more fluoro atoms, or 1 to 2 substituents each independently selected from halo, oxo, amino, phenyl, naphthyl, $(C_3-C_6)$cycloalkyl, or 5- to 6-membered heterocycle containing 1 to 3 heteroatoms each independently selected from O, N or S, where said phenyl, said cycloalkyl, and said heterocycle are optionally substituted with 1 to 3 substituents each independently selected from halo, $(C_1-C_4)$alkyl, or trifluoromethyl, where said group (iii) and (iv) moieties of $X^1$ and $X^2$ are optionally substituted with 1 to 4 substituents each independently selected from $(C_1-C_4)$alkyl, $(C_1-C_4)$ alkoxy, halo, amino, —OH, benzyl, or a fused 5- to 6-membered cycloalkyl, where said $(C_1-C_4)$alkyl, said $(C_1-C_4)$alkoxy, and said fused cycloalkyl are optionally substituted with 1 to 3 substituents selected from halo, or $(C_1-C_4)$alkyl, where said group (v) moieties of $X^1$ and $X^2$ are optionally substituted with 1 to 3 substituents each independently selected from halo, hydroxy, oxo, amino, $(C_1-C_4)$alkyl, $(C_1-C_4)$alkoxy, or phenyl;

or a pharmaceutically acceptable salt thereof.

2. The compound of claim 1 wherein M and M' are the same; or a pharmaceutically acceptable salt thereof.

3. The compound of claim 1 wherein L is —C(O)—NR$^5$—X$^1$—NR$^5$—C(O)—, or —S(O)$_2$—NR$^5$—X$^1$—NR$^5$—S(O)$_2$—, where R$^5$ is hydrogen or $(C_1-C_4)$alkyl; or a pharmaceutically acceptable salt thereof.

4. The compound of claim 1 wherein L is —NR$^5$—C(O)—X$^2$—C(O)—NR$^5$—, or —NR$^5$—S(O)$_2$—X$^2$—S(O)$_2$—NR$^5$—, where R$^5$ is hydrogen or $(C_1-C_4)$alkyl; or a pharmaceutically acceptable salt thereof.

5. The compound of claim 3 or 4 wherein R$^1$ is hydrogen, R$^2$ and R$^3$ are both methyl, and D is a bond, —C(O)—, —CH$_2$—, —CH(OH)—, —CH(NH$_2$)—, —O—, —S—, —S(O)—, —S(O)$_2$—, —NH—, —N$((C_1-C_4)$alkyl)-, —N$((C_1-C_4)$alkyl-OH)—, or —N(cyclopropyl)-; or a pharmaceutically acceptable salt thereof.

6. The compound of claim 1 wherein W is $(C_1-C_{10})$alkylene, 5- to 6-membered cycloalkylene, or $((C_1-C_4)$alkylene)phenylene; or a pharmaceutically acceptable salt thereof.

7. A compound of formula M-L-M', wherein M and M' are each independently a monomeric moiety of formula (II):

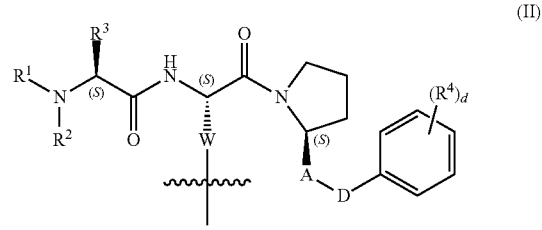

(II)

wherein:
R¹ is (C₁-C₄)alkyl or hydrogen;
R² is (C₁-C₄)alkyl or hydrogen;
R³ is (C₁-C₄)alkyl or hydrogen;
or R² along with the nitrogen atom to which it is attached is taken together with R³ to form a 3- to 6-membered heterocyclic ring optionally containing 1 to 2 additional hetero-ring atoms each independently selected from N, O and S;
A is a 6-membered heteroaryl ring containing at least one N ring heteroatom, where said heteroaryl is optionally substituted with (C₁-C₄)alkyl, —SCH₃, —OCH₃, or halo;
D is a bond, —C(O)—, —CH₂—, —CH(OH)—, —CH (NH₂)—, —O—, —S—, —S(O)—, —S(O)₂—, —NH—, —N((C₁-C₄)alkyl)-, —N((C₁-C₄)alkyl-OH)—, or —N(cyclopropyl)-;
W is (C₁-C₁₀)alkylene, 5- to 6-membered cycloalkylene, or ((C₁-C₄)alkylene)phenylene;
d is 0, 1, 2, or 3;
R⁴ is halo, —CF₃, (C₁-C₄)alkyl, or (C₁-C₄)alkoxy; and
L is a linker group selected from the group consisting of —C(O)—NR⁵—X¹—NR⁵—C(O)—, —S(O)₂—NR⁵—X¹—NR⁵—S(O)₂—, —NR⁵—C(O)—X²—C(O)—NR⁵—, and —NR⁵—S(O)₂—X²—S(O)₂—NR⁵—, where R⁵ is hydrogen or (C₁-C₄)alkyl; and X¹ and X² are (C₁-C₁₀)alkylene, —(O(C₁-C₃)alkylene)ₚ-, —((C₁-C₃)alkylene O)_q—, (C₂-C₁₀)alkenylene, phenylene, naphthylene, or bis(phenylene), where p and q are each independently 1, 2, 3 or 4;
or a pharmaceutically acceptable salt thereof.

8. The compound of claim 7 wherein A is pyridinyl or pyrimidyl; or a pharmaceutically acceptable salt thereof.

9. The compound of claim 7 wherein R¹ is hydrogen, and R² and R³ are both methyl; or a pharmaceutically acceptable salt thereof.

10. The compound of claim 7 wherein D is —C(O)—, —CH₂—, —O—, —NH—, —N((C₁-C₄)alkyl)-, or —N(cyclopropyl)-; or a pharmaceutically acceptable salt thereof.

11. The compound of claim 7 wherein M and M' are the same monomeric moiety; or a pharmaceutically acceptable salt thereof.

12. A compound of Formula M-L-M', wherein M and M' are the same and each are a monomeric moiety of Formula (III)

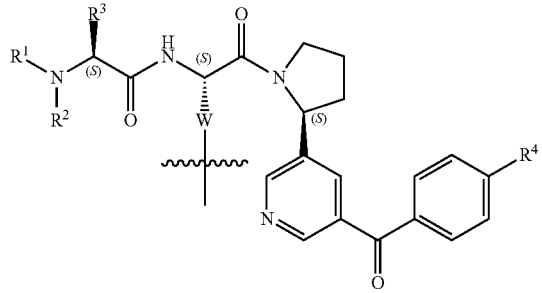

where,
R¹ is (C₁-C₄)alkyl or hydrogen;
R² is (C₁-C₄)alkyl or hydrogen;
R³ is (C₁-C₄)alkyl or hydrogen, or R¹ or R² along with the nitrogen to which R¹ or R² is attached is taken together with R³ to form an aziridinyl, azetidinyl, pyrrolidinyl, or piperidinyl;
R⁴ is fluorine;
W is (C₁-C₁₀)alkylene, or (C₁-C₄)alkylenephenylene; and
L is a linker group selected from the group consisting of —C(O)—NR⁵—X¹—NR⁵—C(O)—, —S(O)₂—NR⁵—X¹—NR⁵—S(O)₂—, —NR⁵—C(O)—X²—C(O)—NR⁵—, and —NR⁵—S(O)₂—X²—S(O)₂—NR⁵—, where R⁵ is hydrogen, and X¹ and X² are (C₁-C₁₀)alkylene, phenylene, naphthylene, or bis (phenylene);
or a pharmaceutically acceptable salt thereof.

13. The compound of claim 12 wherein R¹ is hydrogen; R² is methyl; and R³ is methyl; or a pharmaceutically acceptable salt thereof.

14. The compound of claim 12 where R¹ is hydrogen; and R² taken together with R³ forms an azetidinyl; or a pharmaceutically acceptable salt thereof.

15. The compound of claims 12 where W is n-butylene or —CH₂-(phenylene)-; or a pharmaceutically acceptable salt thereof.

16. The compound of claim 15 where W is n-butylene; or a pharmaceutically acceptable salt thereof.

17. The compound of claim 15 where W is a —CH₂—(phenylene)-; or a pharmaceutically acceptable salt thereof.

18. The compound of claims 12 where L is —NR⁵—C(O)—X²—C(O)—NR⁵—, where X² is n-propylene, n-butylene, n-pentylene, n-hexylene, n-heptylene, n-octylene, 1,3-phenylene, 1,4-phenylene, or 4,4'-biphenyl; or a pharmaceutically acceptable salt thereof.

19. The compound of claims 12 where L is —NR⁵—S(O)₂—X²—S(O)₂—NR⁵—, where X² is 1,3-phenylene, 4,4'-biphenyl, 2,7-naphthylene, or 2,6-naphthylene; or a pharmaceutically acceptable salt thereof.

20. A compound selected from the group consisting of Heptanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};
(S)—N—((S)-1-((S)-2-(5-(4-fluorobenzoyl)pyridin-3-yl) pyrrolidin-1-yl)-6-(3-(N—((S)-6-((S)-2-(5-(4-fluorobenzoyl)pyridin-3-yl)pyrrolidin-1-yl)-5-((S)-2-(methylamino)propanamido)-6-oxohexyl)sulfamoyl) phenylsulfonamido)-1-oxohexan-2-yl)-2-(methylamino)propanamide;
N,N'-Bis-[(S)-6-{(S)-2-[5-(4-fluoro-benzoyl)-pyridin-3-yl]-pyrrolidin-1-yl}-5-((S)-2-methylamino-propionylamino)-6-oxo-hexyl]-terephthalamide;
(S)—N—((S)-1-((S)-2-(5-(4-fluorobenzoyl)pyridin-3-yl) pyrrolidin-1-yl)-6-(4'-(N—((S)-6-((S)-2-(5-(4-fluorobenzoyl)pyridin-3-yl)pyrrolidin-1-yl)-5-((S)-2-(methylamino)propanamido)-6-oxohexyl)sulfamoyl) biphenyl-4-ylsulfonamido)-1-oxohexan-2-yl)-2-(methylamino)propanamide;
N,N'-Bis-[(S)-6-{(S)-2-[5-(4-fluoro-benzoyl)-pyridin-3-yl]-pyrrolidin-1-yl}-5-((S)-2-methylamino-propionylamino)-6-oxo-hexyl]-isophthalamide;
Nonanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};
Decanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};
(S)—N—((S)-1-((S)-2-(5-(4-fluorobenzoyl)pyridin-3-yl) pyrrolidin-1-yl)-6-(7-(N—((S)-6-((S)-2-(5-(4-fluorobenzoyl)pyridin-3-yl)pyrrolidin-1-yl)-5-((S)-2-(methylamino)propanamido)-6-oxohexyl)sulfamoyl) naphthalene-2-sulfonamido)-1-oxohexan-2-yl)-2-(methylamino)propanamide;

(S)—N—((S)-1-((S)-2-(5-(4-fluorobenzoyl)pyridin-3-yl) pyrrolidin-1-yl)-6-(6-(N—((S)-6-((S)-2-(5-(4-fluorobenzoyl)pyridin-3-yl)pyrrolidin-1-yl)-5-((S)-2-(methylamino)propanamido)-6-oxohexyl)sulfamoyl) naphthalene-2-sulfonamido)-1-oxohexan-2-yl)-2-(methylamino)propanamide;

Biphenyl-4,4'-dicarboxylic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};

Biphenyl-4,4'-dicarboxylic acid bis-[((S)-5-[((S)-azetidine-2-carbonyl)-amino]-6-{(S)-2-[5-(4-fluoro-benzoyl)-pyridin-3-yl]-pyrrolidin-1-yl}-6-oxo-hexyl)-amide];

Heptanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide);

Decanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide);

Hexanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide);

N,N'-Bis-{4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-isophthalamide;

Nonanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); and Pentanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide);

or a pharmaceutically acceptable salt thereof.

21. A compound of claim 20 selected from the group consisting of

Heptanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};

N,N'-Bis-[(S)-6-{(S)-2-[5-(4-fluoro-benzoyl)-pyridin-3-yl]-pyrrolidin-1-yl}-5-((S)-2-methylamino-propionylamino)-6-oxo-hexyl]-terephthalamide;

N,N'-Bis-[(S)-6-{(S)-2-[5-(4-fluoro-benzoyl)-pyridin-3-yl]-pyrrolidin-1-yl}-5-((S)-2-methylamino-propionylamino)-6-oxo-hexyl]-isophthalamide;

Nonanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};

Decanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};

Biphenyl-4,4'-dicarboxylic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};

Biphenyl-4,4'-dicarboxylic acid bis-[((S)-5-[((S)-azetidine-2-carbonyl)-amino]-6-{(S)-2-[5-(4-fluoro-benzoyl)-pyridin-3-yl]-pyrrolidin-1-yl}-6-oxo-hexyl)-amide];

Heptanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide);

Decanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); and Nonanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide);

or a pharmaceutically acceptable salt thereof.

22. A compound of claim 20 selected from the group consisting of

Biphenyl-4,4'-dicarboxylic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};

Decanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};

Decanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide);

Nonanedioic acid bis-{[(S)-6-{(S)-2-[5-(4-fluoro-benzoyl)-pyridin-3-yl]-pyrrolidin-1-yl}-5-((S)-2-methylamino-propionylamino)-6-oxo-hexyl]-amide};

Heptanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide); and Nonanedioic acid bis-({4-[(S)-3-{(S)-2-[5-(4-fluoro-benzoyl)-pyridin-3-yl]-pyrrolidin-1-yl}-2-((S)-2-methylamino-propionylamino)-3-oxo-propyl]-phenyl}-amide);

or a pharmaceutically acceptable salt thereof.

23. A pharmaceutical composition comprising a compound of claim 1, or a pharmaceutically acceptable salt thereof, and a pharmaceutically acceptable carrier, diluent or excipient.

24. The pharmaceutical composition of claim 23 further comprising at least one additional pharmaceutical agent.

25. The pharmaceutical composition of claim 24 wherein said at least one additional pharmaceutical agent is paclitaxel, a PI3K inhibitor, a topoisomerase inhibitor, a Trail antibody, recombinant Trail, or a Trail receptor agonist.

26. The pharmaceutical composition of claim 24 wherein said at least one additional pharmaceutical agent is paclitaxel.

27. A method for treating a disease, disorder, or condition associated with the overexpression of an IAP in a subject comprising the step of administering to a subject in need to such treatment a therapeutically effective amount of a compound according to claim 1, or a pharmaceutically acceptable salt thereof.

28. A method for treating a disease, disorder, or condition mediated by IAPs comprising the step of administering to a subject in need of such treatment a therapeutically effective amount of a compound as defined in claim 1, or a pharmaceutically acceptable salt thereof.

29. A method for treating a disease, disorder, or condition mediated by IAPs comprising the steps of administering to a patient in need of such treatment (i) a compound according to claim 1, or a pharmaceutically acceptable salt thereof; and (ii) at least one additional pharmaceutical agent.

30. The method of claim 29 wherein said additional pharmaceutical agent is paclitaxel, a PI3K inhibitor, a topoisomerase inhibitor, a Trail antibody, recombinant Trail, or a Trail receptor agonist.

31. The method of claim 29 wherein said additional pharmaceutical agent is paclitaxel.

32. The method of claim 29 wherein said compound, or pharmaceutically acceptable salt thereof, and said additional pharmaceutical agent are administered simultaneously.

33. The method of claim 29 wherein said compound, or pharmaceutically acceptable salt thereof, and said additional pharmaceutical agent are administered sequentially.

34. A method for treating a disease, disorder, or condition mediated by IAP comprising the step of administering to a patient in need of such treatment a pharmaceutical composition comprising a compound according to claim 1, or a pharmaceutically acceptable salt thereof, and a pharmaceutical acceptable carrier.

35. The method of claim 34 wherein said composition further comprises at least one additional pharmaceutical agent.

36. The method of claim 34 wherein said additional pharmaceutical agent is paclitaxel, a PI3K inhibitor, a topoisomerase inhibitor, a Trail antibody, recombinant Trail, or a Trail receptor agonist.

37. The method of claim 34 wherein said additional pharmaceutical agent is paclitaxel.

38. A method for treating a disease, disorder, or condition mediated by IAPs comprising the steps of administering to a patient in need of such treatment
   (i) a first composition comprising a compound according to claim 1, or a pharmaceutically acceptable salt thereof, and a pharmaceutical carrier; and
   (ii) a second composition comprising at least one additional pharmaceutical agent and a pharmaceutical carrier.

39. The method of claim 38 wherein said additional pharmaceutical agent is paclitaxel, a PI3K inhibitor, a topoisomerase inhibitor, a Trail antibody, recombinant Trail, or a Trail receptor agonist.

40. The method of claim 38 wherein said additional pharmaceutical agent is a paclitaxel.

41. The method of claim 38 wherein said first composition and said second composition are administered simultaneously.

42. The method of claim 38 wherein said first composition and said second composition are administered sequentially.

* * * * *